US008399619B2

(12) United States Patent
Trieu et al.

(10) Patent No.: US 8,399,619 B2
(45) Date of Patent: Mar. 19, 2013

(54) INJECTABLE COLLAGEN MATERIAL

(75) Inventors: Hai H. Trieu, Cordova, TN (US);
Jeffrey M. Gross, Memphis, TN (US);
Sean M. Haddock, Memphis, TN (US);
Keith M. Kinnane, Memphis, TN (US);
Thomas A. Simonton, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 307 days.

(21) Appl. No.: 11/480,067

(22) Filed: Jun. 30, 2006

(65) Prior Publication Data
US 2008/0004214 A1    Jan. 3, 2008

(51) Int. Cl.
A61K 38/39    (2006.01)
A61F 2/24    (2006.01)
A61F 2/30    (2006.01)

(52) U.S. Cl. .................. 530/356; 623/17.16; 623/908

(58) Field of Classification Search .............. 514/12, 514/54; 530/356; 623/17.16, 908
See application file for complete search history.

(56) References Cited

U.S. PATENT DOCUMENTS

| 3,551,560 A | 12/1970 | Thiele |
| 3,855,638 A | 12/1974 | Pilliar |
| 3,875,595 A | 4/1975 | Froning |
| 4,060,081 A | 11/1977 | Yannas et al. |
| 4,085,466 A | 4/1978 | Goodfellow et al. |
| 4,185,813 A | 1/1980 | Spann |
| 4,280,954 A | 7/1981 | Yannas et al. |
| 4,344,192 A | 8/1982 | Kenny |
| 4,349,921 A | 9/1982 | Kuntz |
| 4,350,629 A | 9/1982 | Yannas et al. |
| 4,378,224 A | 3/1983 | Nimni et al. |
| 4,400,833 A | 8/1983 | Kurland |
| 4,418,691 A | 12/1983 | Yannas et al. |
| 4,424,208 A | 1/1984 | Wallace et al. |
| 4,448,718 A | 5/1984 | Yannas et al. |
| 4,458,678 A | 7/1984 | Yannas et al. |
| 4,505,266 A | 3/1985 | Yannas et al. |
| 4,544,516 A | 10/1985 | Hughes et al. |
| 4,578,079 A | 3/1986 | Ruoslahti et al. |
| 4,582,640 A | 4/1986 | Smestad et al. |
| 4,589,881 A | 5/1986 | Pierschbacher et al. |
| 4,614,794 A | 9/1986 | Easton et al. |
| 4,627,853 A | 12/1986 | Campbell et al. |
| 4,642,117 A | 2/1987 | Nguyen et al. |
| 4,642,120 A | 2/1987 | Nevo et al. |
| 4,661,111 A | 4/1987 | Ruoslahti et al. |
| 4,703,108 A | 10/1987 | Silver et al. |
| 4,772,287 A | 9/1988 | Ray et al. |
| 4,787,900 A | 11/1988 | Yannas |
| 4,801,299 A | 1/1989 | Brendel et al. |
| 4,803,075 A | 2/1989 | Wallace et al. |
| 4,837,285 A | 6/1989 | Berg et al. |
| 4,879,135 A | 11/1989 | Greco et al. |
| 4,880,492 A | 11/1989 | Erdmann et al. |
| 4,904,260 A | 2/1990 | Ray et al. |
| 4,946,792 A | 8/1990 | O'Leary |
| 4,976,733 A | 12/1990 | Girardot |
| 5,007,934 A | 4/1991 | Stone |
| 5,067,962 A | 11/1991 | Campbell et al. |
| 5,106,949 A | 4/1992 | Kemp et al. |
| 5,108,438 A | 4/1992 | Stone |
| 5,110,604 A * | 5/1992 | Chu et al. .................. 424/484 |
| 5,137,514 A | 8/1992 | Ryan |
| 5,192,326 A | 3/1993 | Bao et al. |
| 5,229,497 A | 7/1993 | Boni |
| 5,258,043 A | 11/1993 | Stone |
| 5,397,352 A | 3/1995 | Burres |
| 5,478,739 A | 12/1995 | Slivka et al. |
| 5,507,810 A | 4/1996 | Prewett et al. |
| 5,549,679 A | 8/1996 | Kuslich |
| 5,562,736 A | 10/1996 | Ray et al. |
| 5,571,189 A | 11/1996 | Kuslich |
| 5,607,478 A | 3/1997 | Lentz et al. |
| 5,713,959 A | 2/1998 | Bartlett et al. |
| 5,733,337 A | 3/1998 | Carr, Jr. et al. |
| 5,788,625 A | 8/1998 | Plouhar et al. |
| 5,827,289 A | 10/1998 | Reiley et al. |
| 5,858,747 A | 1/1999 | Schinstine et al. |
| 5,888,220 A | 3/1999 | Felt et al. |
| 5,894,070 A | 4/1999 | Hansson et al. |

(Continued)

FOREIGN PATENT DOCUMENTS

DE    19959975 A1    7/2001
EP    0277678 A1    8/1988

(Continued)

OTHER PUBLICATIONS

Tay, B.K., et al., "Use of a collagen-hydroxyapatite matrix in spinal fusion. A rabbit model," SPINE, vol. 23, No. 21, pp. 2276-2281, Nov. 1, 1998.
Burres, S., "Fascian," Facial Plast Surg, vol. 20, No. 2, pp. 149-152, May 2004.
Burres, S., "Midface volume replacement with a transmaxiallary implant," Aesthetic Plast Surg, vol. 29, No. 1, pp. 1-4, Jan.-Feb. 2005.
Burres, S., "Soft-tissue augmentation with fascian," Clin Plast Surg, vol. 28, No. 1, pp. 101-110, Jan. 2001. Abstract Only.
Burres, S., "Preserved particulate fascia lata for injection. A new alternative," vol. 25, No. 10, pp. 790-794, Oct. 1999.
"Fascia & Fascian" http://fascian.com/fascian.htm. Apr. 25, 2003, 9 pgs.

(Continued)

*Primary Examiner* — Chih-Min Kam

(57) ABSTRACT

A collagen material is disclosed and can include a plurality of particles. Each particle can include an elongated, thin body having one or more arcuate portions and one or more straight portions. Further, each particle can include one or more fibers extending from the body. One or more fibers of one particle can engage the one or more fibers of one or more other particles to establish a matrix of material, where a cross-linking agent may be added in the collagen material. Furthermore, an additive including a radiocontrast medium, a drug, a cellular matter, a biological factor, or a combination thereof may be added to the collagen mixture.

27 Claims, 41 Drawing Sheets

U.S. PATENT DOCUMENTS

| | | |
|---|---|---|
| 5,916,870 A | 6/1999 | Lee et al. |
| 5,922,028 A | 7/1999 | Plouhar et al. |
| 5,935,849 A | 8/1999 | Schinstine et al. |
| 5,948,428 A | 9/1999 | Lee et al. |
| 5,964,807 A | 10/1999 | Gan et al. |
| 5,976,186 A | 11/1999 | Bao et al. |
| 5,980,504 A | 11/1999 | Sharkey et al. |
| 5,994,325 A | 11/1999 | Roufa et al. |
| 6,007,570 A | 12/1999 | Sharkey et al. |
| 6,022,376 A | 2/2000 | Assell et al. |
| 6,025,538 A | 2/2000 | Yaccarino, III |
| 6,027,743 A | 2/2000 | Khouri et al. |
| 6,046,379 A | 4/2000 | Stone et al. |
| 6,066,154 A | 5/2000 | Reiley et al. |
| 6,073,051 A | 6/2000 | Sharkey et al. |
| 6,077,989 A | 6/2000 | Kandel et al. |
| 6,080,194 A | 6/2000 | Pachence et al. |
| 6,080,579 A | 6/2000 | Hanley, Jr. et al. |
| 6,095,149 A | 8/2000 | Sharkey et al. |
| 6,099,514 A | 8/2000 | Sharkey et al. |
| 6,122,549 A | 9/2000 | Sharkey et al. |
| 6,123,731 A | 9/2000 | Boyce et al. |
| 6,126,682 A | 10/2000 | Sharkey et al. |
| 6,140,452 A | 10/2000 | Felt et al. |
| 6,146,422 A | 11/2000 | Lawson |
| 6,165,489 A | 12/2000 | Berg et al. |
| 6,176,880 B1 | 1/2001 | Plouhar et al. |
| 6,179,872 B1 | 1/2001 | Bell et al. |
| 6,197,061 B1 | 3/2001 | Masuda et al. |
| 6,224,630 B1 | 5/2001 | Bao et al. |
| 6,235,043 B1 | 5/2001 | Reiley et al. |
| 6,240,926 B1 | 6/2001 | Chin Gan et al. |
| 6,248,110 B1 | 6/2001 | Reiley et al. |
| 6,248,131 B1 | 6/2001 | Felt et al. |
| 6,261,311 B1 | 7/2001 | Sharkey et al. |
| 6,264,659 B1 | 7/2001 | Ross et al. |
| 6,264,695 B1 | 7/2001 | Stoy |
| 6,290,715 B1 | 9/2001 | Sharkey et al. |
| 6,306,169 B1 | 10/2001 | Lee et al. |
| 6,306,177 B1 | 10/2001 | Felt et al. |
| 6,306,189 B1 | 10/2001 | Renz |
| 6,322,786 B1 | 11/2001 | Anderson |
| 6,324,710 B1 | 12/2001 | Hernandez et al. |
| 6,340,369 B1 | 1/2002 | Ferree |
| 6,344,058 B1 | 2/2002 | Ferree |
| 6,352,557 B1 | 3/2002 | Ferree |
| 6,352,558 B1 | 3/2002 | Spector |
| 6,402,784 B1 | 6/2002 | Wardlaw |
| 6,419,702 B1 | 7/2002 | Ferree |
| 6,423,083 B2 | 7/2002 | Reiley et al. |
| 6,425,919 B1 | 7/2002 | Lambrecht |
| 6,428,576 B1 | 8/2002 | Haldimann |
| 6,436,119 B1 | 8/2002 | Erb et al. |
| 6,443,988 B2 | 9/2002 | Felt et al. |
| 6,482,235 B1 | 11/2002 | Lambrecht et al. |
| 6,592,625 B2 | 7/2003 | Cauthen |
| 6,623,963 B1 | 9/2003 | Muller et al. |
| 6,641,587 B2 | 11/2003 | Scribner et al. |
| 6,648,918 B2 | 11/2003 | Ferree |
| 6,662,805 B2 | 12/2003 | Frondoza et al. |
| 6,699,294 B2 | 3/2004 | Urry et al. |
| 6,712,853 B2 | 3/2004 | Kuslich |
| 6,716,251 B1 | 4/2004 | Asius et al. |
| 6,723,335 B1 | 4/2004 | Moehlenbruck et al. |
| 6,726,691 B2 | 4/2004 | Osorio et al. |
| 6,783,546 B2 | 8/2004 | Zucherman et al. |
| 6,793,677 B2 | 9/2004 | Ferree |
| 6,827,716 B2 | 12/2004 | Ryan et al. |
| 6,929,640 B1 | 8/2005 | Underwood et al. |
| 6,932,843 B2 | 8/2005 | Smith et al. |
| 6,936,072 B2 | 8/2005 | Lambrecht et al. |
| 6,939,329 B1 | 9/2005 | Verkaart |
| 6,958,077 B2 | 10/2005 | Suddaby |
| 6,969,404 B2 | 11/2005 | Ferree |
| 6,980,862 B2 | 12/2005 | Fredricks et al. |
| 7,001,431 B2 | 2/2006 | Bao et al. |
| 7,060,103 B2 | 6/2006 | Carr, Jr. et al. |
| 7,077,865 B2 | 7/2006 | Bao et al. |
| 2001/0004710 A1 | 6/2001 | Felt et al. |
| 2001/0006948 A1 | 7/2001 | Kang et al. |
| 2001/0011174 A1 | 8/2001 | Reiley et al. |
| 2001/0016195 A1 | 8/2001 | Tobinick |
| 2001/0016772 A1 | 8/2001 | Lee et al. |
| 2001/0020476 A1 | 9/2001 | Gan et al. |
| 2001/0024823 A1 | 9/2001 | Vukicevic et al. |
| 2001/0027199 A1 | 10/2001 | Olmarker et al. |
| 2001/0049527 A1 | 12/2001 | Cragg |
| 2001/0049531 A1 | 12/2001 | Reiley et al. |
| 2001/0051834 A1 | 12/2001 | Frondoza et al. |
| 2001/0055594 A1 | 12/2001 | Olmarker et al. |
| 2002/0016583 A1 | 2/2002 | Cragg |
| 2002/0026195 A1 | 2/2002 | Layne et al. |
| 2002/0029083 A1 | 3/2002 | Zucherman et al. |
| 2002/0032155 A1 | 3/2002 | Ferree |
| 2002/0038150 A1 | 3/2002 | Urry |
| 2002/0045942 A1 | 4/2002 | Ham |
| 2002/0049498 A1 | 4/2002 | Yuksel et al. |
| 2002/0055143 A1* | 5/2002 | Bell et al. .................... 435/69.1 |
| 2002/0068974 A1 | 6/2002 | Kuslich et al. |
| 2002/0068975 A1 | 6/2002 | Teitelbaum et al. |
| 2002/0082608 A1 | 6/2002 | Reiley et al. |
| 2002/0115742 A1 | 8/2002 | Trieu et al. |
| 2002/0116069 A1 | 8/2002 | Urry |
| 2002/0120347 A1 | 8/2002 | Boyer, II et al. |
| 2002/0133231 A1 | 9/2002 | Ferree |
| 2002/0151979 A1 | 10/2002 | Lambrecht et al. |
| 2002/0176893 A1 | 11/2002 | Wironen et al. |
| 2002/0177866 A1 | 11/2002 | Weikel et al. |
| 2003/0008817 A1 | 1/2003 | Sander et al. |
| 2003/0104026 A1 | 6/2003 | Wironen et al. |
| 2003/0130664 A1 | 7/2003 | Boucher et al. |
| 2003/0158607 A1 | 8/2003 | Carr et al. |
| 2004/0010251 A1 | 1/2004 | Pitaru et al. |
| 2004/0024081 A1 | 2/2004 | Trieu et al. |
| 2004/0030392 A1 | 2/2004 | Lambrecht et al. |
| 2004/0034429 A1 | 2/2004 | Lambrecht et al. |
| 2004/0039392 A1 | 2/2004 | Trieu |
| 2004/0054414 A1 | 3/2004 | Trieu et al. |
| 2004/0059418 A1 | 3/2004 | McKay et al. |
| 2004/0064023 A1 | 4/2004 | Ryan et al. |
| 2004/0073308 A1 | 4/2004 | Kuslich et al. |
| 2004/0083001 A1 | 4/2004 | Kandel |
| 2004/0083002 A1 | 4/2004 | Belef et al. |
| 2004/0091540 A1 | 5/2004 | Desrosiers et al. |
| 2004/0092946 A1 | 5/2004 | Bagga et al. |
| 2004/0101959 A1 | 5/2004 | Marko et al. |
| 2004/0172132 A1 | 9/2004 | Ginn |
| 2004/0186471 A1 | 9/2004 | Trieu |
| 2004/0220101 A1 | 11/2004 | Ferree |
| 2004/0220102 A1 | 11/2004 | Ferree |
| 2004/0228901 A1 | 11/2004 | Trieu et al. |
| 2004/0229786 A1 | 11/2004 | Attawia et al. |
| 2004/0260397 A1 | 12/2004 | Lambrecht et al. |
| 2005/0002909 A1 | 1/2005 | Moehlenbruck et al. |
| 2005/0055094 A1 | 3/2005 | Kuslich |
| 2005/0069571 A1 | 3/2005 | Slivka et al. |
| 2005/0070915 A1 | 3/2005 | Mazzuca et al. |
| 2005/0090901 A1 | 4/2005 | Studer |
| 2005/0100538 A1 | 5/2005 | Mohamed et al. |
| 2005/0102030 A1 | 5/2005 | Yuksel et al. |
| 2005/0113923 A1 | 5/2005 | Acker et al. |
| 2005/0118228 A1 | 6/2005 | Trieu |
| 2005/0119750 A1 | 6/2005 | Studer |
| 2005/0119754 A1 | 6/2005 | Trieu et al. |
| 2005/0125066 A1 | 6/2005 | McAfee |
| 2005/0131540 A1 | 6/2005 | Trieu |
| 2005/0131541 A1 | 6/2005 | Trieu |
| 2005/0143688 A1 | 6/2005 | Lin et al. |
| 2005/0149007 A1 | 7/2005 | Carl |
| 2005/0149046 A1 | 7/2005 | Friedman |
| 2005/0149197 A1 | 7/2005 | Cauthen |
| 2005/0152986 A1 | 7/2005 | Duneas et al. |
| 2005/0154463 A1 | 7/2005 | Trieu |
| 2005/0159817 A1 | 7/2005 | Ferree |
| 2005/0177168 A1 | 8/2005 | Brunnett et al. |
| 2005/0182414 A1 | 8/2005 | Manzi et al. |
| 2005/0182418 A1 | 8/2005 | Boyd et al. |

| | | | |
|---|---|---|---|
| 2005/0186673 A1 | 8/2005 | Geistlich et al. | |
| 2005/0187543 A1 | 8/2005 | Underwood et al. | |
| 2005/0187556 A1 | 8/2005 | Stack et al. | |
| 2005/0191331 A1 | 9/2005 | Hunter et al. | |
| 2005/0196387 A1 | 9/2005 | Seyedin et al. | |
| 2005/0197707 A1 | 9/2005 | Trieu et al. | |
| 2005/0203206 A1 | 9/2005 | Trieu | |
| 2005/0203527 A1 | 9/2005 | Carrison et al. | |
| 2005/0203537 A1 | 9/2005 | Wiley et al. | |
| 2005/0209595 A1 | 9/2005 | Karmon | |
| 2005/0209601 A1 | 9/2005 | Bowman et al. | |
| 2005/0209602 A1 | 9/2005 | Bowman et al. | |
| 2005/0222538 A1 | 10/2005 | Embry et al. | |
| 2005/0222684 A1 | 10/2005 | Ferree | |
| 2005/0234493 A1 | 10/2005 | Carr et al. | |
| 2005/0234498 A1 | 10/2005 | Gronemeyer et al. | |
| 2005/0234557 A1 | 10/2005 | Lambrecht et al. | |
| 2005/0240171 A1 | 10/2005 | Forrest | |
| 2005/0251259 A1 | 11/2005 | Suddaby | |
| 2005/0256580 A1 | 11/2005 | Marissen | |
| 2005/0261684 A1 | 11/2005 | Shaolian et al. | |
| 2005/0267580 A1 | 12/2005 | Suddaby | |
| 2005/0267583 A1 | 12/2005 | Higham et al. | |
| 2005/0273093 A1 | 12/2005 | Patel et al. | |
| 2005/0277996 A1 | 12/2005 | Podhajsky | |
| 2006/0004456 A1 | 1/2006 | McKay | |
| 2006/0019869 A1 | 1/2006 | DiMauro et al. | |
| 2007/0026053 A1 | 2/2007 | Pedrozo et al. | |

FOREIGN PATENT DOCUMENTS

| | | | |
|---|---|---|---|
| EP | 0305028 B1 | 3/1989 | |
| EP | 0747067 A2 | 12/1996 | |
| EP | 1416867 A1 | 5/2004 | |
| EP | 1421957 A1 | 5/2004 | |
| EP | 1328222 B1 | 3/2005 | |
| EP | 1517655 A1 | 3/2005 | |
| EP | 1214026 B1 | 4/2005 | |
| EP | 1198209 B1 | 5/2005 | |
| EP | 1545352 A1 | 6/2005 | |
| EP | 1545362 A2 | 6/2005 | |
| EP | 1549261 A2 | 7/2005 | |
| EP | 1549262 A1 | 7/2005 | |
| EP | 1051207 B1 | 8/2005 | |
| EP | 1562652 A1 | 8/2005 | |
| EP | 1563808 A1 | 8/2005 | |
| EP | 1563809 A2 | 8/2005 | |
| EP | 157458 A1 | 9/2005 | |
| EP | 1582166 A2 | 10/2005 | |
| EP | 1585448 A1 | 10/2005 | |
| EP | 1585555 A2 | 10/2005 | |
| EP | 1313412 B1 | 11/2005 | |
| EP | 1407729 B1 | 11/2005 | |
| EP | 1594421 A2 | 11/2005 | |
| EP | 1594423 A2 | 11/2005 | |
| EP | 1594558 A1 | 11/2005 | |
| EP | 1610833 A2 | 1/2006 | |
| GB | 1515963 | 6/1978 | |
| GB | 2407580 A | 5/2005 | |
| JP | 03124800 A | * | 5/1991 |
| JP | 2005-103296 A | 4/2005 | |
| JP | 2005/118436 A | 5/2005 | |
| JP | 2005-152501 A | 6/2005 | |
| WO | 8910728 A1 | 11/1989 | |
| WO | 9210982 A1 | 7/1992 | |
| WO | 9611642 A1 | 4/1996 | |
| WO | WO 97/22371 A1 | 6/1997 | |
| WO | 9904720 A1 | 2/1999 | |
| WO | WO 99/43271 A1 | 9/1999 | |
| WO | 9959669 A1 | 11/1999 | |
| WO | 9961084 A1 | 12/1999 | |
| WO | 9962439 A1 | 12/1999 | |
| WO | 00/34556 | 6/2000 | |
| WO | WO 00/62832 A1 | 10/2000 | |
| WO | WO 00/75659 A1 | 12/2000 | |
| WO | WO 01/76654 A1 | 10/2001 | |
| WO | WO 02/00142 A1 | 1/2002 | |
| WO | 0217825 A2 | 3/2002 | |
| WO | WO 02/40070 A1 | 5/2002 | |
| WO | WO 02/054978 A1 | 7/2002 | |
| WO | WO 03/066120 A2 | 8/2003 | |
| WO | 03/099230 A2 | 12/2003 | |
| WO | WO 2004/032808 A2 | 2/2004 | |
| WO | WO 2004/026189 A2 | 4/2004 | |
| WO | WO 2004/026190 A2 | 4/2004 | |
| WO | WO 2004/041075 A2 | 5/2004 | |
| WO | WO 2004/045667 A1 | 6/2004 | |
| WO | WO 2004/060425 A2 | 7/2004 | |
| WO | WO 2004/073532 A1 | 9/2004 | |
| WO | WO 2004/073563 A2 | 9/2004 | |
| WO | WO 2004/093934 A2 | 11/2004 | |
| WO | WO 2005/000283 A2 | 1/2005 | |
| WO | WO 2005/004755 A1 | 1/2005 | |
| WO | WO 2005/032434 A1 | 4/2005 | |
| WO | WO 2005/034781 A1 | 4/2005 | |
| WO | WO 2005/034800 A2 | 4/2005 | |
| WO | WO 2005/041813 A2 | 5/2005 | |
| WO | WO 2005/049055 A1 | 6/2005 | |
| WO | WO 2005/063316 A1 | 7/2005 | |
| WO | WO 2005/070071 A2 | 8/2005 | |
| WO | WO 2005070439 A1 | 8/2005 | |
| WO | WO 2005/081870 A2 | 9/2005 | |
| WO | WO 2005/092248 A1 | 10/2005 | |
| WO | WO 2005/092249 A1 | 10/2005 | |
| WO | WO 2005/096978 A1 | 10/2005 | |
| WO | WO 2005/099392 A2 | 10/2005 | |
| WO | WO 2005/102433 A2 | 11/2005 | |
| WO | WO 2005/102440 A1 | 11/2005 | |
| WO | WO 2005/105168 A1 | 11/2005 | |
| WO | WO 2005/107827 A1 | 11/2005 | |
| WO | WO 2005/113032 A2 | 12/2005 | |
| WO | WO 2005/118015 A1 | 12/2005 | |
| WO | WO 2006/002417 A2 | 1/2006 | |
| WO | 2006/138098 A1 | 12/2006 | |

OTHER PUBLICATIONS

Burres, S., "Intralingual injection of particulate fascia for tongue paralysis," Rhinological and Otological Society, Inc., The Laryngoscope, vol. 114, pp. 1204-1205, Jul. 2004.

Shore, J. W., "Injectable lyophilized particulate human fascia lata (fascian) for lip, perioral, and glabellar enhancement," Ophthalmic Plastic and Reconstructive Surgery, vol. 16, No. 1, pp. 23-27, Jan. 2000.

Images 1 and 2 (author not available).

* cited by examiner

INJECTABLE COLLAGEN MATERIAL

FIELD OF THE DISCLOSURE

The present disclosure relates generally to orthopedics and orthopedic surgeries. More specifically, the present disclosure relates to materials, methods, and devices for treating intervertebral discs, synovial joints, and other tissue.

BACKGROUND

In human anatomy, the spine is a generally flexible column that can take tensile and compressive loads. The spine also allows bending motion and provides a place of attachment for keels, muscles and ligaments. Generally, the spine is divided into three sections: the cervical spine, the thoracic spine and the lumbar spine. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column may be subjected. At the same time, the intervertebral discs can allow adjacent vertebral bodies to move relative to each other a limited amount, particularly during bending, or flexure, of the spine. Thus, the intervertebral discs are under constant muscular and/or gravitational pressure and generally, the intervertebral discs are the first parts of the lumbar spine to show signs of deterioration.

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

DETAILED DESCRIPTION OF THE DRAWINGS

A collagen material is disclosed and can include a plurality of particles. Each particle can include an elongated, thin body having one or more arcuate portions and one or more straight portions. Further, each particle can include one or more fibers extending from the body. One or more fibers of one particle can engage the one or more fibers of one or more other particles to establish a matrix of material.

In another embodiment, a collagen material is disclosed and can include a plurality of particles. Each particle can include an elongated, thin body having one or more arcuate portions and one or more straight portions. Moreover, each particle can include one or more ribbon-shaped fibers extending from the body, one or more loop-shaped fibers extending from the body, and one or more hook-shaped fibers extending from the body.

In yet another embodiment, a kit for field use is disclosed and can include a syringe, a collagen material having a density less than or equal to one gram per cubic centimeter, and a fluid.

Description of Relevant Anatomy

Figure 1:
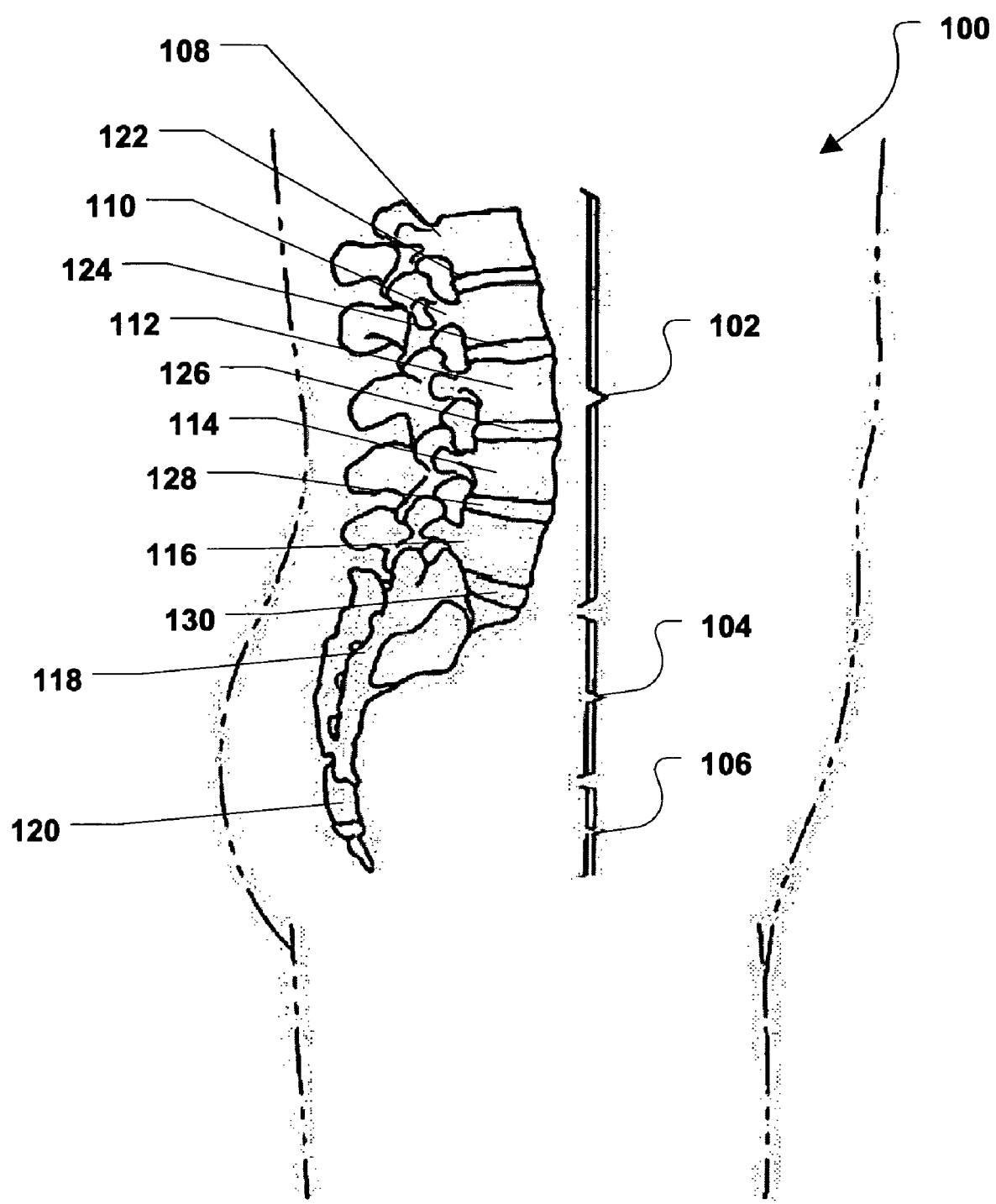
FIG. 1 is a lateral view of a portion of a vertebral column.

Referring initially to FIG. 1, a portion of a vertebral column, designated 100, is shown. As depicted, the vertebral column 100 includes a lumbar region 102, a sacral region 104, and a coccygeal region 106. As is known in the art, the vertebral column 100 also includes a cervical region and a thoracic region. For clarity and ease of discussion, the cervical region and the thoracic region are not illustrated.

As shown in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, damaged, or otherwise in need of repair, augmentation or treatment, that intervertebral lumbar disc 122, 124, 126, 128, 130 can be treated in accordance with one or more of the embodiments described herein.

Figure 2:
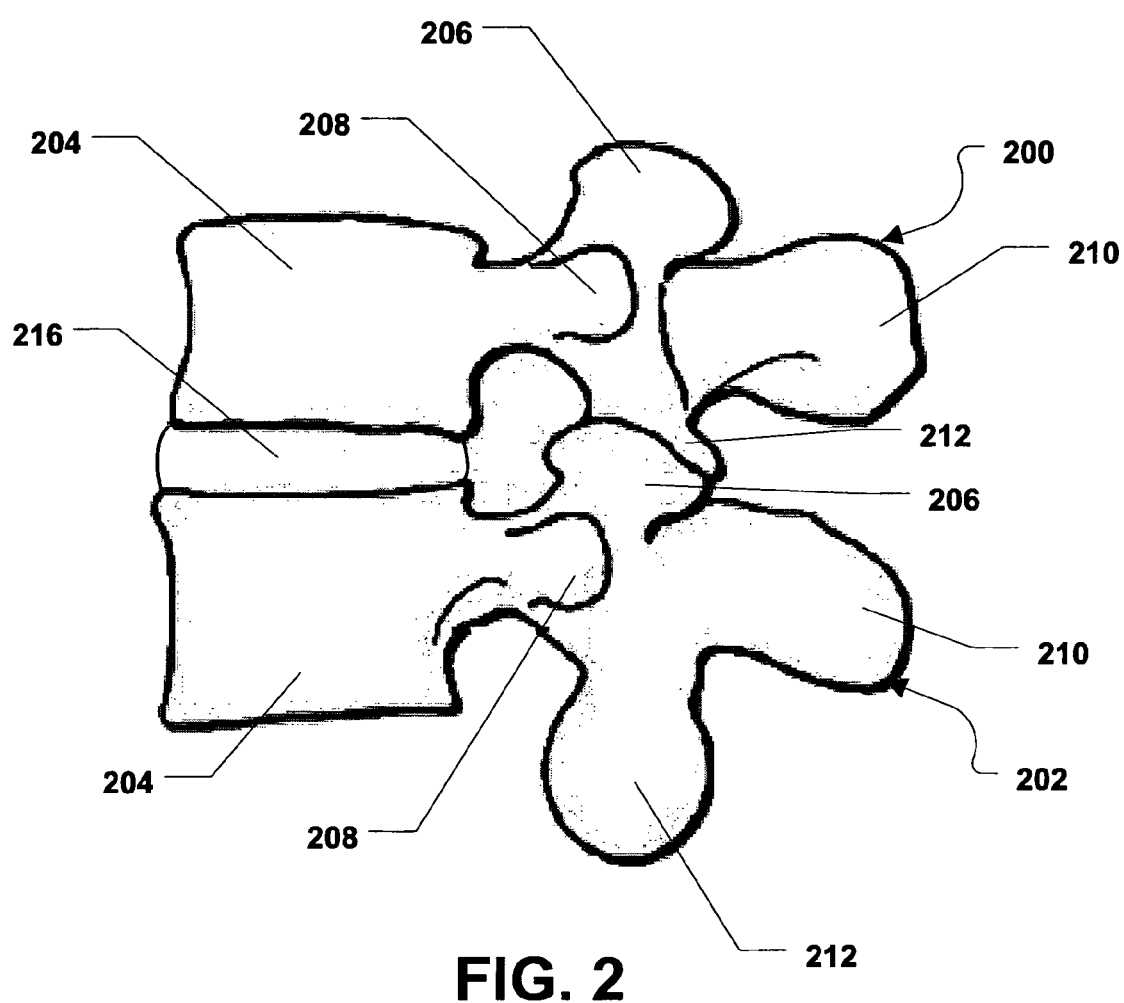
FIG. 2 is a lateral view of a pair of adjacent vertrebrae.

FIG. 2 depicts a detailed lateral view of two adjacent vertebrae, e.g., two of the lumbar vertebra 108, 110, 112, 114, 116 shown in FIG. 1. FIG. 2 illustrates a superior vertebra 200 and an inferior vertebra 202. As shown, each vertebra 200, 202 includes a vertebral body 204, a superior articular process 206, a transverse process 208, a spinous process 210 and an inferior articular process 212. FIG. 2 further depicts an intervertebral disc 216 between the superior vertebra 200 and the inferior vertebra 202. As described in greater detail below, a collagen material according to one or more of the embodiments described herein can be injected within the intervertebral disc 216 to treat a degenerative or otherwise deleterious condition.

Figure 3:
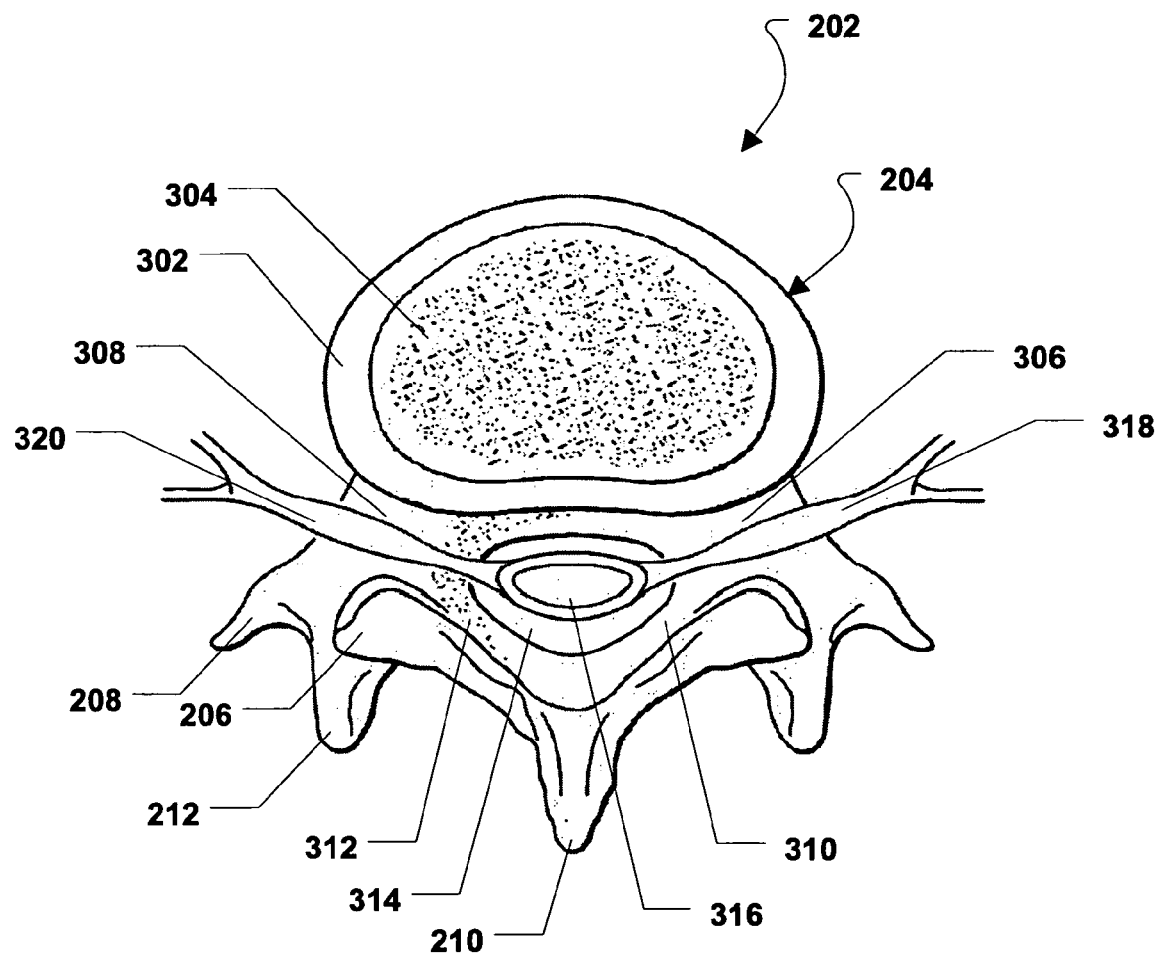
FIG. 3 is a top plan view of a vertebra.

Referring to FIG. 3, a vertebra, e.g., the inferior vertebra 202 (FIG. 2), is illustrated. As shown, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

It is well known in the art that the vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Figure 4:
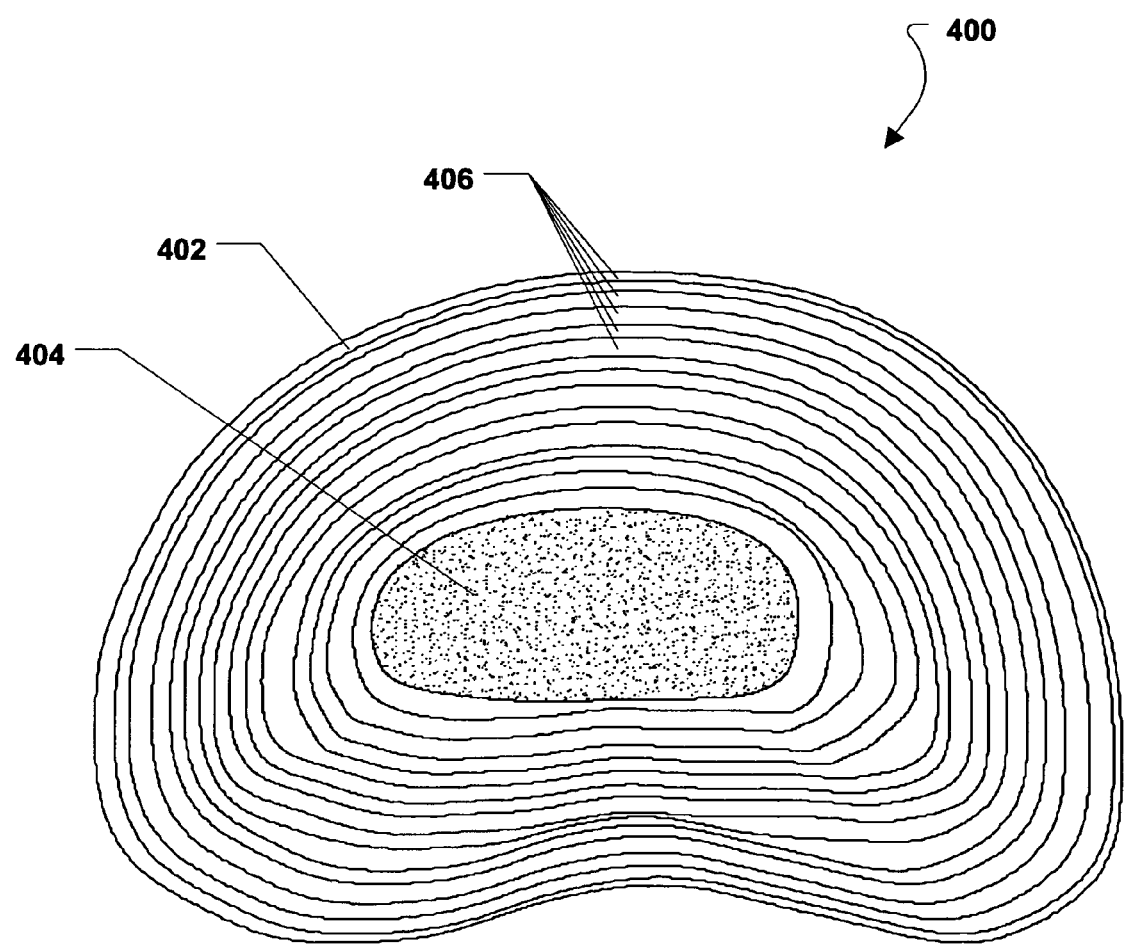
FIG. 4 is a cross-section view of an intervertebral disc.

Referring now to FIG. 4, an intervertebral disc is shown and is generally designated 400. The intervertebral disc 400 is made up of two components: the annulus fibrosis 402 and the nucleus pulposus 404. The annulus fibrosis 402 is the outer portion of the intervertebral disc 400, and the annulus fibrosis 402 includes a plurality of lamellae 406. The lamellae 406 are layers of collagen and proteins. Each lamella 406 includes fibers that slant at 30-degree angles, and the fibers of each lamella 406 run in a direction opposite the adjacent layers. Accordingly, the annulus fibrosis 402 is a structure that is exceptionally strong, yet extremely flexible.

The nucleus pulposus 404 is the inner gel material that is surrounded by the annulus fibrosis 402. It makes up about forty percent (40%) of the intervertebral disc 400 by weight. Moreover, the nucleus pulposus 404 can be considered a ball-like gel that is contained within the lamellae 406. The nucleus pulposus 404 includes loose collagen fibers, water, and proteins. The water content of the nucleus pulposus 404 is about ninety percent (90%) by weight at birth and decreases to about seventy percent by weight (70%) by the fifth decade.

Injury or aging of the annulus fibrosis 402 may allow the nucleus pulposus 404 to be squeezed through the annulus fibers either partially, causing the disc to bulge, or completely, allowing the disc material to escape the intervertebral disc 400. The bulging disc or nucleus material may compress the nerves or spinal cord, causing pain. Accordingly, the nucleus pulposus 404 can be removed and replaced with an artificial nucleus.

Figure 5:
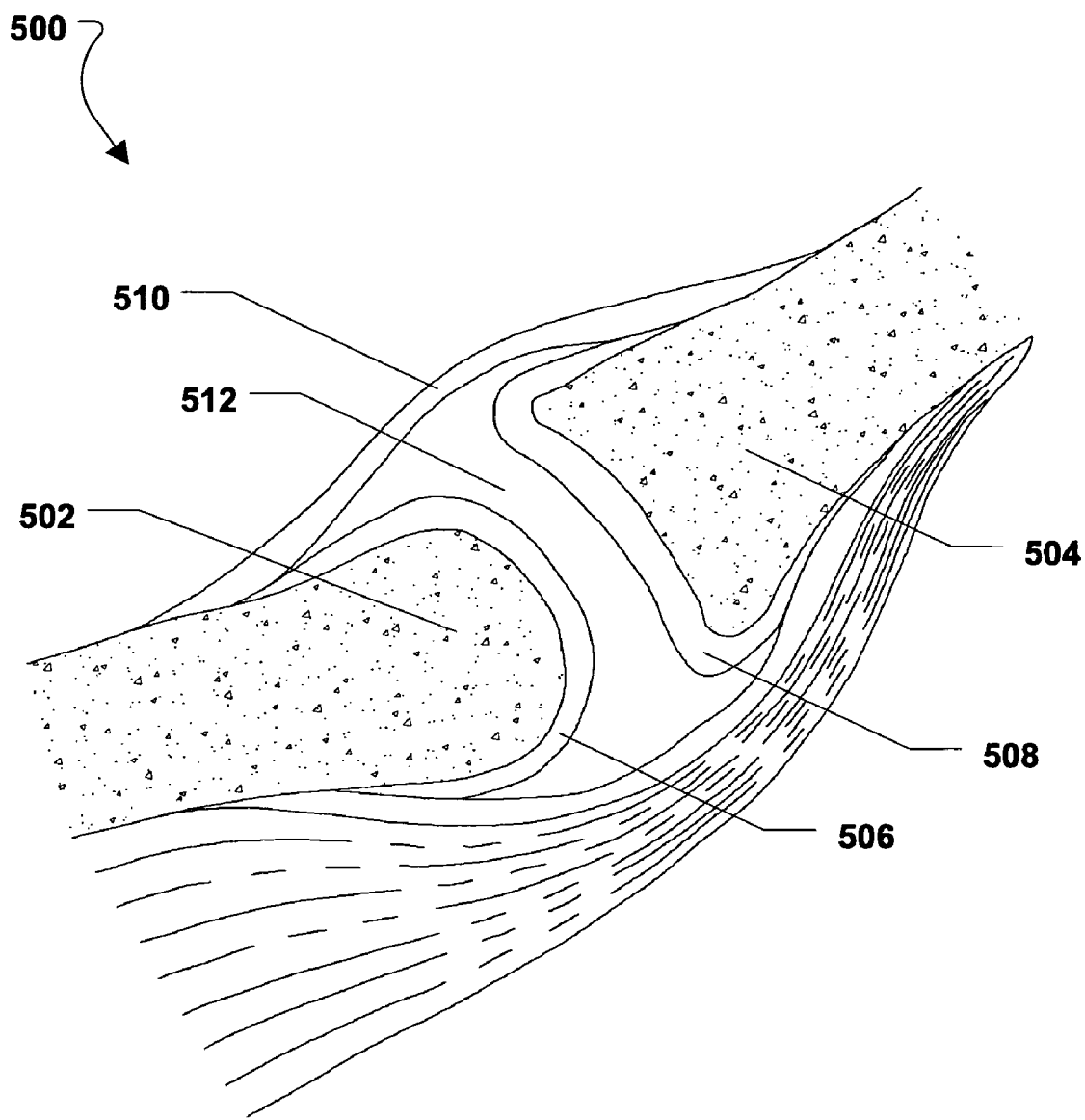
FIG. 5 is a cross-section view of a synovial joint.

Referring to FIG. 5, an exemplary synovial joint is shown and is generally designated 500. As shown, the synovial joint 500 includes a first bone end 502 and a second bone end 504. The first bone end 502 can be covered by a first cartilage layer 506. Further, the second bone end 504 can be covered by a second cartilage layer 508. In a particular embodiment, the cartilage layers 506, 508 can be articular cartilage. Moreover, the bone ends 502, 504 and the cartilage layers 506, 508 can be surrounded by a joint capsule 510.

In a particular embodiment, the joint capsule 510 of the synovial joint 500 can produce synovial fluid 512. The joint capsule 510 and the synovial fluid 512 can protect, support, and lubricate the cartilage layers 506, 508 and the connective tissue. Further, the synovial fluid can carry nutrients to the cartilage layers 506, 508 and can remove metabolic wastes from the cartilage layers 506, 508. Unfortunately, the cartilage layers 506, 508 can have a limited capacity for repair when damaged. Also, the natural aging process can cause the cartilage layers 506, 508 to slowly degenerate, which can reduce the capacity of the cartilage layers 506, 508 to protect and cushion the bone ends 502, 504.

In a particular embodiment, the synovial joint 500 can be a zygapophysial joint, i.e., a facet joint. Facet joints are located where adjacent vertebrae connect to each other. Each facet joint comprises two facet bones: an inferior facet and a superior facet. Further, the inferior facet of one vertebra can be connected to the superior facet of an adjacent vertebra. The facet joints can facilitate movement of the vertebrae relative to each other and can allow the spine to bend and twist.

As in the synovial joint 500, shown in FIG. 5, each facet bone includes a cartilage layer at the area of contact and the cartilage layers can be lubricated by a thin layer of synovial fluid. The cartilage layers and the synovial fluid decrease friction at the joint, extending joint life and preventing inflammation and associated pain.

As the natural aging process progresses, the cartilage layers covering the facet bones may deteriorate and may start to fray. When the cartilage layers fray, pieces of cartilage can break free and surfaces that were smooth can become rough. Further, the facet bones can rub together and create friction, which can lead to further deterioration of the joint. Moreover, the nerves associated with the facet joint can become irritated and inflamed, which can cause severe pain and can restrict movement of the spine.

Description of a Collagen Material

FIG. 6 through FIG. 18 show various scanning electron microscope (SEM) images of a collagen material manufactured according to one or more of the methods of manufacture described herein. In a particular embodiment, the collagen material can be allogenic, xenogenic, autogenic, recombinant, or a combination thereof.

Figure 6:
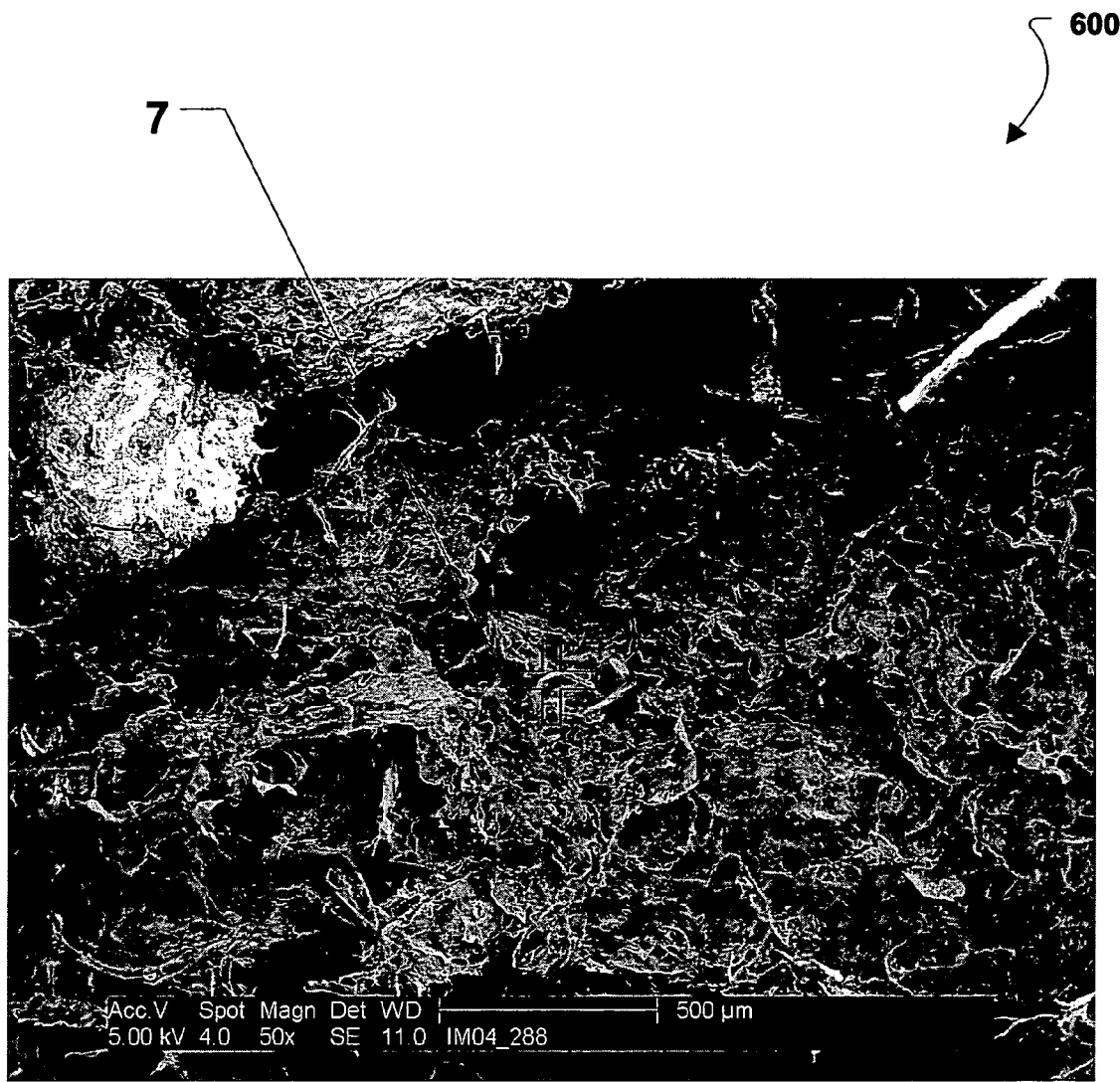
FIG. 6 is a scanning electron microscope (SEM) image of a sample of coated collagen material taken at a magnification of fifty times (50×)
Figure 7:
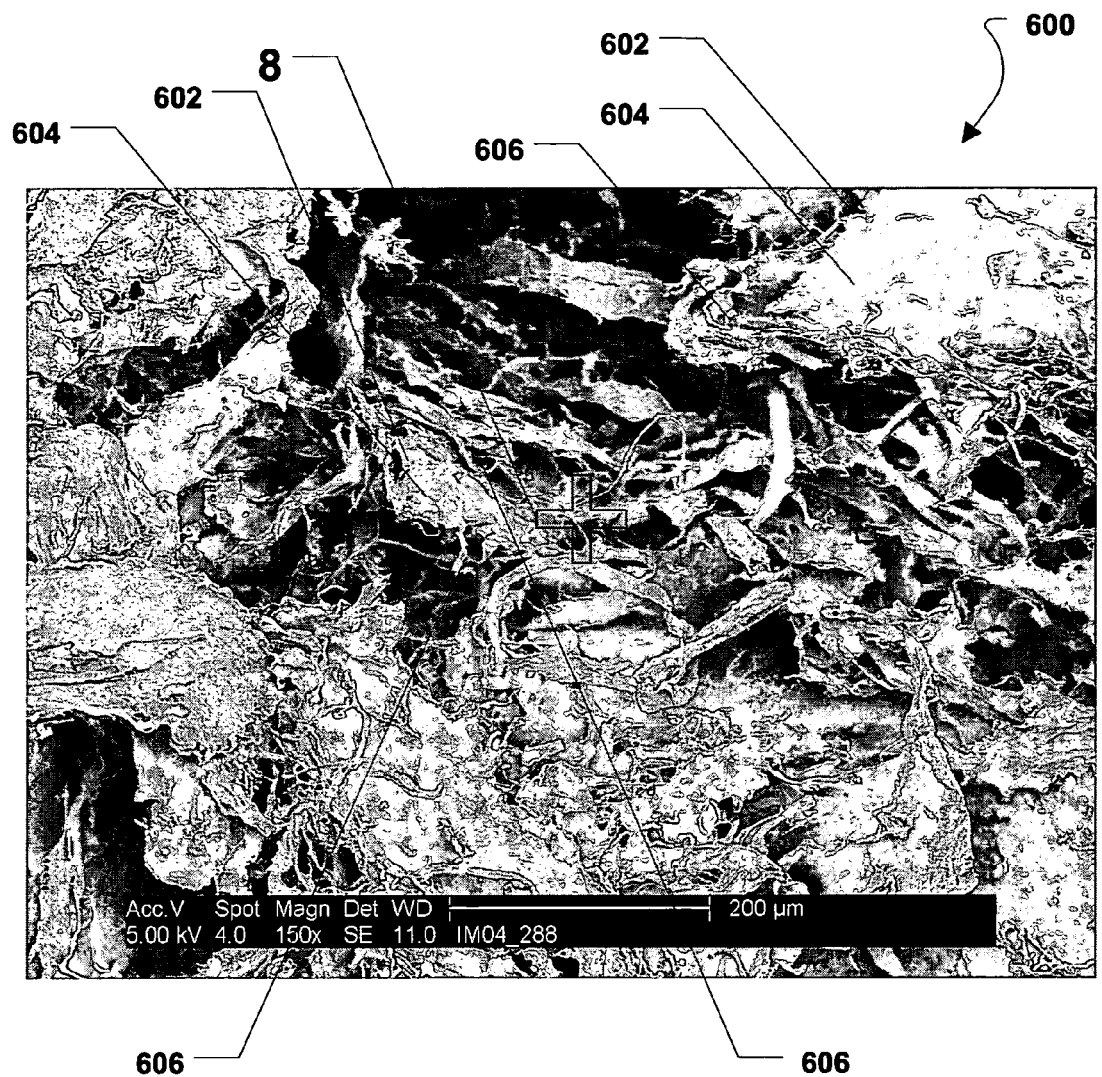
FIG. 7 is an SEM image of the sample of coated collagen material taken at a magnification of one hundred and fifty times (150×)
Figure 8:
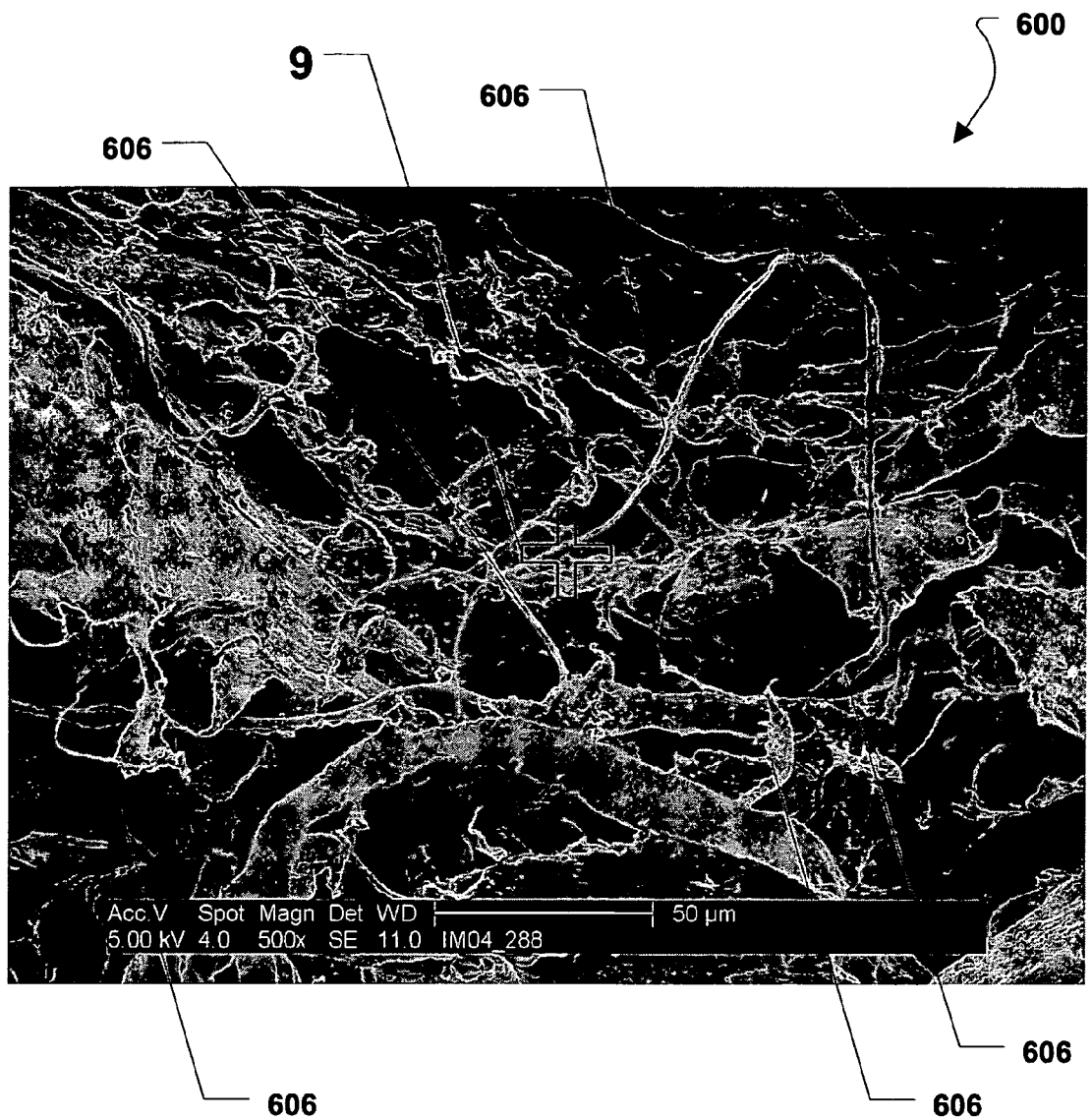
FIG. 8 is an SEM image of the sample of coated collagen material taken at a magnification of five hundred times (500×)
Figure 9:
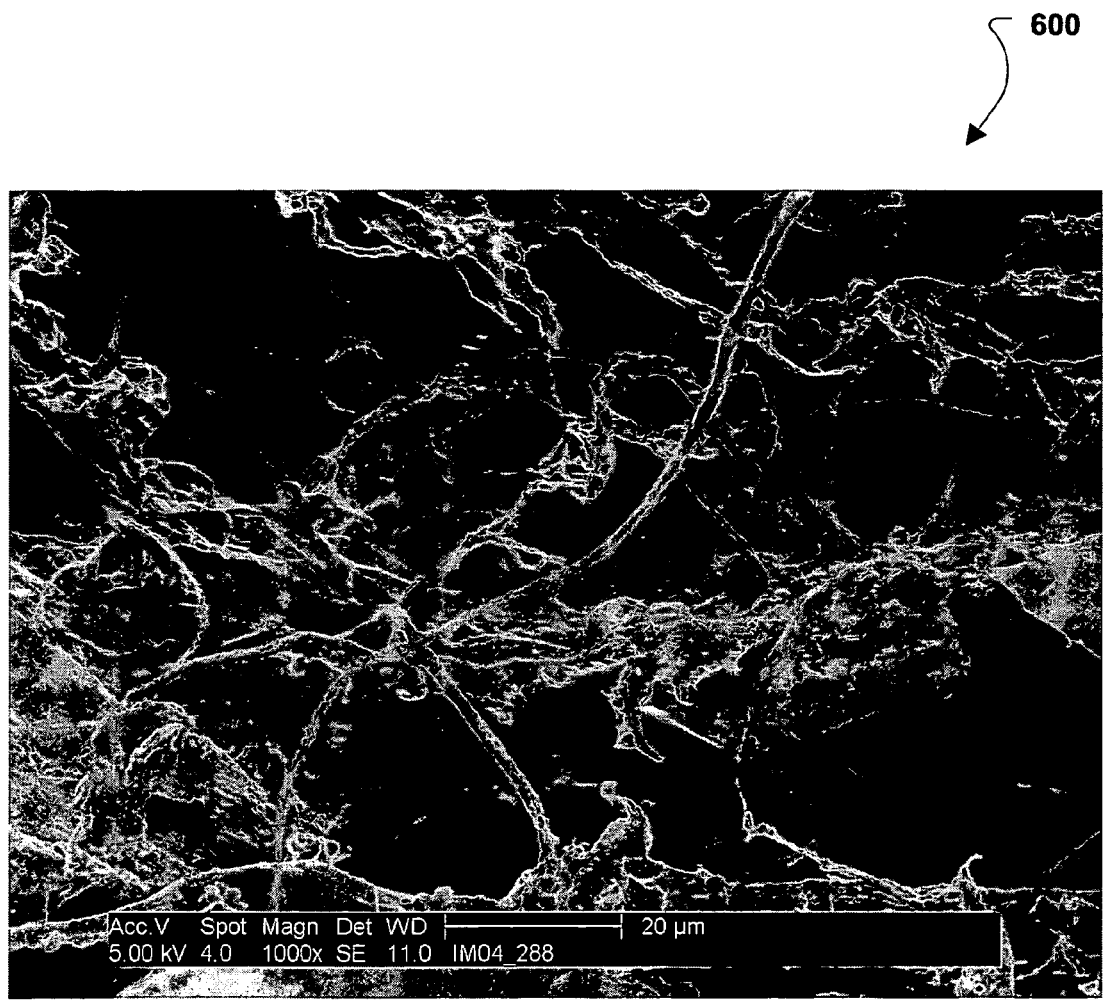
FIG. 9 is an SEM image of the sample of coated collagen material taken at a magnification of one thousand times (1000×)

FIG. 6 through FIG. 9 are various scanning electron microscope (SEM) images of a sample of a coated collagen material. In a particular embodiment, the collagen material is coated with a very thin layer of gold prior to imaging in order to facilitate imaging of the collagen material. FIG. 6 is an SEM image of the coated collagen material taken at a magnification of fifty times (50×). FIG. 7 is an SEM image of the coated collagen material taken at a magnification of one hundred and fifty times (150×). FIG. 7 is centered approximately near the center of cross 7 in FIG. 6. Further, FIG. 8 is an SEM image of the coated collagen material taken at a magnification of five hundred times (500×). FIG. 8 is centered approximately near the center of cross 8 in FIG. 7. FIG. 9 is an SEM image of the coated collagen material taken at a magnification of one thousand times (1000×). FIG. 9 is centered approximately near the center of cross 9 in FIG. 8.

FIG. 6 through FIG. 9 show that the collagen material, generally designated 600, can include a plurality of particles 602. In a particular embodiment, each particle 602 can include a body 604. The body 604 of each particle can be generally elongated and can be generally thin. Further, the main body 604 of each particle 602 can have arcuate portions and flat portions. Specifically, the main body 604 of each particle can be relatively amorphous.

FIG. 8 and FIG. 9 further show that each particle 602 can include at least one fiber 606 that extends from the main body 604 of each particle 602. The fibers 606 can be hook-shaped, loop-shaped, thread-shaped, ribbon-shaped, or a combination thereof. Further, a group of fibers 606 from one or more particles 602 can have an appearance similar to cotton candy.

The collagen material 600 can be mixed with saline to yield a collagen slurry. Further, the collagen slurry can be a slurry, a gel, or a combination thereof. The collagen slurry can be injected into an intervertebral disc, a synovial joint, or other tissue, as described herein. After injection, the saline can seep out of the injection site, e.g., through an annulus fibrosis when injected into an intervertebral disc, leaving the collagen material 600. Further, the fibers 606 of the particles 602 can engage each other to form a relatively robust matrix of material, as shown in the SEM images herein. For example, hook-shaped shaped fibers can "hook" loop-shaped fibers. Also, ribbon-shaped fibers can become intertwined with other ribbon-shaped fibers.

Figure 10:
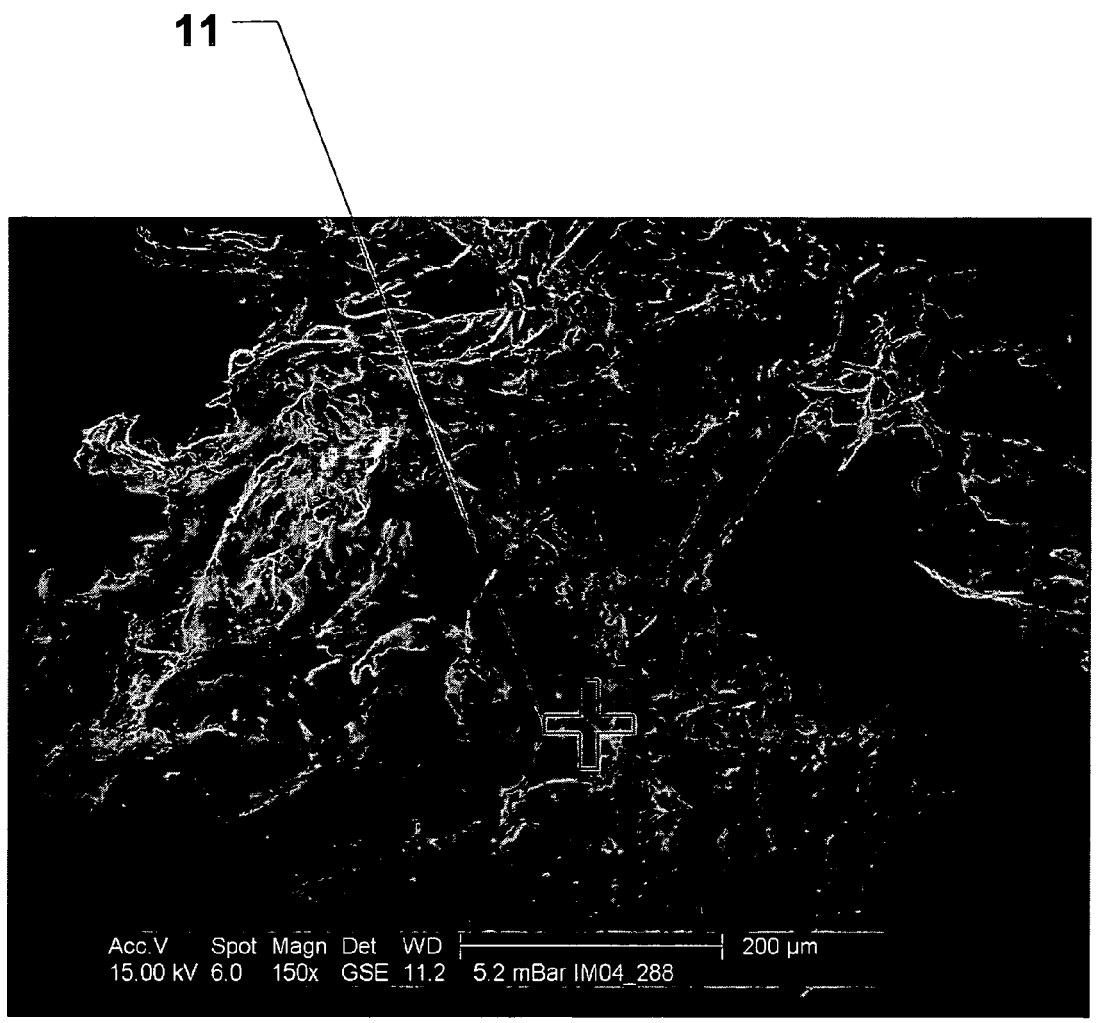
FIG. 10 is an SEM image of a first sample of uncoated collagen material taken at a magnification of one hundred and fifty times (150×)
Figure 11:
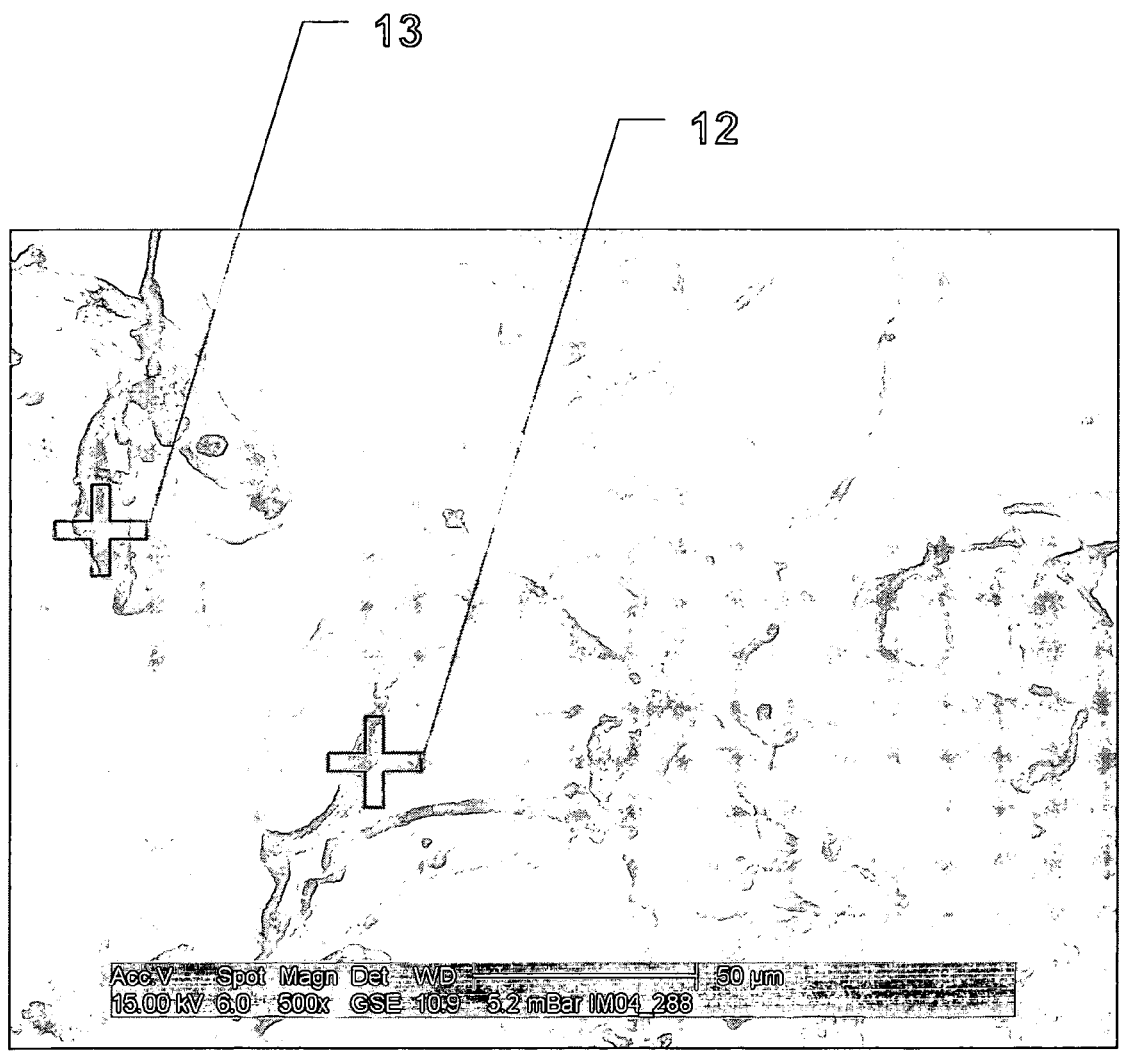
FIG. 11 is an SEM image of the first sample of uncoated collagen material taken at a magnification of five hundred times (500×)
Figure 12:
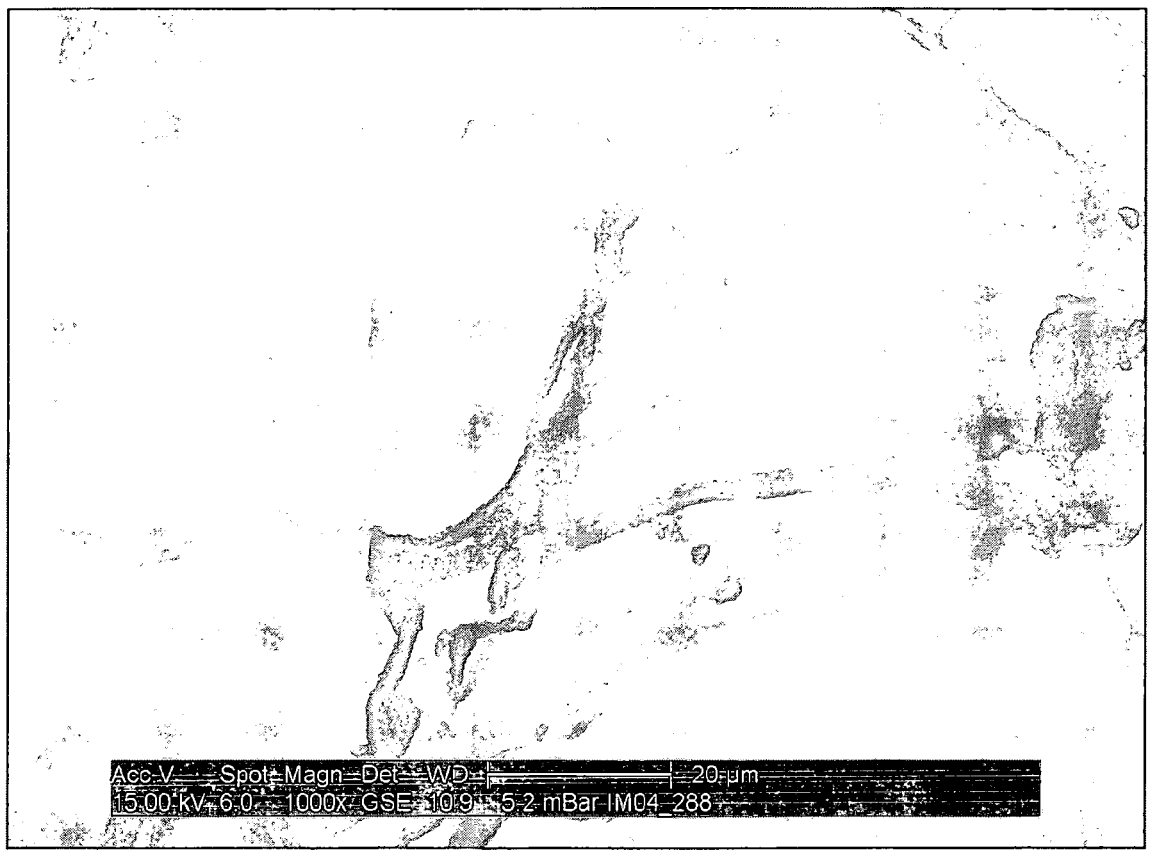
FIG. 12 is an SEM image of the first sample of uncoated collagen material taken at a magnification of one thousand times (1000×)
Figure 13:
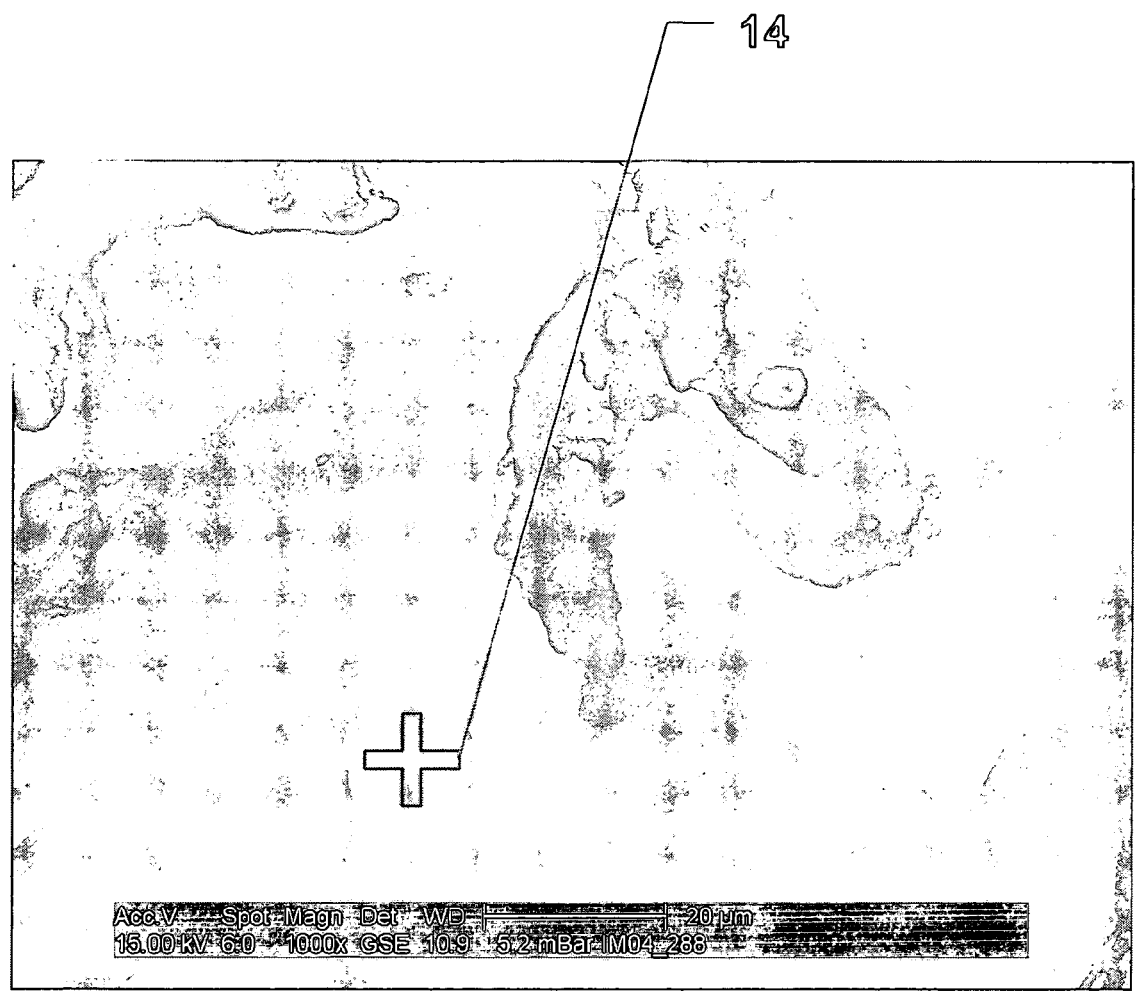
FIG. 13 is another SEM of the first sample of uncoated collagen material taken at a magnification of one thousand times (1000×)
Figure 14:
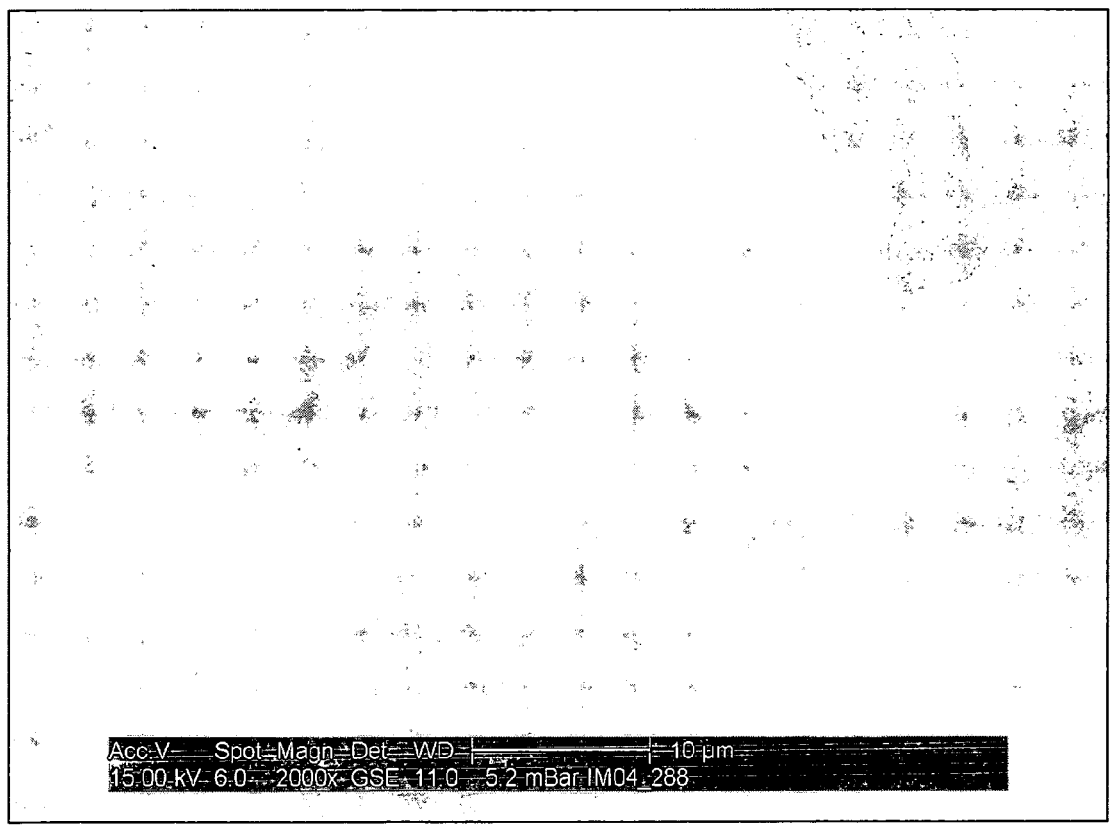
FIG. 14 is an SEM of the first sample of uncoated collagen material taken at a magnification of two thousand times (2000×)

FIG. 10 through FIG. 14 show SEM images of a first sample of uncoated collagen material. FIG. 10 is an SEM image of the uncoated collagen material taken at a magnification of one hundred and fifty times (150×). FIG. 11 is an SEM image of the uncoated collagen material taken at a magnification of five hundred times (500×). FIG. 11 is centered approximately near the center of cross 11 in FIG. 10. FIG. 12 is an SEM image of the uncoated collagen material taken at a magnification of one thousand times (1000×). FIG. 12 is centered approximately near the center of cross 12 in FIG. 11. FIG. 13 is another SEM of the uncoated collagen material taken at a magnification of one thousand times (1000×). FIG. 13 is centered approximately near the center of cross 13 in FIG. 11. FIG. 14 is an SEM of the uncoated collagen material taken at a magnification of two thousand times (2000×). FIG. 14 is centered approximately near the center of cross 14 in FIG. 13. FIG. 10 through FIG. 14 show that the collagen material includes the same elements described in conjunction with FIG. 6 through FIG. 9.

Figure 15:
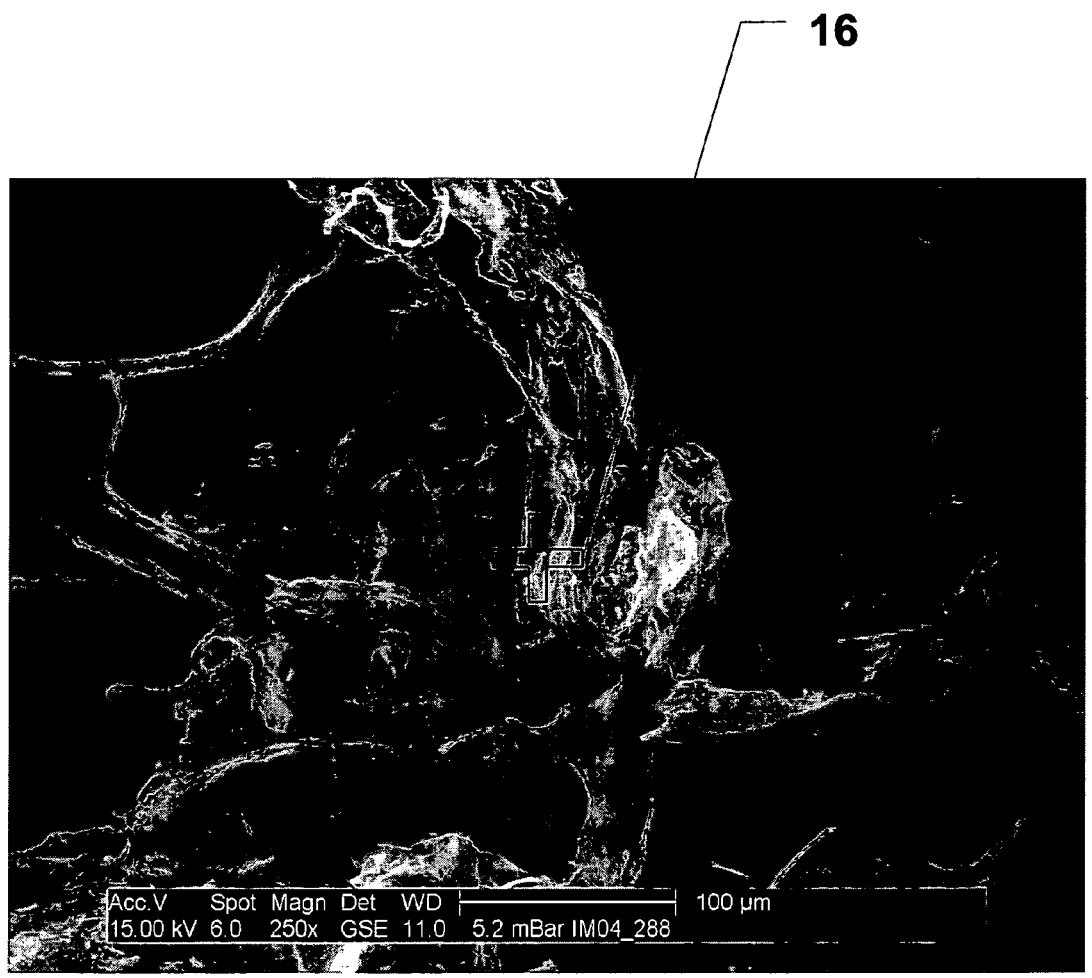
FIG. 15 is an SEM image of a second sample of uncoated collagen material taken at a magnification of two hundred and fifty times (250×)
Figure 16:
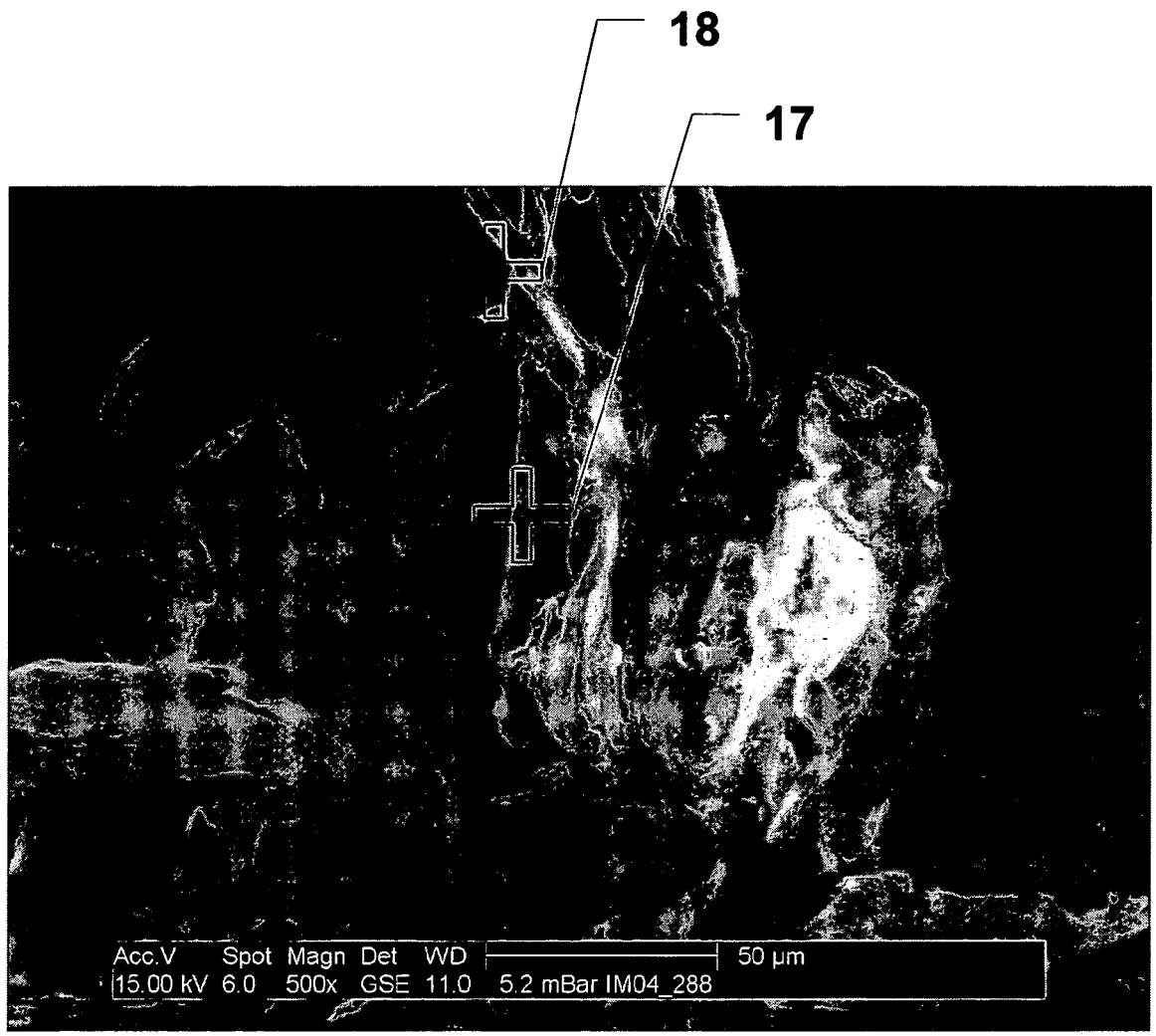
FIG. 16 is an SEM image of the second sample of uncoated collagen material taken at a magnification of five hundred times (500×)
Figure 17:
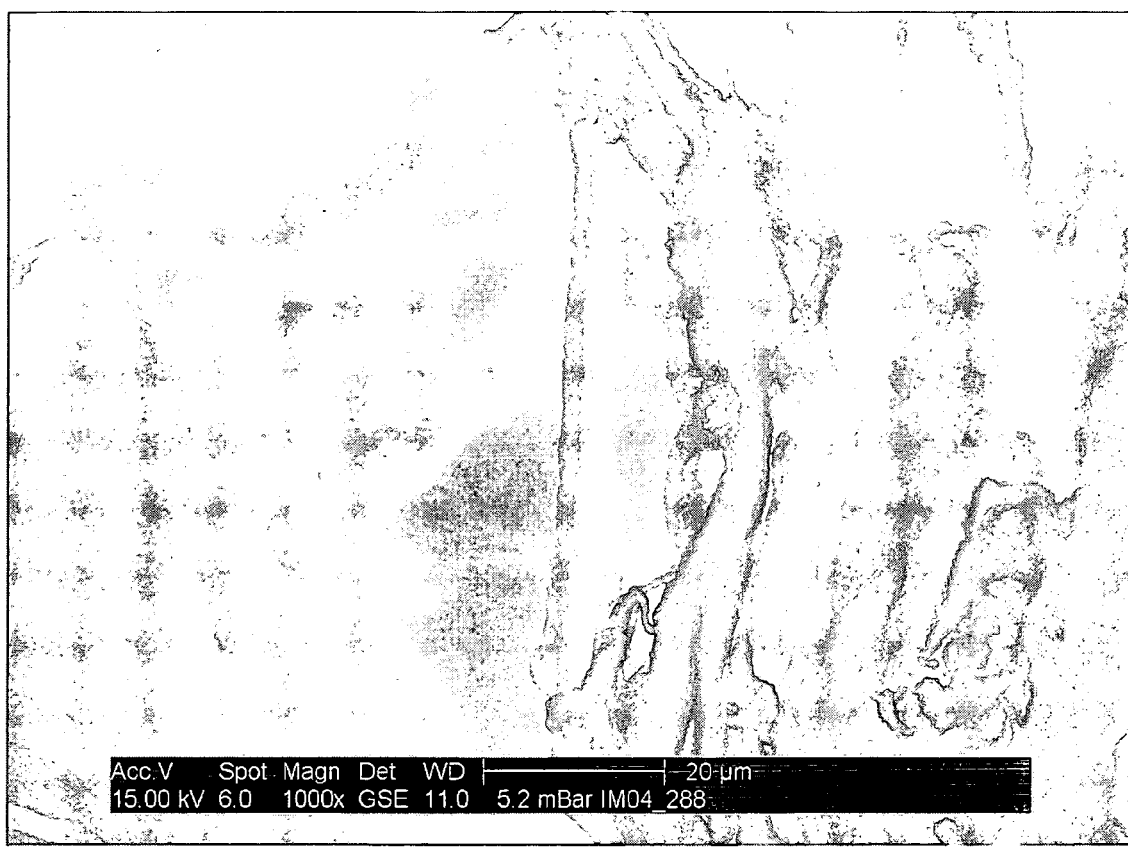
FIG. 17 is an SEM image of the second sample of uncoated collagen material taken at a magnification of one thousand times (1000×)
Figure 18:
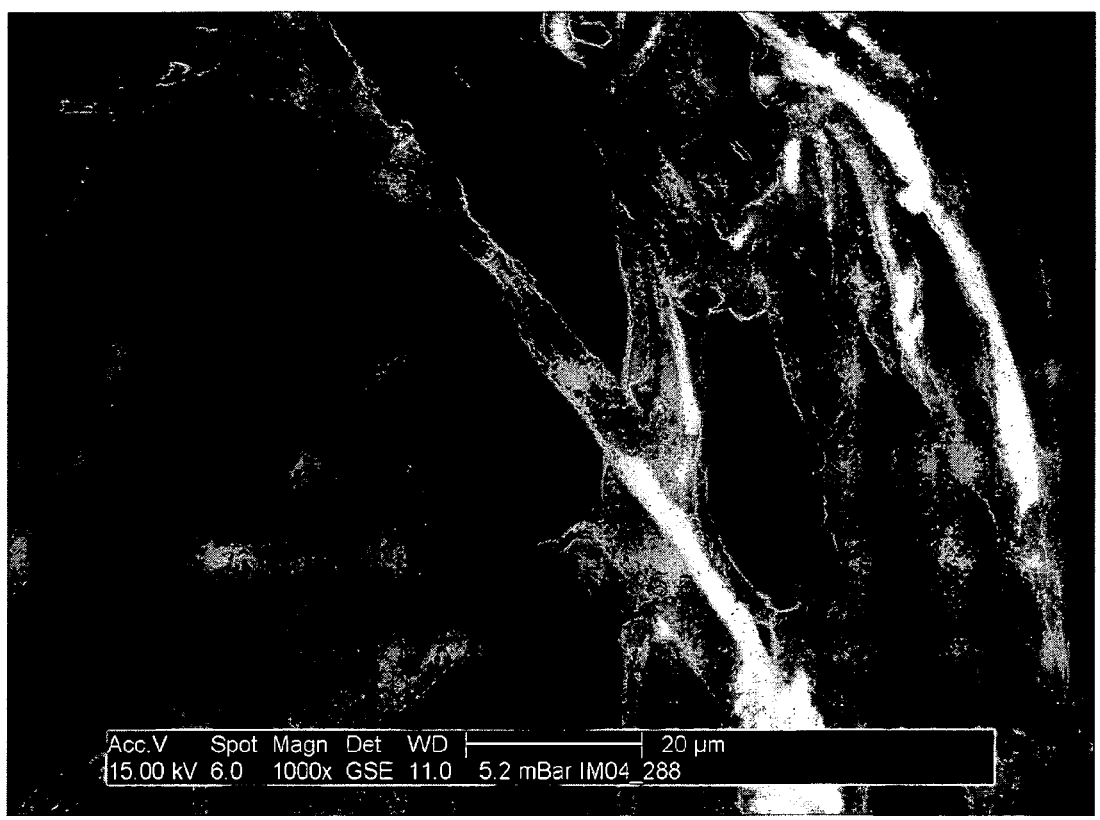
FIG. 18 is another SEM of the second sample of uncoated collagen material taken at a magnification of one thousand times (1000×)

FIG. 15 through FIG. 18 show SEM images of a second sample of uncoated collagen material. FIG. 15 is an SEM image of the uncoated collagen material taken at a magnification of two hundred and fifty times (250×). FIG. 16 is an SEM image of the uncoated collagen material taken at a magnification of five hundred times (500×). FIG. 16 is centered approximately near the center of cross 16 in FIG. 15. FIG. 17 is an SEM image of the uncoated collagen material taken at a magnification of one thousand times (1000×). FIG. 17 is centered approximately near the center of cross 17 in FIG. 16. FIG. 18 is another SEM of the uncoated collagen material taken at a magnification of one thousand times (1000×). FIG. 18 is centered approximately near the center of cross 18 in FIG. 16. FIG. 15 through FIG. 18 show that the collagen material includes the same elements described in conjunction with FIG. 6 through FIG. 9.

In a particular embodiment, the mean size of the particles 602 can be in a range of five-hundredths of a millimeter (0.05 mm) to five millimeters (5.0 mm). In another embodiment, the mean size of the particles 602 can be in a range of twenty-five hundredths of a millimeter (0.25 mm) to one and one-half millimeters (1.5 mm). Further, when dry, the collagen material 600 can have a density in a range of one tenths grams (0.1 g) per cubic centimeter to one gram (1.0 g) per cubic centimeter.

In another embodiment, the collagen material 600 can be mixed with an aqueous solution, such as a saline solution ("saline"), and delivered via a syringe. For example, an amount of collagen material 600 in a range of one-tenth grams to one gram (0.1 g-1.0 g) can be hydrated with an amount of hydrating fluid, or aqueous material in a range of one-tenth cubic centimeters to ten cubic centimeters (0.1 cc-10 cc). Further, an amount of collagen material 600 in a range of two-tenths grams to five-tenths grams (0.2 g-0.5 g) can be hydrated with an amount of hydrating fluid, or aqueous material in a range of two-tenths cubic centimeters to five cubic centimeters (0.2 cc-5 cc). Further, a ratio of hydrating fluid to collagen material 600 can be in a range of one-to-one to one hundred-to-one (1:1-100:1).

In a particular embodiment, three-tenths grams (0.3 g) of the collagen material 600 can be mixed with three cubic centimeters (3.0 cc) of saline, i.e., at a ratio of ten-to-one (10:1), to yield a collagen slurry or a collagen gel. Further, the collagen slurry can be delivered via a syringe having: a ten (10) gauge needle, an eleven (11) gauge needle, a twelve (12) gauge needle, a thirteen (13) gauge needle, a fourteen (14) gauge needle, a fifteen (15) gauge needle, a sixteen (16) gauge needle, a seventeen (17) gauge needle, an eighteen (18) gauge needle, a nineteen (19) gauge needle, a twenty (20) gauge needle, a twenty-one (21) gauge needle, a twenty-two (22)

gauge needle, a twenty-three (23) gauge needle, a twenty-four (24) gauge needle, a twenty-five (25) gauge needle, a twenty-six (26) gauge needle, a twenty-seven (27) gauge needle, a twenty-eight (28) gauge needle, a twenty-nine (29) gauge needle, a thirty (30) gauge needle, a thirty-one (31) gauge needle, a thirty-two (32) gauge needle, a thirty-three (33) gauge needle, or a combination thereof.

Description of a First Method of Manufacturing a Collagen Material

Figure 19:
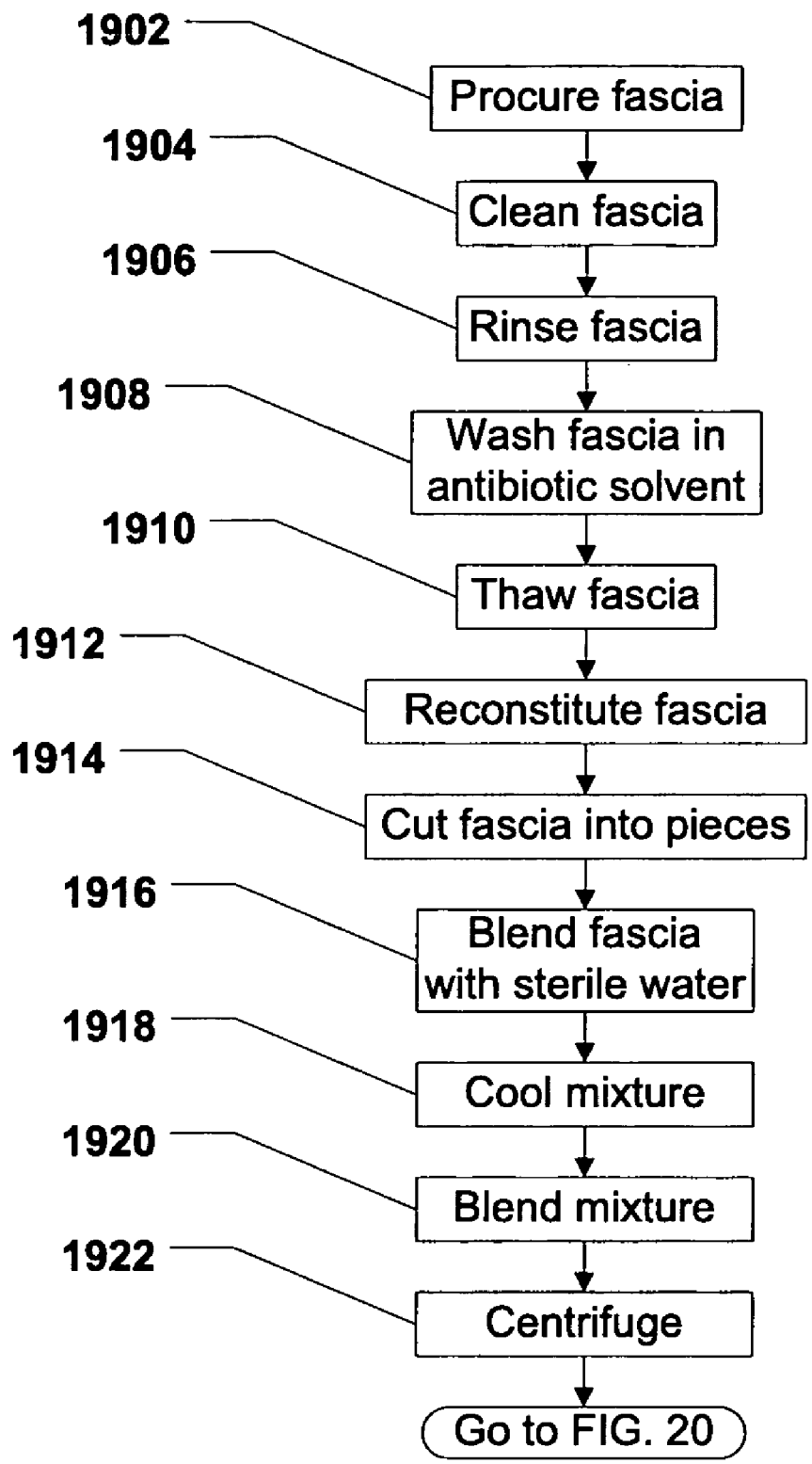
FIG. 19 through FIG. 20 are a flow chart of a first method of manufacturing a collagen material.
Figure 20:
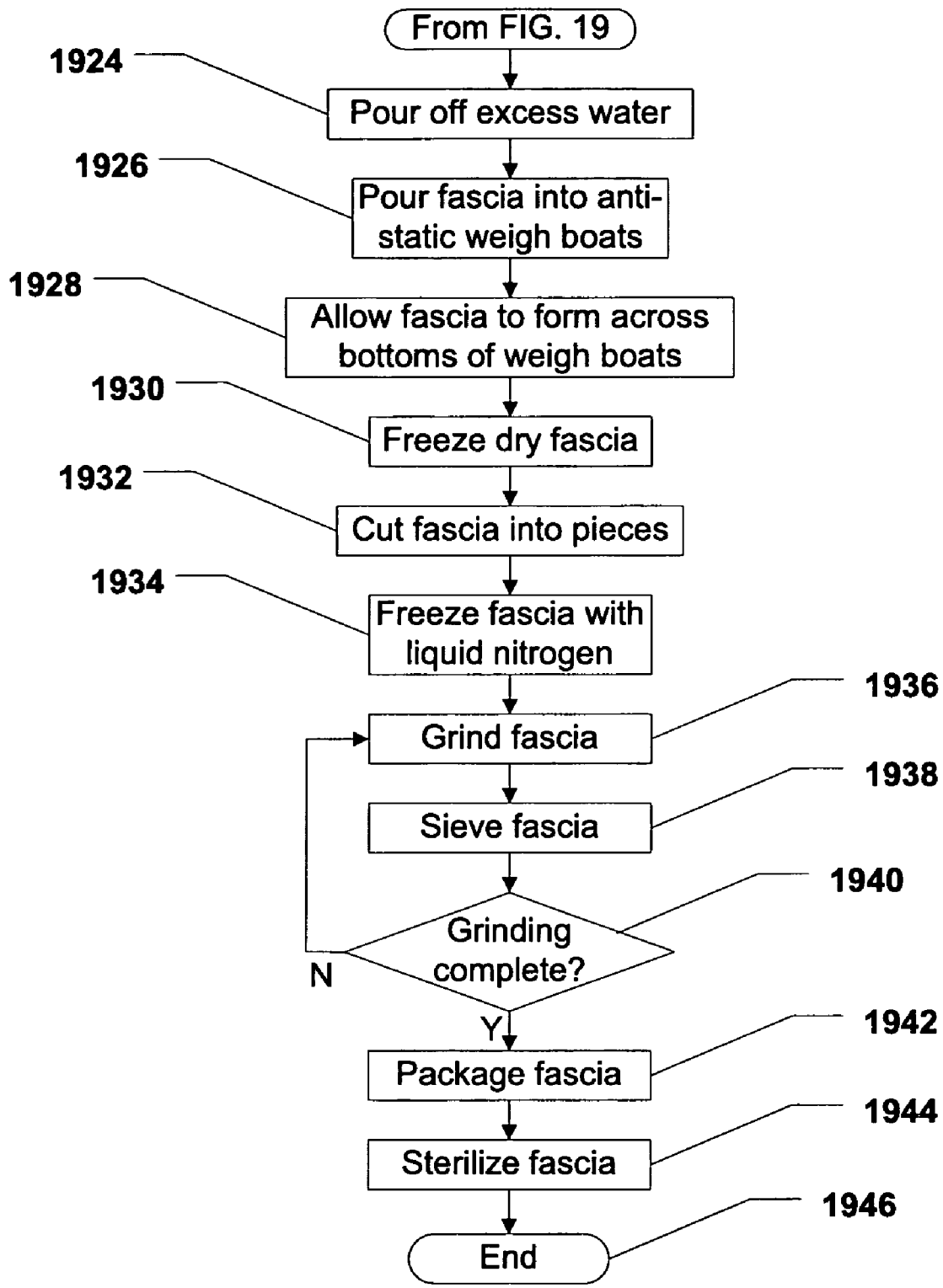

Referring to FIG. 19 and FIG. 20, a first method of manufacturing a collagen material is shown and commences at block 1902. At block 1902, fascia can be procured. In a particular embodiment, the fascia can be dried human fascia. Further, the fascia can be autogenic, allogenic, xenogenic, or a combination thereof.

At block 1904, the fascia can be cleaned. Further, at block 1906, the fascia can be rinsed. At block 1908, the fascia can be washed in an antibiotic solvent. Moving to block 1910, the fascia can be thawed. At block 1912, the fascia can be reconstituted. Also, at block 1914, the fascia can be cut into pieces.

Proceeding to block 1916, the fascia can be blended with sterile water. At block 1918, the fascia mixture can be cooled. Also, at block 1920, the cooled fascia mixture can be blended. At block 1922, the fascia mixture can be centrifuged.

Thereafter, the method proceeds to block 1924, shown in FIG. 20, and the excess water from the centrifuged fascia mixture can be poured off. Continuing to block 1926, the fascia mixture can be poured into one or more anti-static weigh boats. At block 1928, the fascia mixture can be allowed to form across the bottom of each anti-static weigh boat. Moving to block 1930, the fascia mixture can be freeze dried. Thereafter, at block 1932, the freeze dried fascia mixture can be cut into pieces. Further, at block 1934, the fascia material can be frozen using a freezing agent. In a particular embodiment, the freezing agent can be liquid nitrogen.

Proceeding to block 1936, the frozen fascia can be ground. Moreover, at block 1938, the ground fascia can be sieved. Continuing to decision step 1940, it can be determined whether the grinding of the fascia is complete, e.g., whether the ground fascia will adequately pass through the sieve. If the grinding is not complete, the method can return to block 1936 and can continue as described herein. Conversely, if the grinding is complete, the method can continue to block 1942 and the fascia can be packaged for delivery. At block 1944, the packaged fascia can be sterilized. The method then ends at state 1946.

Description of a Second Method of Manufacturing a Collagen Material

Figure 21:
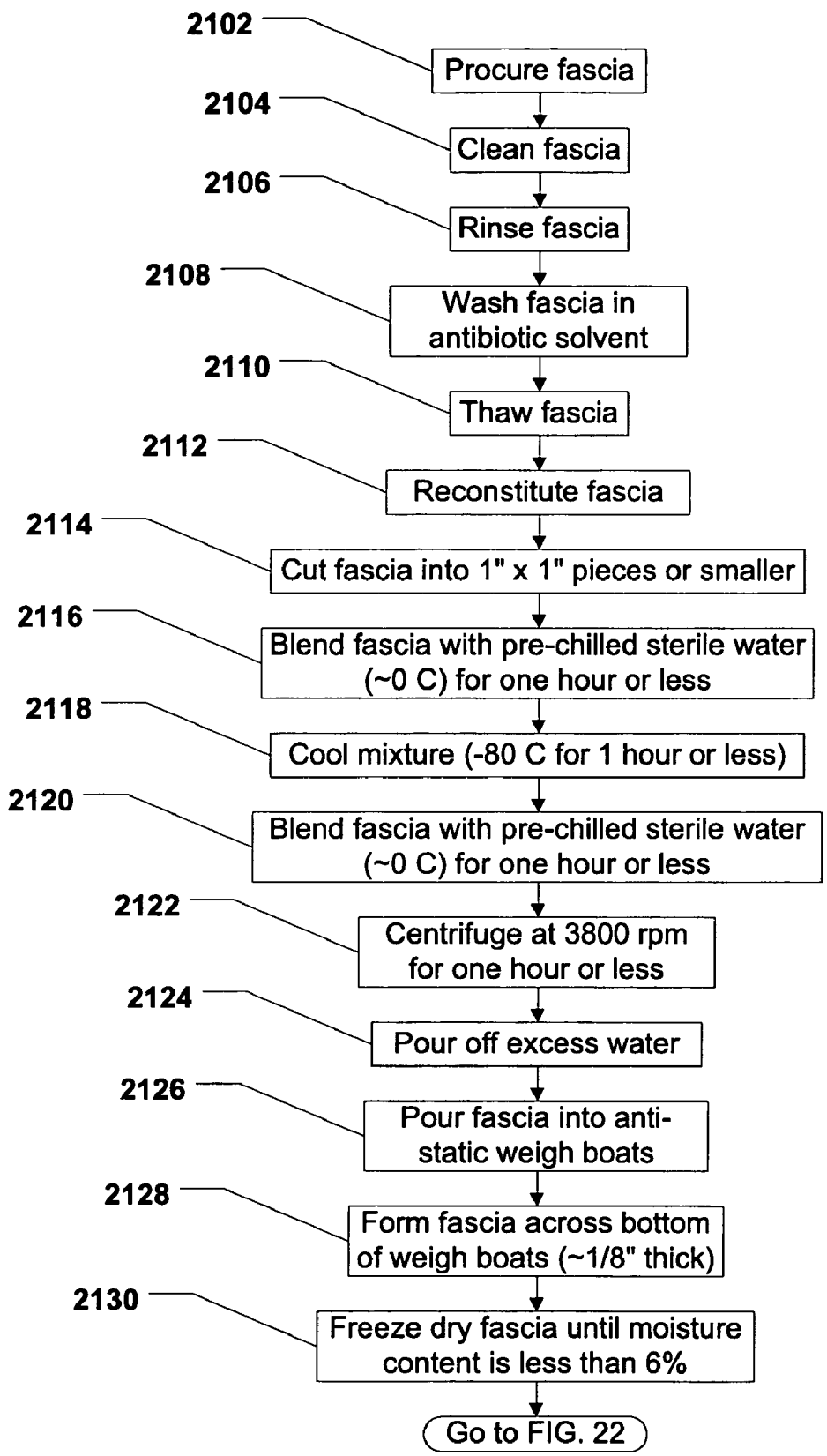
FIG. 21 through FIG. 22 are a flow chart of a second method of manufacturing a collagen material.

Referring now to FIG. 21, a detailed method of manufacturing a collagen material, e.g., the collagen material shown and described herein, is shown and begins at block 2102. At block 2102, fascia can be procured. In a particular embodiment, the fascia can be dried human fascia. Further, the fascia can be autogenic, allogenic, xenogenic, or a combination thereof. Moving to block 2104, the fascia can be cleaned. Further, at block 2106, the fascia can be rinsed. At block 2108, the fascia can be washed in an antibiotic solvent. Proceeding to block 2110, the fascia can be thawed. Also, at block 2112, the thawed fascia can be reconstituted.

Continuing to block 2114, the fascia can be cut into pieces that are less than or equal to one inch by one inch (1"×1"). In another embodiment, the fascia can be cut into pieces that are less than or equal to three-quarters of an inch by three-quarters of an inch (¾"×¾"). In yet another embodiment, the fascia can be cut into pieces that are less than or equal to one-half of an inch by one-half of an inch (½"×½"). In still another embodiment, the fascia can be cut into pieces that are less than or equal to three-eighths of an inch by three-eighths of an inch (⅜"×⅜"). Further, in another embodiment, the fascia can be cut into pieces that are less than or equal to one-quarter of an inch by one-quarter of an inch (¼"×¼"). In another embodiment, the fascia can be cut into pieces that are less than or equal to one-eighth of an inch by one-eighth of an inch (⅛"×⅛").

At block 2116, the fascia can be blended with pre-chilled sterile water for less than or equal to one hour. In another embodiment, the fascia can be blended for less than or equal to forty-five minutes. In yet another embodiment, the fascia can be blended for less than or equal to thirty minutes. In another embodiment, the fascia can be blended for less than or equal to fifteen minutes. In still another embodiment, the fascia can be blended for less than or equal to ten (10) minutes. In another embodiment, the fascia can be blended for approximately seven (7) minutes and thirty (30) seconds. Also, in a particular embodiment, the pre-chilled sterile water can be cooled to approximately zero degrees Celsius (0° C.).

Moving to block 2118, the fascia mixture can be cooled at minus eighty degrees Celsius (−80° C.) for less than or equal to one hour. In another embodiment, the fascia mixture can be cooled for less than or equal to forty-five minutes. In yet another embodiment, the fascia mixture can be cooled for less than or equal to thirty minutes. In another embodiment, the fascia mixture can be cooled for less than or equal to fifteen minutes. In still another embodiment, the fascia mixture can be cooled at minus eighty degrees Celsius (−80° C.) for less than or equal to ten (10) minutes.

At block 2120, once again, the fascia can be blended with pre-chilled sterile water for less than or equal to one hour. In another embodiment, the fascia can be blended for less than or equal to forty-five minutes. In yet another embodiment, the fascia can be blended for less than or equal to thirty minutes. In another embodiment, the fascia can be blended for less than or equal to fifteen minutes. In still another embodiment, the fascia can be blended for less than ten (10) minutes. In another embodiment, the fascia can be blended for approximately seven (7) minutes and thirty (30) seconds. Also, in a particular embodiment, the pre-chilled sterile water can be cooled to approximately zero degrees Celsius (0° C.).

Proceeding to block 2122, the fascia mixture can be centrifuged at approximately four thousand revolutions per minute (4000 rpm) for less than or equal to one hour. In another embodiment, the fascia mixture can be centrifuged for less than or equal to forty-five minutes. In yet another embodiment, the fascia mixture can be centrifuged for less or equal to thirty minutes. In still another embodiment, the fascia mixture can be centrifuged at approximately three thousand eight hundred revolutions per minute (3800 rpm) for less than or equal to twenty (20) minutes. At block 2124, the excess water from the fascia mixture can be poured off.

Moving to block 2126, the fascia mixture can be poured into one or more anti-static weigh boats. At block 2128, the fascia mixture can be formed across the bottom of each weigh boat to a thickness no greater than one quarter of an inch (¼"). Particularly, the fascia mixture can be formed across the bottom of each weigh boat to a thickness of approximately one eight of an inch (⅛"). Thereafter, at block 2130, the fascia mixture is freeze dried until the moisture content of the fascia mixture is less than or approximately equal to ten percent (10%) by weight. In particular, the fascia mixture can be freeze dried until the moisture content of the fascia mixture is less than or equal to six percent (6%) by weight.

Figure 22:
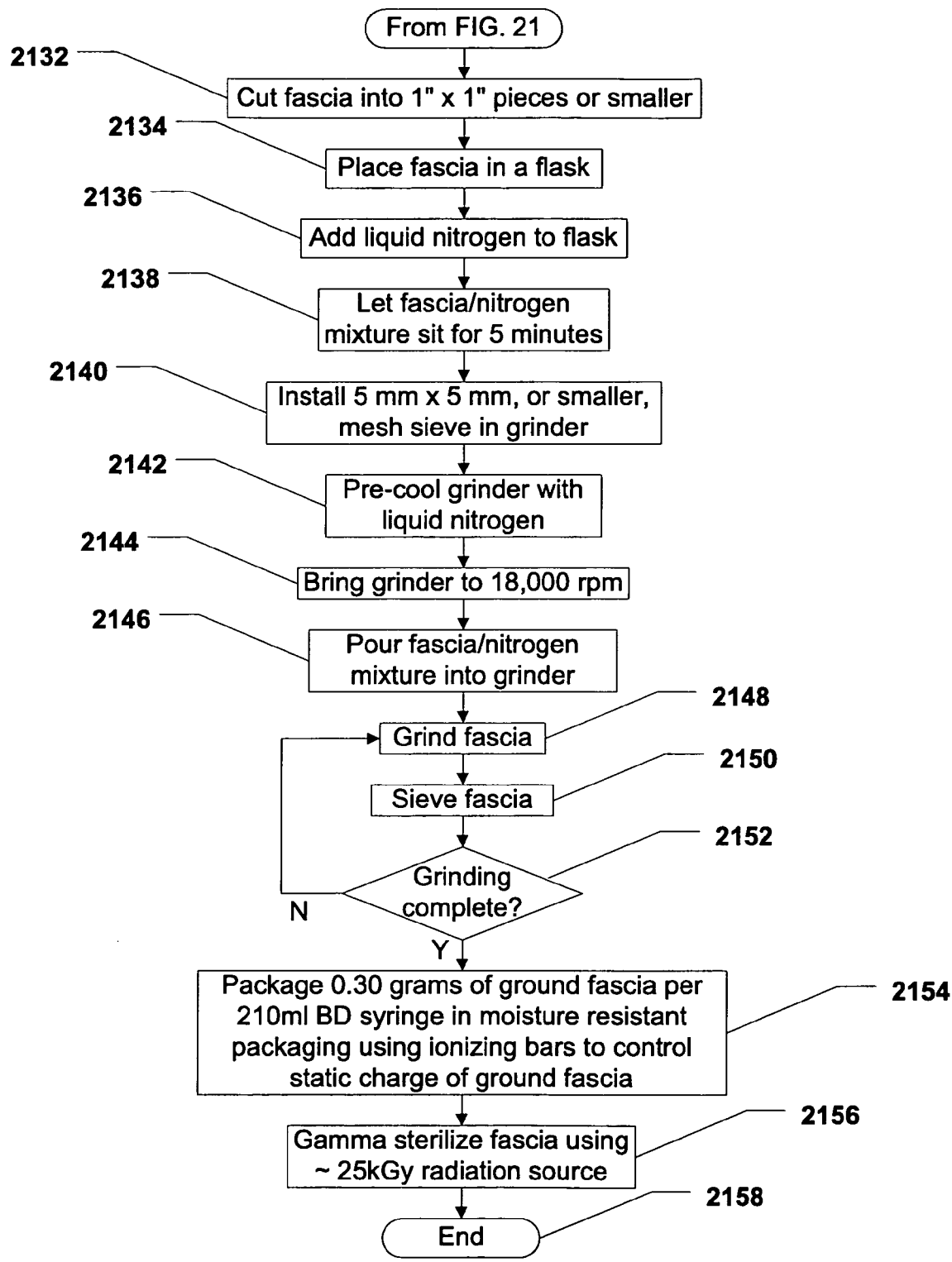

From block 2130, the method proceeds to block 2132, shown in FIG. 22. At block 2132, the freeze dried fascia mixture can be cut into pieces that are less than or equal to one inch by one inch (1"×1"). In another embodiment, the freeze dried fascia can be cut into pieces that are less than or equal to three-quarters of an inch by three-quarters of an inch (¾"× ¾"). In yet another embodiment, the freeze dried fascia can be cut into pieces that are less than or equal to one-half of an inch by one-half of an inch (½"×½"). In still another embodiment, the freeze dried fascia can be cut into pieces that are less than or equal to three-eighths of an inch by three-eighths of an inch (⅜"×⅜"). Further, in another embodiment, the freeze dried fascia can be cut into pieces that are less than or equal to one-quarter of an inch by one-quarter of an inch (¼"×¼"). In another embodiment, the freeze dried fascia can be cut into pieces that are less than or equal to one-eighth of an inch by one-eighth of an inch (⅛"×⅛"). At block 2134, the fascia pieces can be placed in a flask.

Moving to block 2136, a freezing agent, such as liquid nitrogen, can be added to the flask. In a particular embodiment, the freezing agent can be in direct contact with the fascia. Alternatively, the freezing agent can be in indirect contact with the fascia. For example, the fascia can be separated from the freezing agent via a barrier. At block 2138, the fascia/freezing agent mixture, e.g., the fascia/nitrogen mixture, can be allowed to sit undisturbed for ten (10) minutes or less. Particularly, the fascia/nitrogen mixture can be allowed to sit undisturbed for approximately five (5) minutes.

Continuing to block 2140, a sieve can be installed in a grinder. In a particular embodiment, the sieve includes a mesh having a plurality of generally square openings that are less than or equal to five millimeters by five millimeters (5 mm×5 mm). Alternatively, the openings of the sieve can be less than or equal to four millimeters by four millimeters (4 mm×4 mm). In another embodiment, the openings of the sieve can be less than or equal to three millimeters by three millimeters (3 mm×3 mm). In yet another embodiment, the openings of the sieve can be less than or equal to two millimeters by two millimeters (2 mm×2 mm). Further, in still another embodiment, the openings of the sieve can be less than or equal to one and one half millimeters by one and one half millimeters (1.5 mm×1.5 mm).

At block 2142, the grinder can be pre-cooled with liquid nitrogen. Further, at block 2144, the grinder can be brought to a speed of approximately twenty thousand revolutions per minutes (20,000 rpm). In a particular embodiment, the grinder can be brought to a speed of approximately eighteen thousand revolutions per minutes (18,000 rpm). At block 2146, the fascia/nitrogen mixture can be poured into the grinder. Thereafter, at block 2148, the fascia/nitrogen mixture can be ground and at block 2150, the ground fascia can be sieved.

Moving to decision step 2152, it is determined whether the grinding is complete. If not, the method can return to block 2148 and continue as described herein. On the other hand, if the grinding is complete, the method can proceed to block 2154 and the ground fascia can be packaged. For example, approximately three-tenths grams (0.3 g) of ground fascia per 210 ml BD syringe can be packaged in moisture resistant packaging using ionizing bars to control static charge of ground fascia. At block 2156, the fascia can be gamma sterilized using a radiation source having a strength in a range of twenty kilograys to thirty-five kilograys (20-35 kGy). In a particular embodiment, the fascia can be gamma sterilized using a radiation source having a strength of approximately twenty-five kilograys (25 kGy). The method ends at state 2158.

In a particular embodiment, the fascia material may have a moisture content below ten percent (10%). If so, the fascia material can be cooled, e.g., in a deep freezer, so that the temperature of the fascia material falls below a glass transition temperature. Below the glass transition temperature, the fascia material can become rigid or brittle and the rigid fascia material can be ground as described herein. Otherwise, if fascia material has a moisture content above ten percent (10%), the fascia material can be cooled until the moisture freezes and renders the fascia material rigid.

Description of a Third Method of Manufacturing a Collagen Material

Figure 23:
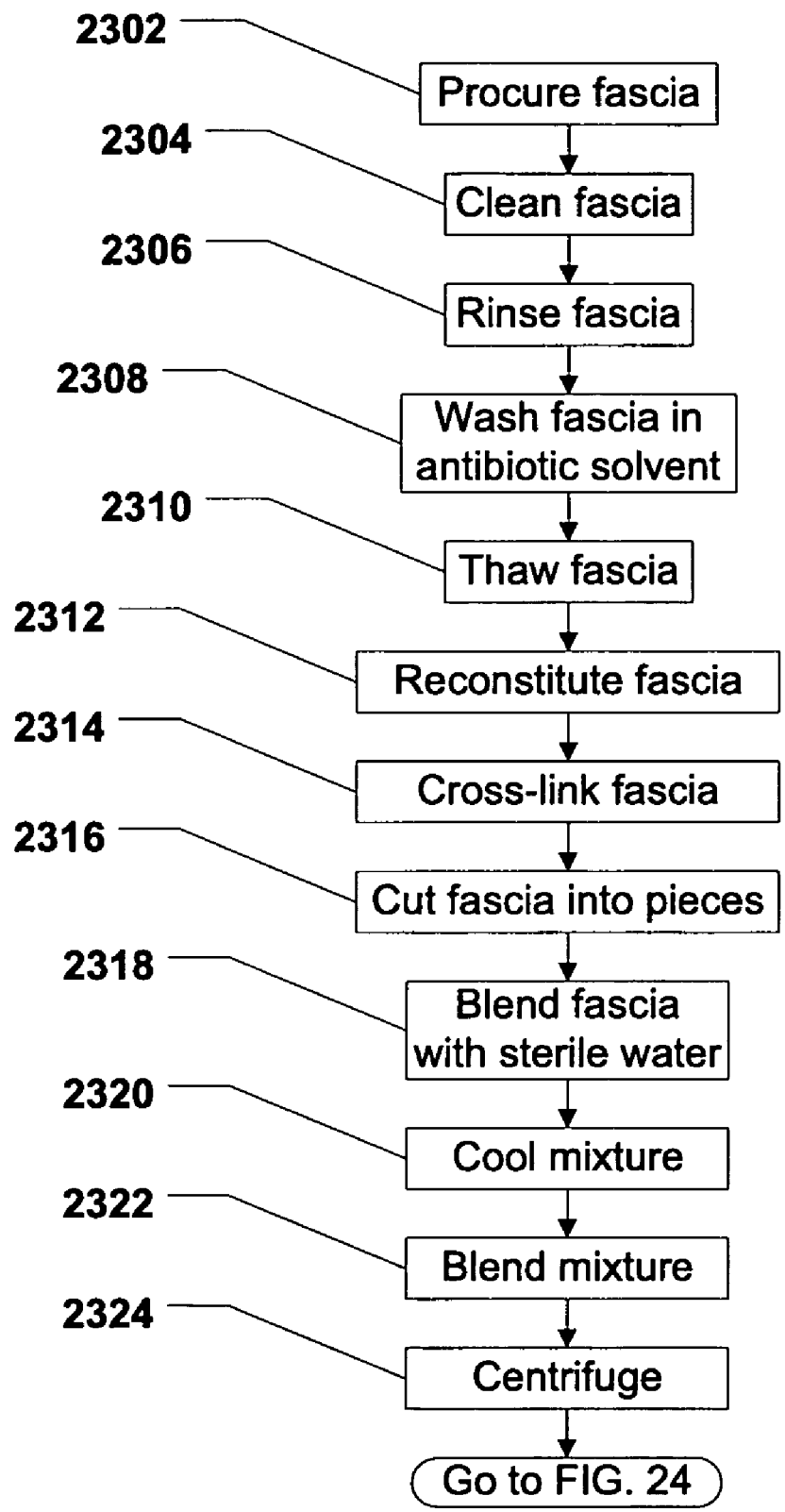
FIG. 23 through FIG. 24 are a flow chart of a third method of manufacturing a collagen material.

Referring to FIG. 23, a third method of manufacturing a collagen material, e.g., the collagen material described herein, is shown and commences at block 2302. At block 2302, fascia can be procured. In a particular embodiment, the fascia can be dried human fascia. Further, the fascia can be autogenic, allogenic, xenogenic, or a combination thereof.

At block 2304, the fascia can be cleaned. Further, at block 2306, the fascia can be rinsed. At block 2308, the fascia can be washed in an antibiotic solvent. Moving to block 2310, the fascia can be thawed. At block 2312, the fascia can be reconstituted. At block 2314, the reconstituted fascia can be cross-linked. In a particular embodiment, the reconstituted fascia can be cross-linked using a cross-linking agent. In a particular embodiment, the cross-linking agent can be glutaraldehyde, genipin, or a combination thereof. Further, the cross-linking agent can be another protein cross-linking agent. Also, at block 2316, the cross-linked fascia can be cut into pieces.

Proceeding to block 2318, the cross-linked fascia can be blended with sterile water. At block 2320, the fascia mixture can be cooled. Also, at block 2322, the cooled fascia mixture can be blended. At block 2324, the fascia mixture can be centrifuged.

Figure 24:
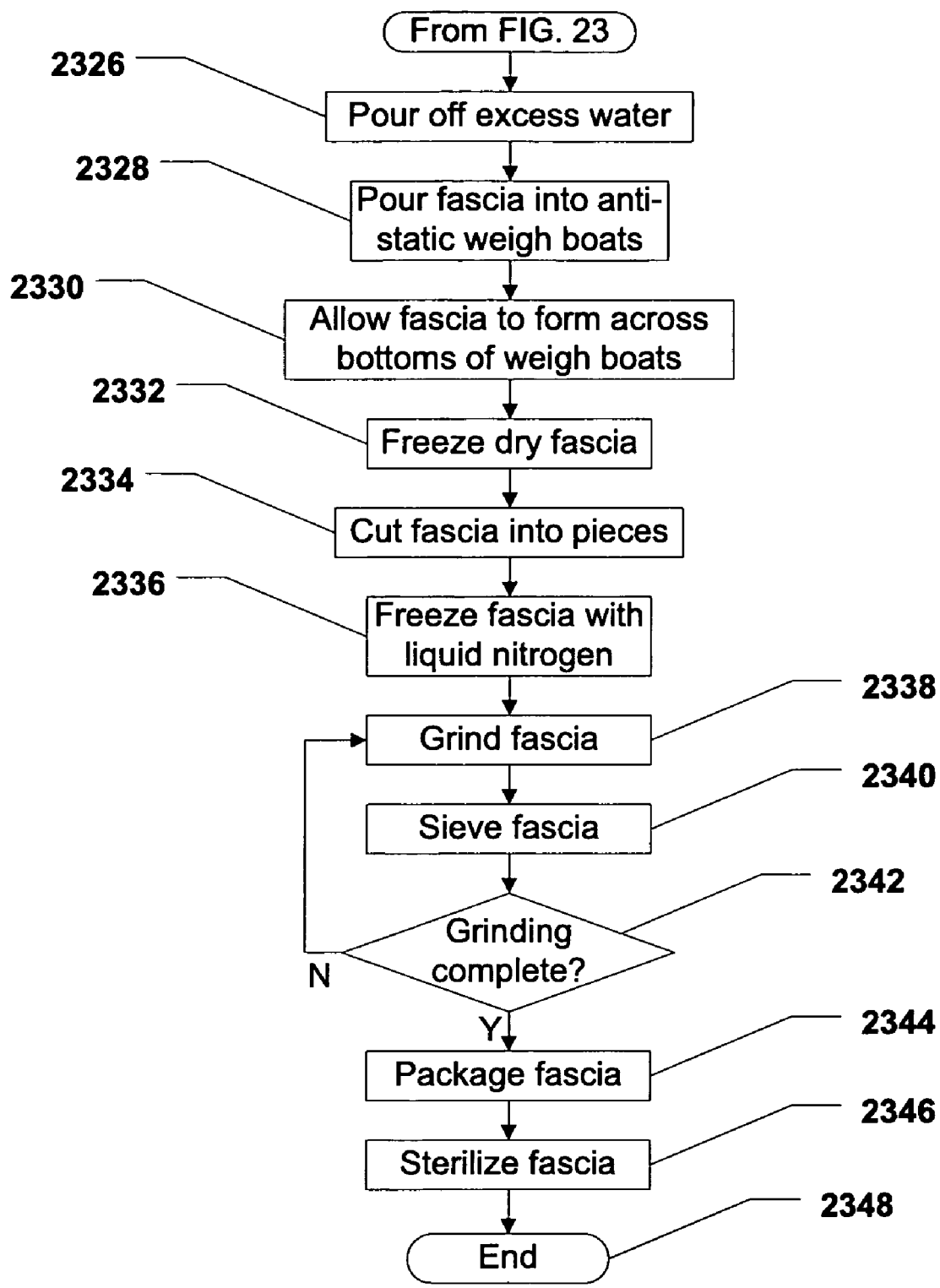

Thereafter, the method proceeds to block 2326, shown in FIG. 24, and the excess water from the centrifuged fascia mixture can be poured off. Continuing to block 2328, the fascia mixture can be poured into one or more anti-static weigh boats. At block 2330, the fascia mixture can be allowed to form across the bottom of each anti-static weigh boat. Moving to block 2332, the fascia mixture can be freeze dried. Thereafter, at block 2334, the freeze dried fascia mixture can be cut into pieces. Further, at block 2336, the fascia material can be frozen, e.g., using liquid nitrogen.

Proceeding to block 2338, the frozen fascia can be ground. Moreover, at block 2340, the ground fascia can be sieved. Continuing to decision step 2342, it can be determined whether the grinding of the fascia is complete. If the grinding is not complete, the method can return to block 2338 and can continue as described herein. Conversely, if the grinding is complete, the method can continue to block 2344 and the fascia can be packaged for delivery. At block 2346, the packaged fascia can be sterilized. The method then ends at state 2348.

Description of a Fourth Method of Manufacturing a Collagen Material

Figure 25:
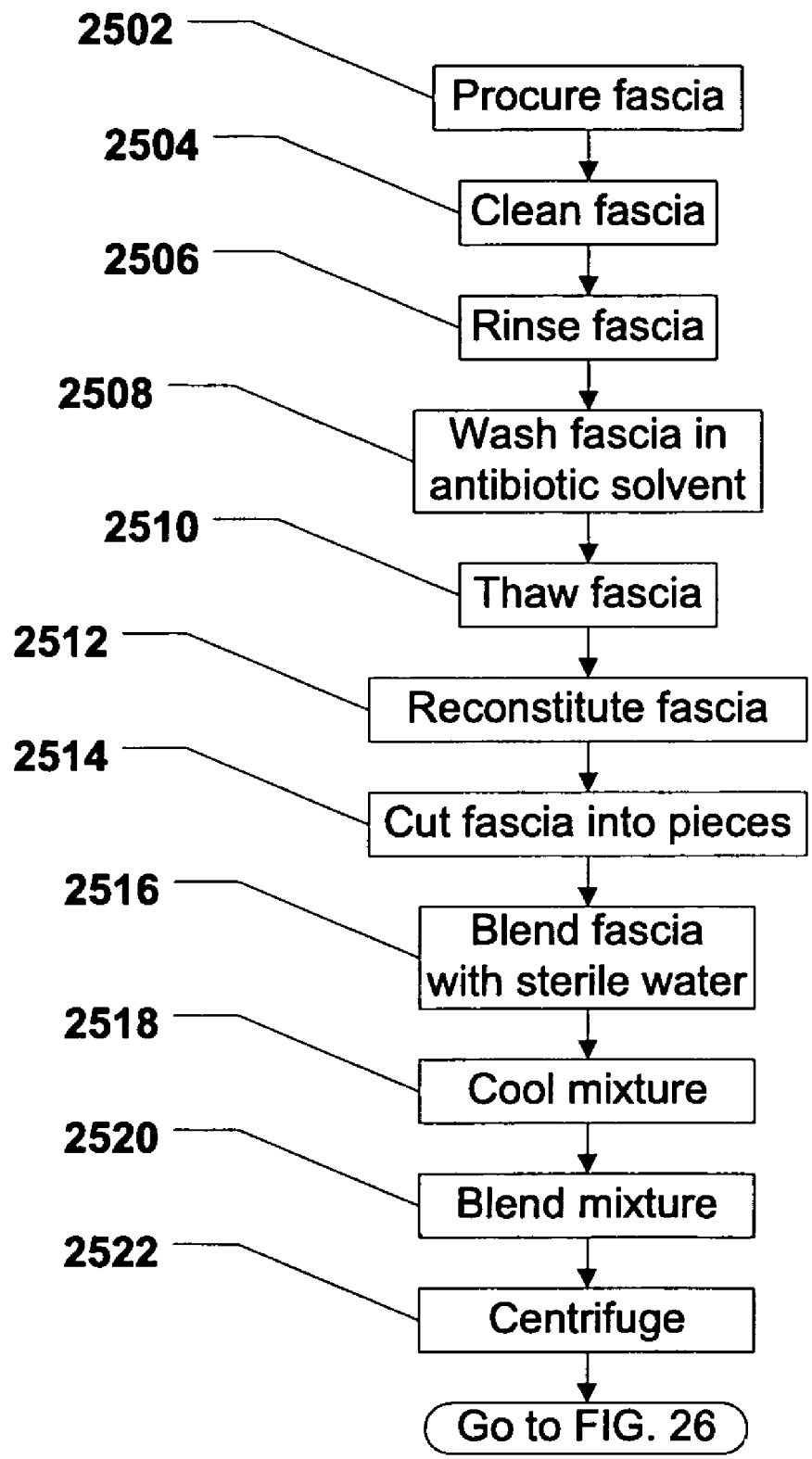
FIG. 25 through FIG. 26 are a flow chart of a fourth method of manufacturing a collagen material.

Referring to FIG. 25, a method of manufacturing a collagen material, e.g., the collagen material described herein, is shown and commences at block 2502. At block 2502, fascia can be procured. In a particular embodiment, the fascia can be dried human fascia. Further, the fascia can be autogenic, allogenic, xenogenic, or a combination thereof.

At block 2504, the fascia can be cleaned. Further, at block 2506, the fascia can be rinsed. At block 2508, the fascia can be washed in an antibiotic solvent. Moving to block 2510, the fascia can be thawed. At block 2512, the fascia can be reconstituted. Also, at block 2514, the fascia can be cut into pieces.

Proceeding to block 2516, the fascia can be blended with sterile water. At block 2518, the fascia mixture can be cooled.

Also, at block 2520, the cooled fascia mixture can be blended. At block 2522, the fascia mixture can be centrifuged.

Figure 26:
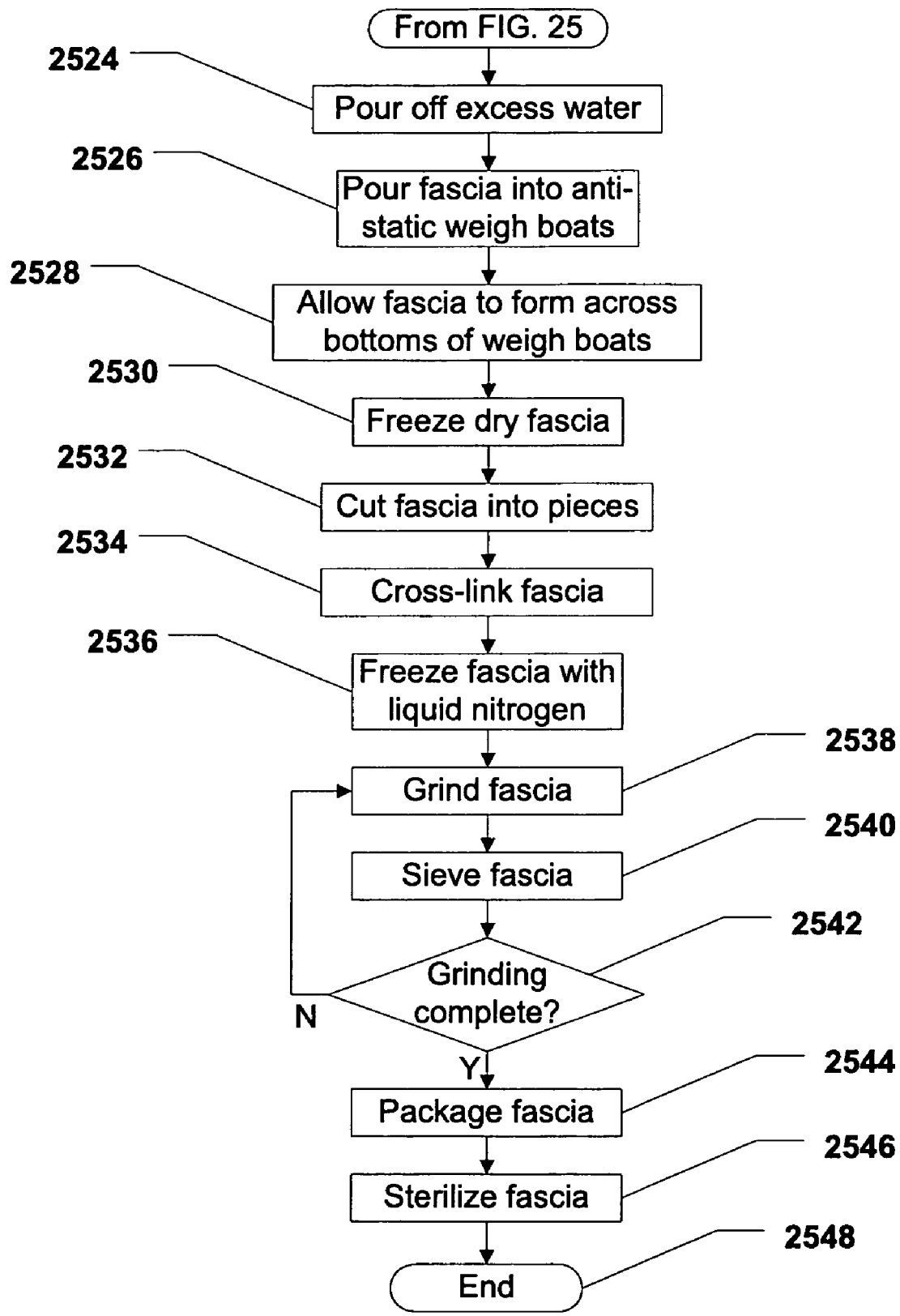

Thereafter, the method proceeds to block 2524, shown in FIG. 26, and the excess water from the centrifuged fascia mixture can be poured off. Continuing to block 2526, the fascia mixture can be poured into one or more anti-static weigh boats. At block 2528, the fascia mixture can be allowed to form across the bottom of each anti-static weigh boat. Moving to block 2530, the fascia mixture can be freeze dried. Thereafter, at block 2532, the freeze dried fascia mixture can be cut into pieces. At block 2532, the fascia material can be cross-linked. In a particular embodiment, the fascia material can be cross-linked using a cross-linking agent. In a particular embodiment, the cross-linking agent can be glutaraldehyde, genipin, or a combination thereof. Further, the cross-linking agent can be another protein cross-linking agent. Further, at block 2536, the cross-linked fascia material can be frozen, e.g., using liquid nitrogen.

Proceeding to block 2538, the frozen, cross-linked fascia can be ground. Moreover, at block 2540, the ground fascia can be sieved. Continuing to decision step 2542, it can be determined whether the grinding of the fascia is complete. If the grinding is not complete, the method can return to block 2538 and can continue as described herein. Conversely, if the grinding is complete, the method can continue to block 2544 and the fascia can be packaged for delivery. At block 2546, the packaged fascia can be sterilized. The method then ends at state 2548.

Description of a First Method of Treating an Intervertebral Disc

Figure 27:
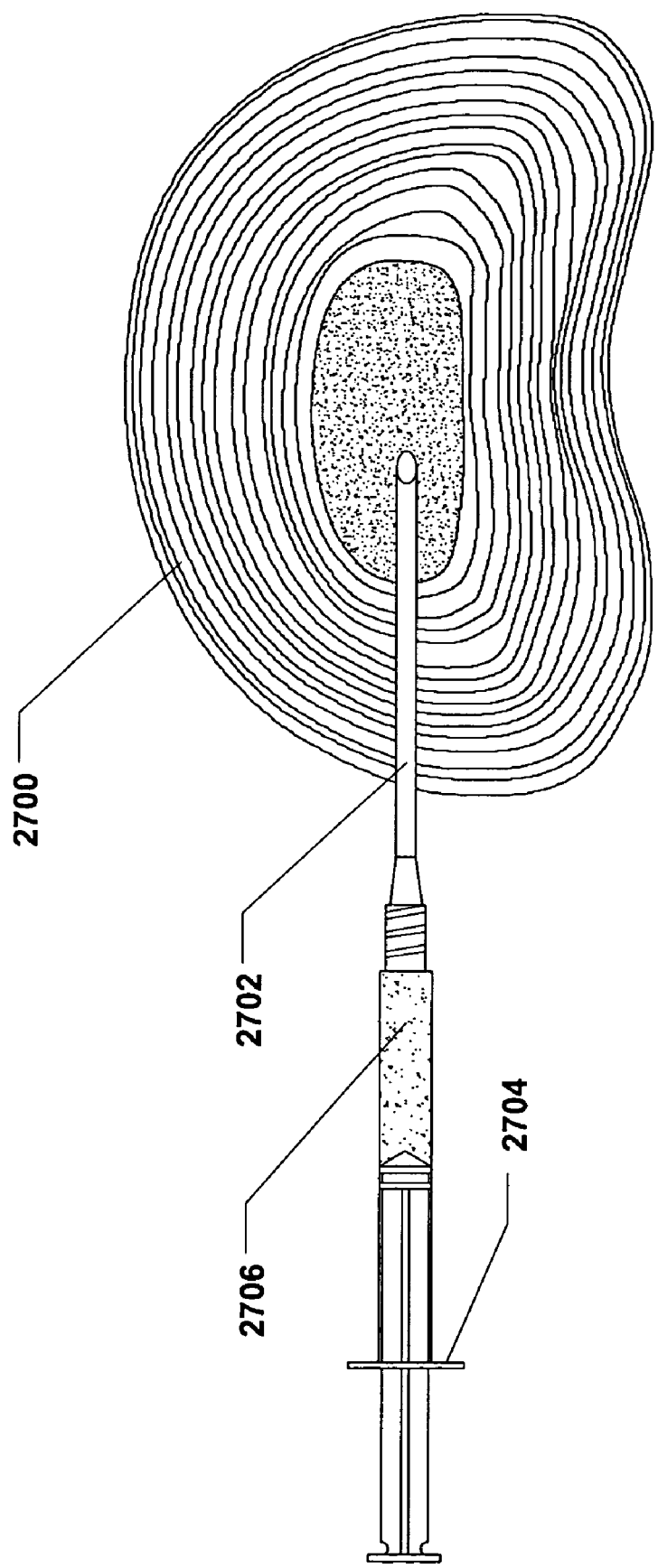
FIG. 27 is a cross-section view of an intervertebral disc with a collagen material injected therein.

FIG. 27 illustrates an intervertebral disc, designated 2700. As shown, a needle 2702 can be inserted into the intervertebral disc 2700. The needle 2702 can extend from a syringe 2704 that can be filled with a collagen material 2706, e.g., a collagen material described herein. The collagen material 2706 can be injected into the intervertebral disc 2700 in order to augment or bulk up the intervertebral disc 2700 and minimize shrinkage of the intervertebral disc 2700 due to degeneration or trauma.

Figure 28:
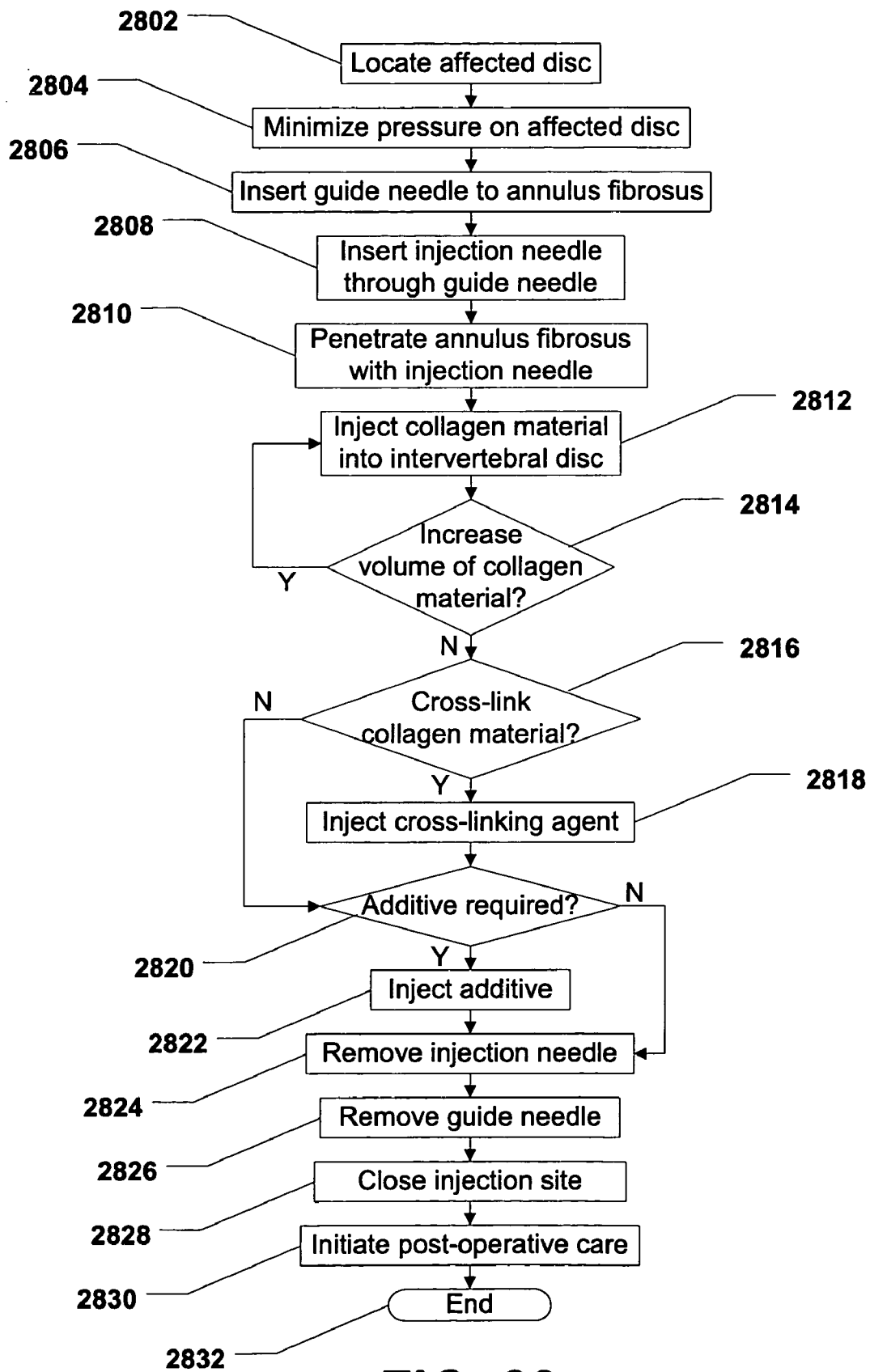
FIG. 28 is a flow chart of a first method of treating an intervertebral disc.

Referring to FIG. 28, a first method of treating an intervertebral disc is illustrated and commences at block 2802. At block 2802, the affected intervertebral disc can be located. At block 2804, the pressure on the intervertebral disc can be reduced. The pressure on the intervertebral disc can be reduced by placing the patient in a position that reduces loading in the area near the vertebra immediately surrounding the intervertebral disc. For example, the patient can be placed in a prone position on a flexible, or hinged, surgical table and the patient's spine can be slightly bent by flexing or bending the flexible surgical table around one or more hinges. Further, the patient can be placed in traction in order to reduce pressure on the intervertebral disc. In a particular embodiment, reducing pressure on the intervertebral disc can maximize the amount of collagen material injected therein.

Moving to block 2806, a guide needle can be inserted to the annulus fibrosus of the affected intervertebral disc. In a particular embodiment, the guide needle can be inserted such that the tip of the guide needle is immediately adjacent to the annulus fibrosus, but does not pierce the annulus fibrosus. At block 2808, an injection needle can be inserted through the guide needle. Further, at block 2810, the annulus fibrosus can be penetrated with the injection needle. In a particular embodiment, the injection needle can be inserted into the annulus fibrosus such that the tip of the injection needle is approximately near the center of the annulus fibrosus. The location of the tip of the guide needle or the location of tip of the injection needle can be verified using imaging technology, e.g., fluoroscopy, magnetic resonance imaging, computed tomography, or any other similar technology well known in the art.

Proceeding to block 2812, collagen material can be injected into the intervertebral disc. In a particular embodiment, the collagen material can be the collagen material described herein. Further, the collagen material can be manufactured as described herein. Also, in a particular embodiment, the collagen material can be injected into the nucleus pulposus within the annulus fibrosus. In a particular embodiment, the collagen material can be in the form of a collagen slurry, i.e., collagen material mixed with saline.

Continuing to decision step 2814, it can be determined whether to increase the volume of collagen material within the nucleus pulposus. This determination can be facilitated using a radio contrast agent injected with the collagen material and imaging technology, e.g., fluoroscopy, magnetic resonance imaging, computed tomography or some other imaging technology well know in the art. At decision step 2814, if it is determined to increase the volume of collagen material, the method can return to block 2812 and more collagen can be injected into the intervertebral disc. Thereafter, the method can continue as described herein. Conversely, if it is determined not to increase the volume of collagen material, the method can proceed to decision step 2816 and it can be determined whether to cross-link the collagen material. If so, the method proceeds to block 2818 and a cross-linking agent can be injected into the intervertebral disc. In a particular embodiment, the cross-linking agent can be glutaraldehyde, genipin, or a combination thereof. Further, the cross-linking agent can be another protein cross-linking agent. Cross-linking the collagen material can result in a more robust material within the intervertebral disc. From block 2818, the method can proceed to decision step 2820.

Returning to decision step 2816, if it is determined not to cross-link the collagen material, the method can also proceed to decision step 2820. At decision step 2820, it can be determined whether to inject an additive. If it is determined to inject an additive, the method can proceed to block 2822 and an additive can be injected. For example, the additives can include radiocontrast media, drugs, cellular matters, biological factors, or a combination thereof. In a particular embodiment, the drugs can include antibiotics, analgesics, anti-inflammatory drugs, anti-TNF-alpha, steroids, or a combination thereof. Further, the cellular matters can include bone marrow derived stem cells, lipo derived stem cells, or a combination thereof. Also, the biological factor can include bone morphogenetic protein (BMP), cartilage-derived morphogenetic protein (CDMP), platelet derived growth factor (PDGF), insulin-like growth factor (IGF), LIM mineralization protein, fibroblast growth factor (FGF), osteoblast growth factor, or a combination thereof. The additives can also include additives to promote slurry or gel formation. These additives may promote protein folding, water binding, protein-to-protein interaction, water immobilization, or a combination thereof. Additionally, the additives can include polysaccharides such as, proteoglycans, hyaluronic acid, or combination thereof, which can attract or bind water to increase hydration of the intervertebral disc. From block 2822, the method can proceed to block 2824.

Returning to decision step 2820, if it is determined not to inject an additive, the method can also proceed to block 2824. At block 2824, the injection needle can be removed from the patient. Further, at block 2826, the guide needle can be removed from the patient. Moving to block 2828, the injection site can be closed. In a particular embodiment, the injection site can simply be allowed to close due to the elasticity of the patients skin. Alternatively, the injection site can be sutured, if necessary. Proceeding to block 2830, post-operative care can be initiated. Then, the method can end at state 2832.

Description of a Second Method of Treating an Intervertebral Disc

Figure 29:
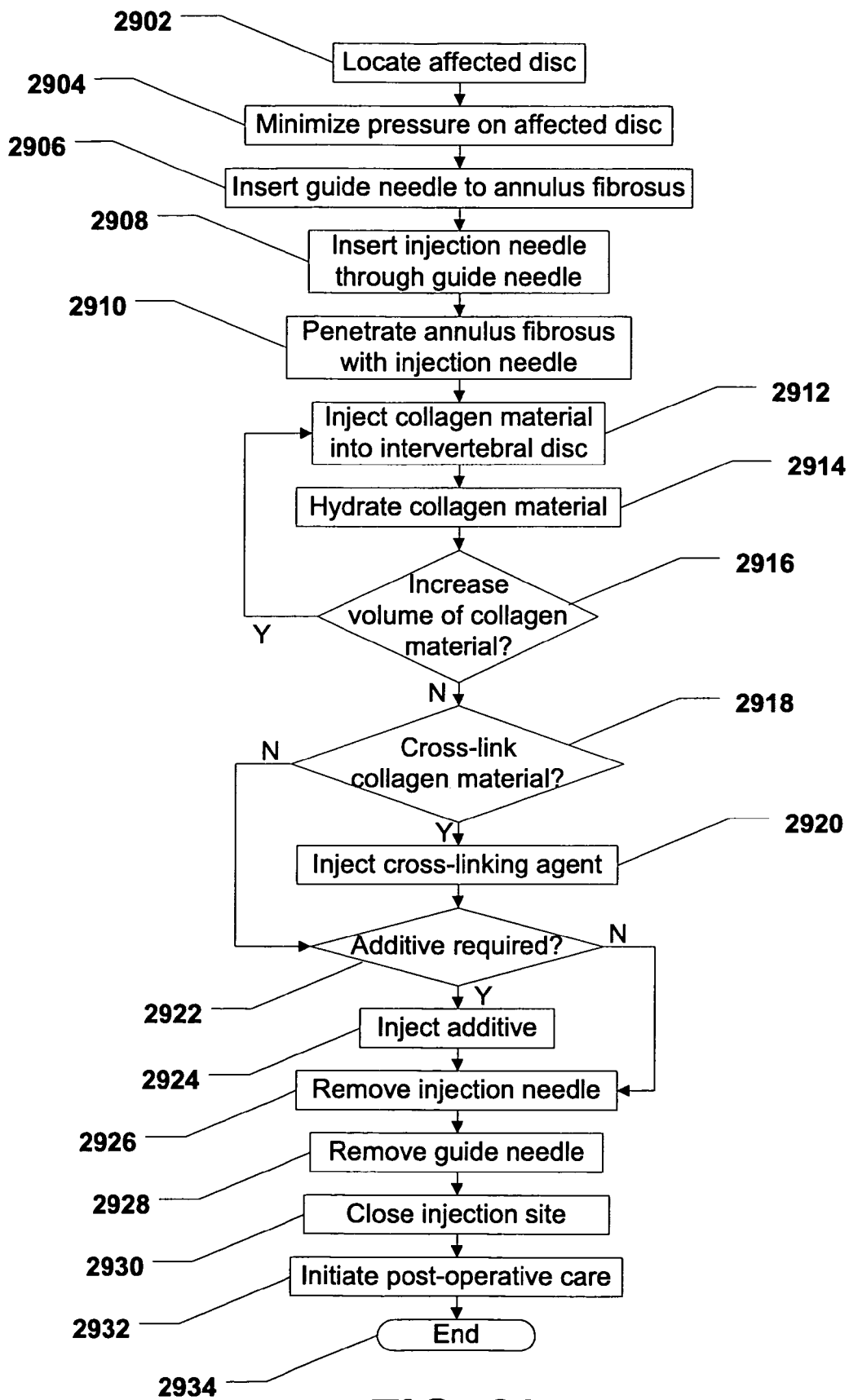
FIG. 29 is a flow chart of a second method of treating an intervertebral disc.

Referring to FIG. 29, a second method of treating an intervertebral disc is illustrated and commences at block 2902. At block 2902, the affected intervertebral disc can be located. At block 2904, the pressure on the intervertebral disc can be reduced. The pressure on the intervertebral disc can be reduced by placing the patient in a position that reduces loading in the area near the vertebra immediately surrounding the intervertebral disc. For example, the patient can be placed in a prone position on a flexible, or hinged, surgical table and the patient's spine can be slightly bent by flexing or bending the flexible surgical table around one or more hinges. In a particular embodiment, reducing pressure on the intervertebral disc can maximize the amount of collagen material injected therein.

Moving to block 2906, a guide needle can be inserted to the annulus fibrosus of the affected intervertebral disc. In a particular embodiment, the guide needle can be inserted such that the tip of the guide needle is immediately adjacent to the annulus fibrosus, but does not pierce the annulus fibrosus. At block 2908, an injection needle can be inserted through the guide needle. Further, at block 2910, the annulus fibrosus can be penetrated with the injection needle. In a particular embodiment, the injection needle can be inserted into the annulus fibrosus such that the tip of the injection needle is approximately near the center of the annulus fibrosus. The location of the tip of the guide needle or the location of the tip of the injection needle can be verified using imaging technology, e.g., fluoroscopy, magnetic resonance imaging, computed tomography, or any other similar technology well known in the art.

Proceeding to block 2912, collagen material can be injected into the intervertebral disc. In a particular embodiment, the collagen material can be the collagen material described herein. Further, the collagen material can be manufactured as described herein. Also, in a particular embodiment, the collagen material can be injected into the nucleus pulposus within the annulus fibrosus. Next, at step 2914, the collagen can be hydrated. In a particular embodiment, the collagen can be hydrated by injecting a liquid, e.g., saline, into the intervertebral disc.

Continuing to decision step 2916, it can be determined whether to increase the volume of collagen material within the nucleus pulposus. This determination can be facilitated using a radio contrast agent injected with the collagen material and imaging technology, e.g., fluoroscopy, magnetic resonance imaging, computed tomography or some other imaging technology well know in the art.

At decision step 2916, if it is determined to increase the volume of collagen material, the method can return to block 2912 and more collagen can be injected into the intervertebral disc. Then, the method can continue as described herein. Conversely, if it is determined not to increase the volume of collagen material, the method can proceed to decision step 2918 and it can be determined whether to cross-link the collagen material. If so, the method proceeds to block 2920 and a cross-linking agent can be injected into the intervertebral disc. In a particular embodiment, the cross-linking agent can be glutaraldehyde, genipin, or a combination thereof. Further, the cross-linking agent can be another protein cross-linking agent. Cross-linking the collagen material can result in a more robust material within the intervertebral disc. From block 2920, the method can proceed to decision step 2922.

Returning to decision step 2918, if it is determined not to cross-link the collagen material, the method can also proceed to decision step 2922. At decision step 2922, it can be determined whether to inject an additive. If it is determined to inject an additive, the method can proceed to block 2924 and an additive can be injected. For example, the additives can include radiocontrast media, drugs, cellular matters, biological factors, or a combination thereof. In a particular embodiment, the drugs can include antibiotics, analgesics, anti-inflammatory drugs, anti-TNF-alpha, steroids, or a combination thereof. Further, the cellular matters can include bone marrow derived stem cells, lipo derived stem cells, or a combination thereof. Also, the biological factor can include bone morphogenetic protein (BMP), cartilage-derived morphogenetic protein (CDMP), platelet derived growth factor (PDGF), insulin-like growth factor (IGF), LIM mineralization protein, fibroblast growth factor (FGF), osteoblast growth factor, or a combination thereof. The additives can also include additives to promote slurry or gel formation. These additives may promote protein folding, water binding, protein-to-protein interaction, water immobilization, or a combination thereof. Additionally, the additives can include polysaccharides such as, proteoglycans, hyaluronic acid, or combination thereof, which can attract or bind water to increase hydration of the intervertebral disc. From block 2924, the method can proceed to block 2926.

Returning to decision step 2922, if it is determined not to inject an additive, the method can also proceed to block 2926. At block 2926, the injection needle can be removed from the patient. Further, at block 2928, the guide needle can be removed from the patient. Moving to block 2930, the injection site can be closed. In a particular embodiment, the injection site can simply be allowed to close due to the elasticity of the patients skin. Alternatively, the injection site can be sutured, if necessary. Proceeding to block 2932, post-operative care can be initiated. Then, the method can end at state 2934.

Description of a Third Method of Treating an Intervertebral Disc

Figure 30:
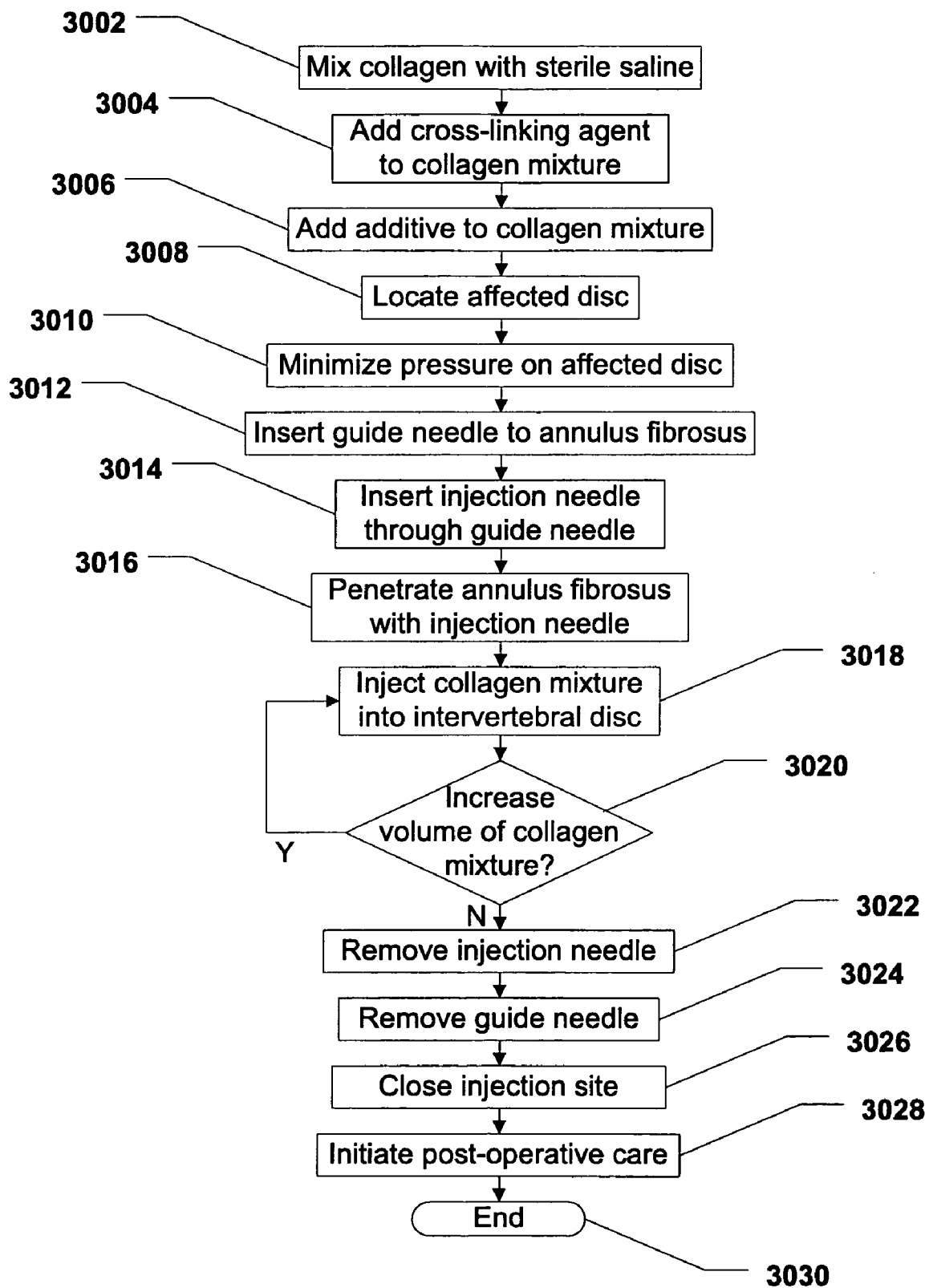
FIG. 30 is a flow chart of a third method of treating an intervertebral disc.

Referring to FIG. 30, a third method of treating an intervertebral disc is shown and commences at block 3002. At block 3002, collagen material can be mixed with sterile saline. In a particular embodiment, the collagen material can be the collagen material described herein. Further, the collagen material can be manufactured as described herein. In a particular embodiment, three-tenths grams (0.3 g) of the collagen material can be mixed with three cubic centimeters (3 cc) of saline to yield a collagen slurry.

Moving to block 3004, a cross-linking agent can be added to the collagen mixture. In a particular embodiment, the cross-linking agent can be glutaraldehyde, genipin, or a combination thereof. Further, the cross-linking agent can be another protein cross-linking agent. At block 3006, an additive can be added to the collagen mixture. For example, the additives can include radiocontrast media, drugs, cellular matters, biological factors, or a combination thereof. In a particular embodiment, the drugs can include antibiotics, analgesics, anti-inflammatory drugs, anti-TNF-alpha, steroids, or a combination thereof. Further, the cellular matters can include bone marrow derived stem cells, lipo derived stem cells, or a combination thereof. Also, the biological factor can include bone morphogenetic protein (BMP), cartilage-derived morphogenetic protein (CDMP), platelet derived growth factor (PDGF), insulin-like growth factor (IGF), LIM mineralization protein, fibroblast growth factor (FGF), osteoblast growth factor, or a combination thereof. The additives can also include additives to promote slurry or gel formation. These additives may promote protein folding, water binding, protein-to-protein interaction, water immobilization, or a combination thereof. Additionally, the additives can include polysaccharides such as, proteoglycans, hyaluronic acid, or combination thereof, which can attract or bind water to increase hydration of the intervertebral disc.

Proceeding to block 3008, the affected intervertebral disc can be located. At block 3010, the pressure on the intervertebral disc can be reduced. The pressure on the intervertebral disc can be reduced by placing the patient in a position that reduces loading in the area near the vertebra immediately surrounding the intervertebral disc. For example, the patient can be placed in a prone position on a flexible, or hinged, surgical table and the patient's spine can be slightly bent by flexing or bending the flexible surgical table around one or more hinges. In a particular embodiment, reducing pressure on the intervertebral disc can maximize the amount of collagen material injected therein.

Moving to block 3012, a guide needle can be inserted to the annulus fibrosus of the affected intervertebral disc. In a particular embodiment, the guide needle can be inserted such that the tip of the guide needle is immediately adjacent to the annulus fibrosus, but does not pierce the annulus fibrosus. At block 3014, an injection needle can be inserted through the guide needle. Further, at block 3016, the annulus fibrosus can be penetrated with the injection needle. In a particular embodiment, the injection needle can be inserted into the annulus fibrosus such that the tip of the injection needle is approximately near the center of the annulus fibrosus. The location of the tip of the guide needle or the location of the tip of the injection needle can be verified using imaging technology, e.g., fluoroscopy, magnetic resonance imaging, computed tomography, or any other similar technology well known in the art.

Proceeding to block 3018, the collagen material can be injected into the intervertebral disc. In a particular embodiment, the collagen material can be injected into the nucleus pulposus within the annulus fibrosus. Continuing to decision step 3020, it can be determined whether to increase the volume of collagen material within the nucleus pulposus. This determination can be facilitated using a radio contrast agent injected with the collagen material and imaging technology, e.g., fluoroscopy, magnetic resonance imaging, computed tomography or some other imaging technology well know in the art. If it is determined to increase the volume of collagen material, the method can return to block 3018 and more collagen can be injected into the intervertebral disc. Then, the method can continue as described herein.

Conversely, if it is determined not to increase the volume of collagen material, the method can proceed to block 3022, the injection needle can be removed from the patient. Further, at block 3024, the guide needle can be removed from the patient. Moving to block 3026, the injection site can be closed. In a particular embodiment, the injection site can simply be allowed to close due to the elasticity of the patients skin. Alternatively, the injection site can be sutured, if necessary. Proceeding to block 3028, post-operative care can be initiated. Then, the method can end at state 3030.

Description of a First Method of Treating a Synovial Joint

Figure 31:
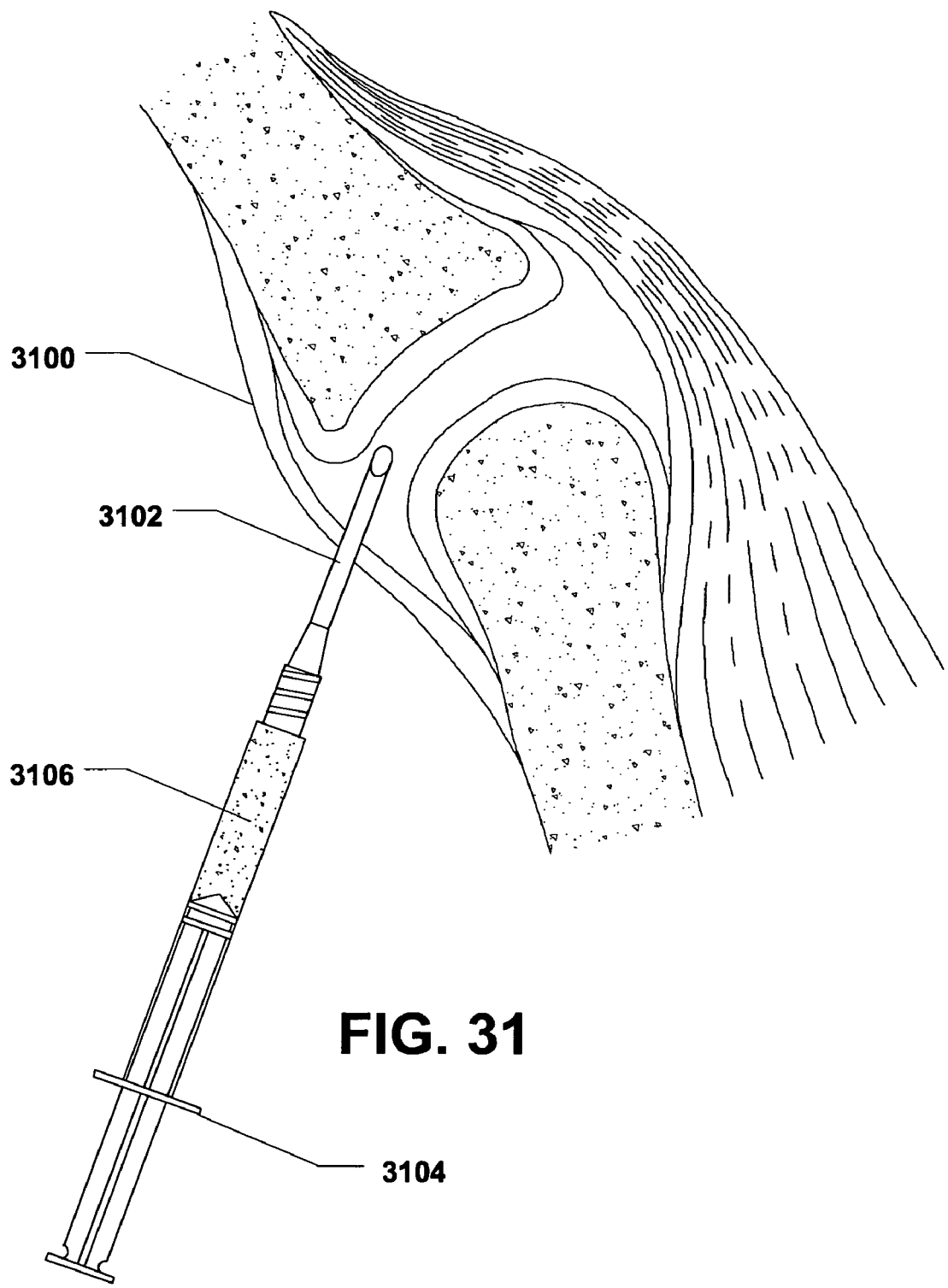
FIG. 31 is a cross-section view of a synovial joint with a collagen material injected therein.

FIG. 31 depicts a synovial joint, designated 3100. As shown, a needle 3102 can be inserted into the synovial joint 3100. The needle 3102 can extend from a syringe 3104 that can be filled with a collagen material 3106, e.g., a collagen material described herein. The collagen material 3106 can be injected into the synovial joint 3100 in order to bulk up the synovial joint 3100 and minimize deterioration of the synovial joint 3100 due to the normal aging process or injury.

Figure 32:
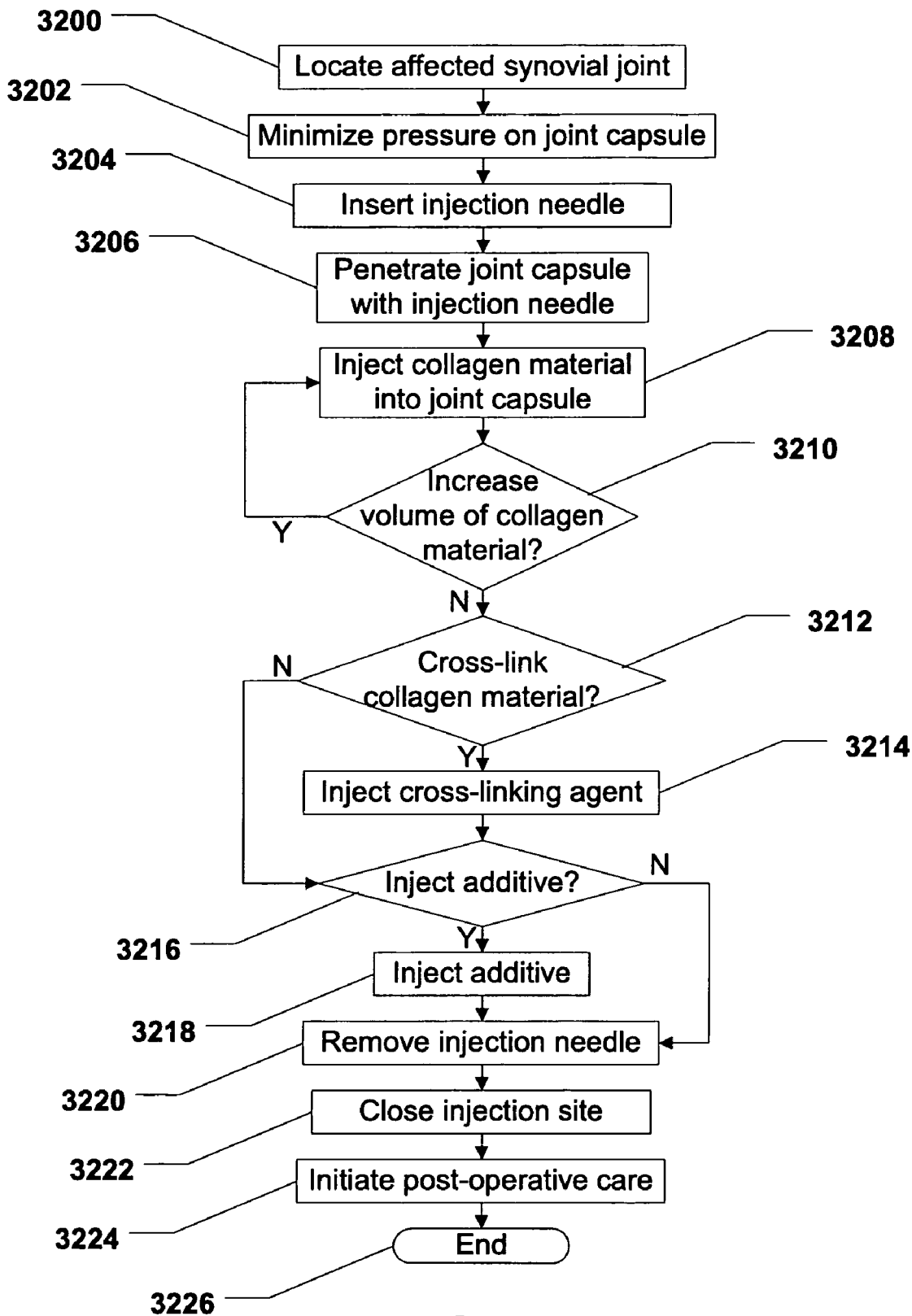
FIG. 32 is a flow chart of a first method of treating a synovial joint.

Referring to FIG. 32, a method of treating a synovial joint is illustrated and commences at block 3200. At block 3200, the affected synovial joint can be located. At block 3202, the pressure on the joint capsule can be reduced. The pressure on the joint capsule can be reduced by placing the patient in a position that relaxes the synovial joint and weight is removed from the synovial joint. In a particular embodiment, reducing pressure on the joint capsule can maximize the amount of collagen material injected therein.

Moving to block 3204, an injection needle inserted into the patient in an area at or near the synovial joint. At block 3206, the joint capsule can be penetrated with the injection needle. In a particular embodiment, the injection needle can be inserted into the joint capsule such that the tip of the injection needle is approximately near the center of the joint capsule. The location of the tip of the injection needle can be verified using imaging technology, e.g., fluoroscopy, magnetic resonance imaging, computed tomography, or any other similar technology well known in the art.

Proceeding to block 3208, collagen material can be injected into the synovial joint. In a particular embodiment, the collagen material can be the collagen material described herein. Further, the collagen material can be manufactured as described herein. Also, in a particular embodiment, the collagen material can be injected into the synovial joint capsule. In a particular embodiment, the collagen material can be in the form of a collagen slurry, i.e., collagen material mixed with saline.

Continuing to decision step 3210, it can be determined whether to increase the volume of collagen material within the synovial joint. This determination can be facilitated using a radio contrast agent injected with the collagen material and imaging technology, e.g., fluoroscopy, magnetic resonance imaging, computed tomography or some other imaging technology well know in the art.

At decision step 3210, if it is determined to increase the volume of collagen material, the method can return to block 3208 and more collagen can be injected into the synovial joint. Thereafter, the method can continue as described herein. Conversely, if it is determined not to increase the volume of collagen material, the method can proceed to decision step 3212 and it can be determined whether to cross-link the collagen material. If so, the method proceeds to block 3214 and a cross-linking agent can be injected into the synovial joint. In a particular embodiment, the cross-linking agent can be glutaraldehyde, genipin, or a combination thereof. Further, the cross-linking agent can be another protein cross-linking agent. Cross-linking the collagen material can result in a more robust material within the synovial joint. From block 3214, the method can proceed to decision step 3216.

Returning to decision step 3212, if it is determined not to cross-link the collagen material, the method can also proceed to decision step 3216. At decision step 3216, it can be determined whether to inject an additive. If it is determined to inject an additive, the method can proceed to block 3218 and an additive can be injected. For example, the additives can include radiocontrast media, drugs, cellular matters, biological factors, or a combination thereof. In a particular embodiment, the drugs can include antibiotics, analgesics, anti-inflammatory drugs, anti-TNF-alpha, steroids, or a combination thereof. Further, the cellular matters can include bone marrow derived stem cells, lipo derived stem cells, or a combination thereof. Also, the biological factor can include bone morphogenetic protein (BMP), cartilage-derived morphogenetic protein (CDMP), platelet derived growth factor (PDGF), insulin-like growth factor (IGF), LIM mineralization protein, fibroblast growth factor (FGF), osteoblast growth factor, or a combination thereof. The additives can also include additives to promote slurry or gel formation. These additives may promote protein folding, water binding, protein-to-protein interaction, water immobilization, or a combination thereof. Additionally, the additives can include polysaccharides such as, proteoglycans, hyaluronic acid, or combination thereof, which can attract or bind water to increase hydration of the synovial joint. From block 3218, the method can proceed to block 3220.

Returning to decision step 3216, if it is determined not to inject an additive, the method can also proceed to block 3220. At block 3220, the injection needle can be removed from the patient. Further, at block 3222, the injection site can be closed. In a particular embodiment, the injection site can simply be allowed to close due to the elasticity of the patients skin. Alternatively, the injection site can be sutured, if necessary. Proceeding to block 3224, post-operative care can be initiated. Then, the method can end at state 3226.

Description of a Second Method of Treating a Synovial Joint

Figure 33:
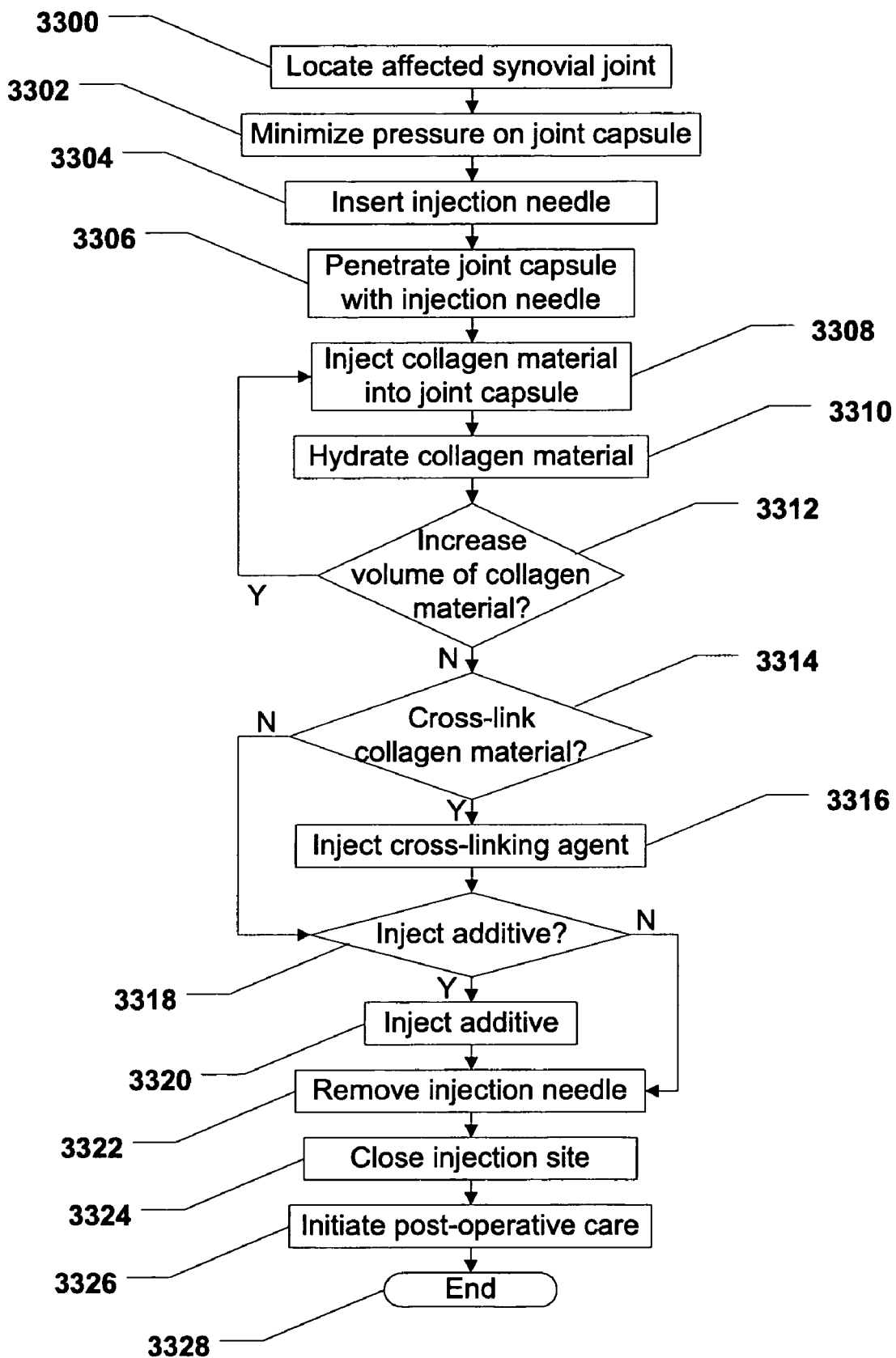
FIG. 33 is a flow chart of a second method of treating a synovial joint.

Referring to FIG. 33, another method of treating a synovial joint is illustrated and commences at block 3300. At block 3300, the affected synovial joint can be located. At block 3302, the pressure on the synovial joint can be reduced. The pressure on the joint capsule can be reduced by placing the patient in a position that relaxes the synovial joint and weight is removed from the synovial joint. In a particular embodiment, reducing pressure on the joint capsule can maximize the amount of collagen material injected therein.

At block 3304, an injection needle inserted into the patient in an area at or near the synovial joint. At block 3306, the joint capsule can be penetrated with the injection needle. In a particular embodiment, the injection needle can be inserted into the joint capsule such that the tip of the injection needle is approximately near the center of the joint capsule. The location of the tip of the injection needle can be verified using imaging technology, e.g., fluoroscopy, magnetic resonance imaging, computed tomography, or any other similar technology well known in the art.

Proceeding to block 3308, collagen material can be injected into the synovial joint. In a particular embodiment, the collagen material can be the collagen material described herein. Further, the collagen material can be manufactured as described herein. Also, in a particular embodiment, the collagen material can be injected into the synovial joint capsule. Next, at step 3310, the collagen can be hydrated. In a particular embodiment, the collagen can be hydrated by injecting a liquid, e.g., saline, into the synovial joint capsule.

Continuing to decision step 3312, it can be determined whether to increase the volume of collagen material within the synovial joint. This determination can be facilitated using a radio contrast agent injected with the collagen material and imaging technology, e.g., fluoroscopy, magnetic resonance imaging, computed tomography or some other imaging technology well know in the art.

At decision step 3312, if it is determined to increase the volume of collagen material, the method can return to block 3308 and more collagen can be injected into the synovial joint. Then, the method can continue as described herein. Conversely, if it is determined not to increase the volume of collagen material, the method can proceed to decision step 3314 and it can be determined whether to cross-link the collagen material. If so, the method proceeds to block 3316 and a cross-linking agent can be injected into the synovial joint. In a particular embodiment, the cross-linking agent can be glutaraldehyde, genipin, or a combination thereof. Further, the cross-linking agent can be another protein cross-linking agent. Cross-linking the collagen material can result in a more robust material within the synovial joint. From block 3316, the method can proceed to decision step 3318.

Returning to decision step 3314, if it is determined not to cross-link the collagen material, the method can also proceed to decision step 3318. At decision step 3318, it can be determined whether to inject an additive. If it is determined to inject an additive, the method can proceed to block 3320 and an additive can be injected. For example, the additives can include radiocontrast media, drugs, cellular matters, biological factors, or a combination thereof. In a particular embodiment, the drugs can include antibiotics, analgesics, anti-inflammatory drugs, anti-TNF-alpha, steroids, or a combination thereof. Further, the cellular matters can include bone marrow derived stem cells, lipo derived stem cells, or a combination thereof. Also, the biological factor can include bone morphogenetic protein (BMP), cartilage-derived morphogenetic protein (CDMP), platelet derived growth factor (PDGF), insulin-like growth factor (IGF), LIM mineralization protein, fibroblast growth factor (FGF), osteoblast growth factor, or a combination thereof. The additives can also include additives to promote slurry or gel formation. These additives may promote protein folding, water binding, protein-to-protein interaction, water immobilization, or a combination thereof. Additionally, the additives can include polysaccharides such as, proteoglycans, hyaluronic acid, or combination thereof, which can attract or bind water to increase hydration of the synovial joint. From block 3320, the method can proceed to block 3322.

Returning to decision step 3318, if it is determined not to inject an additive, the method can also proceed to block 3322. At block 3322, the injection needle can be removed from the patient. Further, at block 3324, the injection site can be closed. In a particular embodiment, the injection site can simply be allowed to close due to the elasticity of the patients skin. Alternatively, the injection site can be sutured, if necessary. Proceeding to block 3326, post-operative care can be initiated. Then, the method can end at state 3328.

Description of a Third Method of Treating a Synovial Joint

Figure 34:
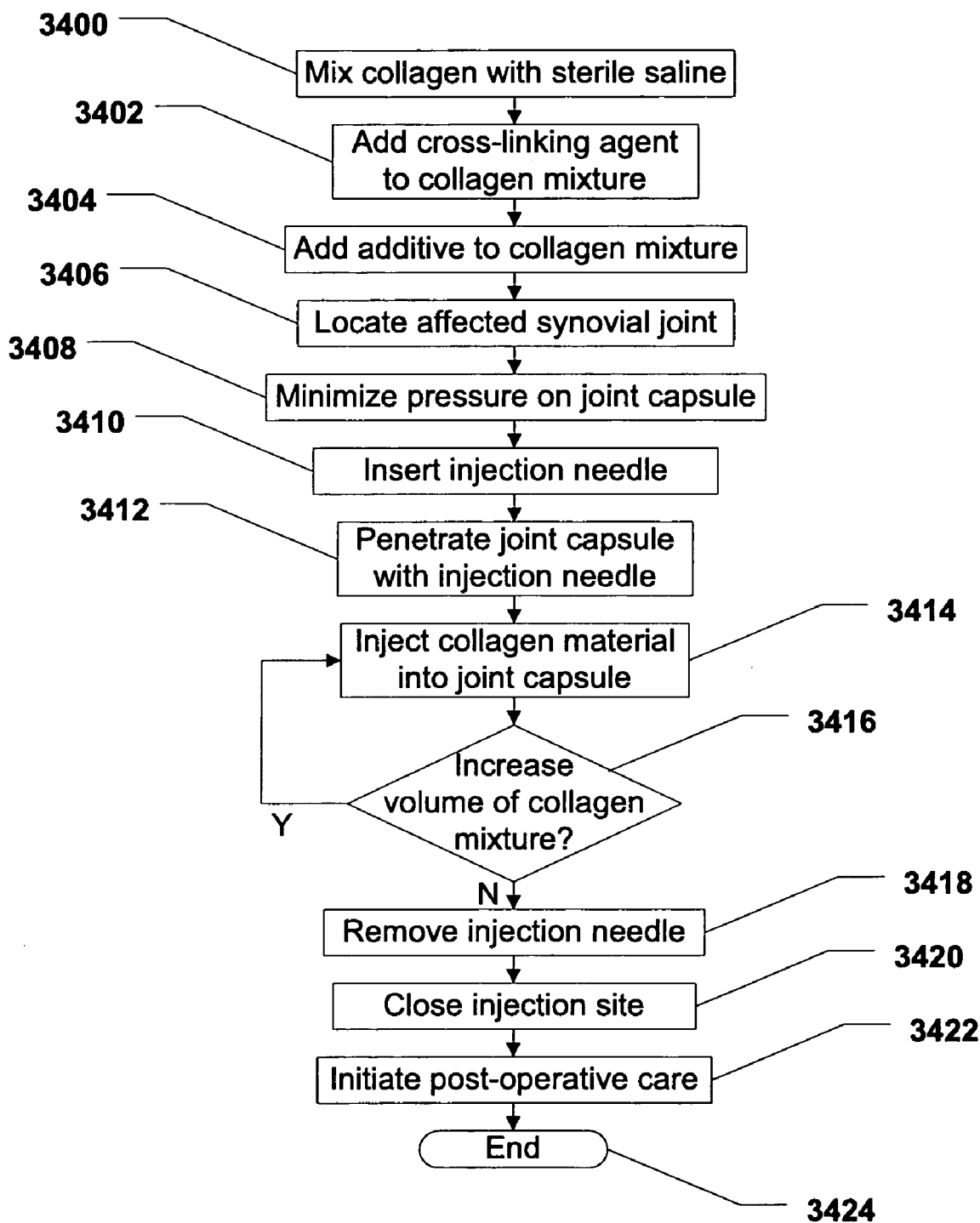
FIG. 34 is a flow chart of a third method of treating a synovial joint.

Referring to FIG. 34, yet another method of treating a synovial joint is shown and commences at block 3400. At block 3400, collagen material can be mixed with sterile saline. In a particular embodiment, the collagen material can be the collagen material described herein. Further, the collagen material can be manufactured as described herein. In a particular embodiment, three-tenths grams (0.3 g) of the collagen material can be mixed with three cubic centimeters (3.0 cc) of saline to yield a collagen slurry.

Moving to block 3402, a cross-linking agent can be added to the collagen mixture. In a particular embodiment, the cross-linking agent can be glutaraldehyde, genipin, or a combination thereof. Further, the cross-linking agent can be another protein cross-linking agent. At block 3404, an additive can be added to the collagen mixture. For example, the additives can include radiocontrast media, drugs, cellular matters, biological factors, or a combination thereof. In a particular embodiment, the drugs can include antibiotics, analgesics, anti-inflammatory drugs, anti-TNF-alpha, steroids, or a combination thereof. Further, the cellular matters can include bone marrow derived stem cells, lipo derived stem cells, or a combination thereof. Also, the biological factor can include bone morphogenetic protein (BMP), cartilage-derived morphogenetic protein (CDMP), platelet derived growth factor (PDGF), insulin-like growth factor (IGF), LIM mineralization protein, fibroblast growth factor (FGF), osteoblast growth factor, or a combination thereof. The additives can also include additives to promote slurry or gel formation. These additives may promote protein folding, water binding, protein-to-protein interaction, water immobilization, or a combination thereof. Additionally, the additives can include polysaccharides such as, proteoglycans, hyaluronic acid, or combination thereof, which can attract or bind water to increase hydration of the synovial joint.

Proceeding to block 3406, the affected synovial joint can be located. At block 3408, the pressure on the synovial joint can be reduced. The pressure on the joint capsule can be reduced by placing the patient in a position that relaxes the synovial joint and weight is removed from the synovial joint. In a particular embodiment, reducing pressure on the joint capsule can maximize the amount of collagen material injected therein.

At block 3410, an injection needle inserted into the patient in an area at or near the synovial joint. At block 3412, the joint capsule can be penetrated with the injection needle. In a particular embodiment, the injection needle can be inserted into the joint capsule such that the tip of the injection needle is approximately near the center of the joint capsule. The location of the tip of the injection needle can be verified using imaging technology, e.g., fluoroscopy, magnetic resonance imaging, computed tomography, or any other similar technology well known in the art.

Proceeding to block 3414, collagen material can be injected into the synovial joint. In a particular embodiment, the collagen material can be the collagen material described herein. Further, the collagen material can be manufactured as described herein. Also, in a particular embodiment, the collagen material can be injected into the synovial joint capsule.

Continuing to decision step 3416, it can be determined whether to increase the volume of collagen material within the synovial joint. This determination can be facilitated using a radio contrast agent injected with the collagen material and imaging technology, e.g., fluoroscopy, magnetic resonance imaging, computed tomography or some other imaging technology well know in the art.

At decision step 3416, if it is determined to increase the volume of collagen material, the method can return to block 3414 and more collagen can be injected into the synovial joint. Then, the method can continue as described herein. Conversely, if it is determined not to increase the volume of collagen material, the method can proceed to block 3418 and the injection needle can be removed from the patient. Further, at block 3420, the injection site can be closed. In a particular embodiment, the injection site can simply be allowed to close due to the elasticity of the patients skin. Alternatively, the injection site can be sutured, if necessary. Proceeding to block 3422, post-operative care can be initiated. Then, the method can end at state 3424.

Description of a First Method of Treating Tissue

Figure 35:
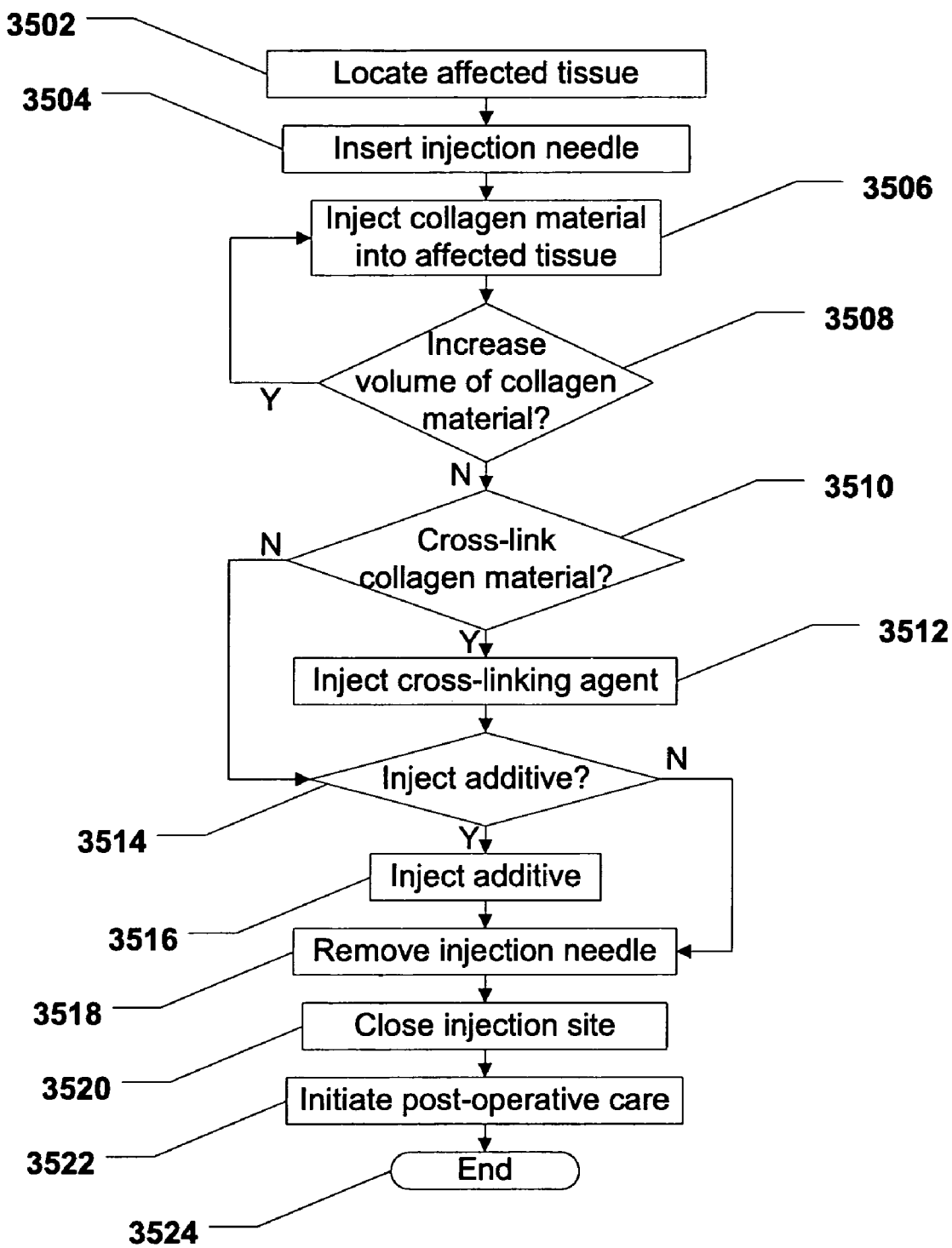
FIG. 35 is a flow chart of a first method of treating tissue.

Referring to FIG. 35, a method of treating tissue is illustrated and commences at block 3502. At block 3502, the affected tissue can be located. In a particular embodiment, the tissue can be soft tissue, bone, skin, or a combination thereof.

Moving to block 3504, an injection needle can be inserted into the affected tissue. In a particular embodiment, the injection needle is inserted so that the tip of the injection needle is located near the center of the affected tissue. The location of the tip of the injection needle can be verified using imaging technology, e.g., fluoroscopy, magnetic resonance imaging, computed tomography, or any other similar technology well known in the art.

At block 3506, collagen material can be injected into the tissue. In a particular embodiment, the collagen material can be the collagen material described herein. Further, the collagen material can be manufactured as described herein. In a particular embodiment, the collagen material can be in the form of a collagen slurry, i.e., collagen material mixed with saline.

Continuing to decision step 3508, it can be determined whether to increase the volume of collagen material within the tissue. This determination can be facilitated using a radio contrast agent injected with the collagen material and imaging technology, e.g., fluoroscopy, magnetic resonance imaging, computed tomography or some other imaging technology well know in the art.

At decision step 3508, if it is determined to increase the volume of collagen material, the method can return to block 3506 and more collagen can be injected into the tissue. Thereafter, the method can continue as described herein. Conversely, if it is determined not to increase the volume of collagen material, the method can proceed to decision step 3510 and it can be determined whether to cross-link the collagen material. If so, the method proceeds to block 3512 and a cross-linking agent can be injected into the tissue. In a particular embodiment, the cross-linking agent can be glutaraldehyde, genipin, or a combination thereof. Further, the cross-linking agent can be another protein cross-linking agent. Cross-linking the collagen material can result in a more robust material within the tissue. From block 3512, the method can proceed to decision step 3514.

Returning to decision step 3510, if it is determined not to cross-link the collagen material, the method can also proceed to decision step 3514. At decision step 3514, it can be determined whether to inject an additive. If it is determined to inject an additive, the method can proceed to block 3516 and an additive can be injected. For example, the additives can include radiocontrast media, drugs, cellular matters, biological factors, or a combination thereof. In a particular embodiment, the drugs can include antibiotics, analgesics, anti-inflammatory drugs, anti-TNF-alpha, steroids, or a combination thereof. Further, the cellular matters can include bone marrow derived stem cells, lipo derived stem cells, or a combination thereof. Also, the biological factor can include bone morphogenetic protein (BMP), cartilage-derived morphogenetic protein (CDMP), platelet derived growth factor (PDGF), insulin-like growth factor (IGF), LIM mineralization protein, fibroblast growth factor (FGF), osteoblast growth factor, or a combination thereof. The additives can also include additives to promote slurry or gel formation. These additives may promote protein folding, water binding, protein-to-protein interaction, water immobilization, or a combination thereof. Additionally, the additives can include polysaccharides such as, proteoglycans, hyaluronic acid, or combination thereof, which can attract or bind water. From block 3516, the method can proceed to block 3518.

Returning to decision step 3514, if it is determined not to inject an additive, the method can also proceed to block 3518. At block 3518, the injection needle can be removed from the patient. Further, at block 3520, the injection site can be closed. In a particular embodiment, the injection site can simply be allowed to close due to the elasticity of the patients skin. Alternatively, the injection site can be sutured, if necessary. Proceeding to block 3522, post-operative care can be initiated. Then, the method can end at state 3524.

Description of a Second Method of Treating Tissue

Figure 36:
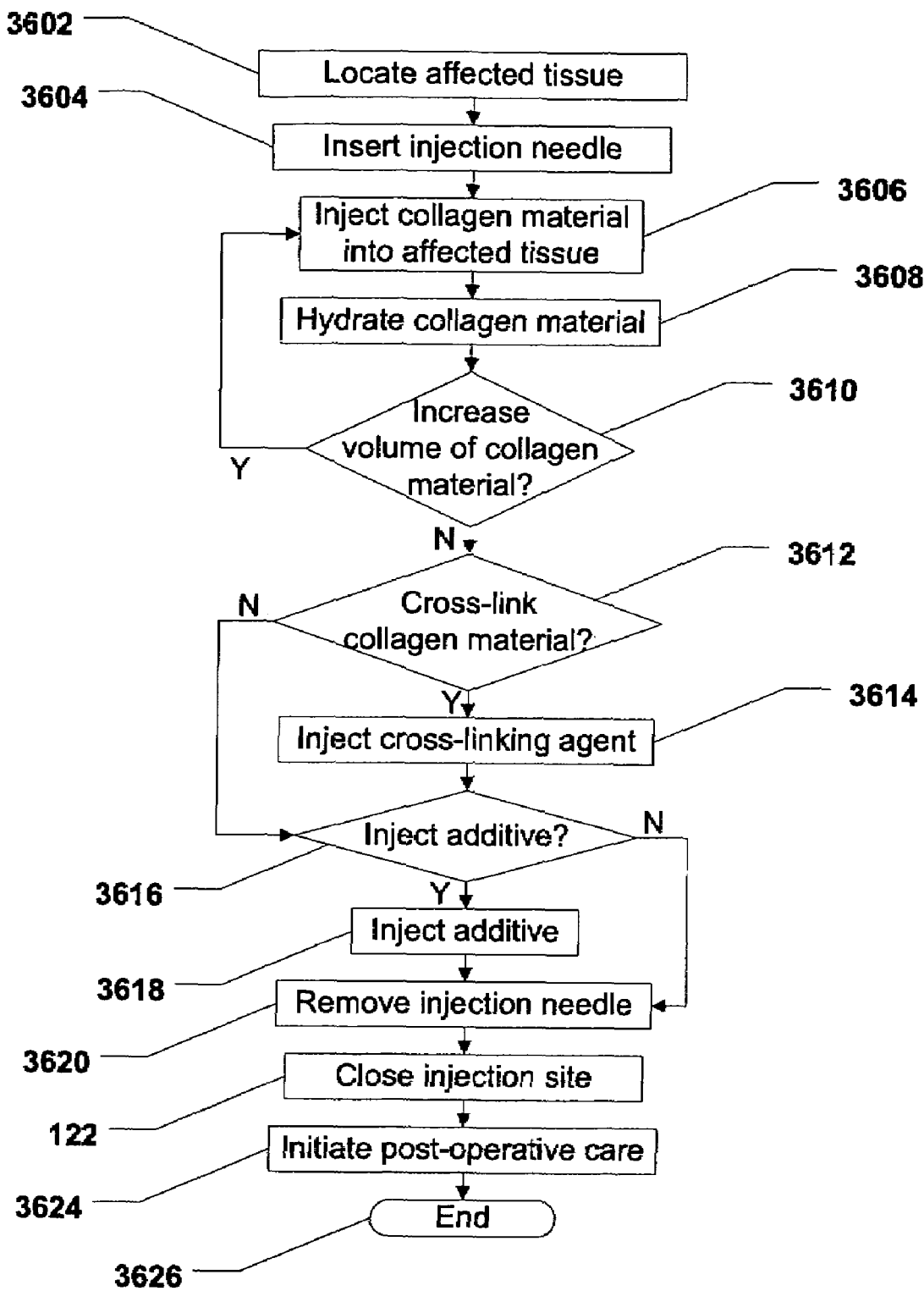
FIG. 36 is a flow chart of a second method of treating tissue.

Referring to FIG. 36, a method of treating tissue is illustrated and commences at block 3602. At block 3602, the affected tissue can be located. In a particular embodiment, the tissue can be soft tissue, bone, skin, or a combination thereof.

Moving to block 3604, an injection needle can be inserted into the affected tissue. In a particular embodiment, the injection needle is inserted so that the tip of the injection needle is located near the center of the affected tissue. The location of the tip of the injection needle can be verified using imaging technology, e.g., fluoroscopy, magnetic resonance imaging, computed tomography, or any other similar technology well known in the art.

At block 3606, collagen material can be injected into the tissue. In a particular embodiment, the collagen material can be the collagen material described herein. Further, the collagen material can be manufactured as described herein. Also, in a particular embodiment, the collagen material can be injected into the nucleus pulposus within the annulus fibrosus. (DRY) Next, at step 3608, the collagen can be hydrated. In a particular embodiment, the collagen can be hydrated by injecting a liquid, e.g., saline, into the synovial joint capsule.

Continuing to decision step 3610, it can be determined whether to increase the volume of collagen material within the tissue. This determination can be facilitated using a radio contrast agent injected with the collagen material and imaging technology, e.g., fluoroscopy, magnetic resonance imaging, computed tomography or some other imaging technology well know in the art.

At decision step 3610, if it is determined to increase the volume of collagen material, the method can return to block 3606 and more collagen can be injected into the tissue. Thereafter, the method can continue as described herein. Conversely, if it is determined not to increase the volume of collagen material, the method can proceed to decision step 3612 and it can be determined whether to cross-link the collagen material. If so, the method proceeds to block 3614 and a cross-linking agent can be injected into the tissue. In a particular embodiment, the cross-linking agent can be glutaraldehyde, genipin, or a combination thereof. Further, the cross-linking agent can be another protein cross-linking agent. Cross-linking the collagen material can result in a more robust material within the tissue. From block 3614, the method can proceed to decision step 3616.

Returning to decision step 3612, if it is determined not to cross-link the collagen material, the method can also proceed to decision step 3616. At decision step 3616, it can be determined whether to inject an additive. If it is determined to inject an additive, the method can proceed to block 3618 and an additive can be injected. For example, the additives can include radiocontrast media, drugs, cellular matters, biological factors, or a combination thereof. In a particular embodiment, the drugs can include antibiotics, analgesics, anti-inflammatory drugs, anti-TNF-alpha, steroids, or a combination thereof. Further, the cellular matters can include bone marrow derived stem cells, lipo derived stem cells, or a combination thereof. Also, the biological factor can include bone morphogenetic protein (BMP), cartilage-derived morphogenetic protein (CDMP), platelet derived growth factor (PDGF), insulin-like growth factor (IGF), LIM mineralization protein, fibroblast growth factor (FGF), osteoblast growth factor, or a combination thereof. The additives can also include additives to promote slurry or gel formation. These additives may promote protein folding, water binding, protein-to-protein interaction, water immobilization, or a combination thereof. Additionally, the additives can include polysaccharides such as, proteoglycans, hyaluronic acid, or combination thereof, which can attract or bind water. From block 3618, the method can proceed to block 3620.

Returning to decision step 3616, if it is determined not to inject an additive, the method can also proceed to block 3620. At block 3620, the injection needle can be removed from the patient. Further, at block 3622, the injection site can be closed. In a particular embodiment, the injection site can simply be allowed to close due to the elasticity of the patients skin. Alternatively, the injection site can be sutured, if necessary. Proceeding to block 3624, post-operative care can be initiated. Then, the method can end at state 3626.

Description of a Third Method of Treating Tissue

Figure 37:
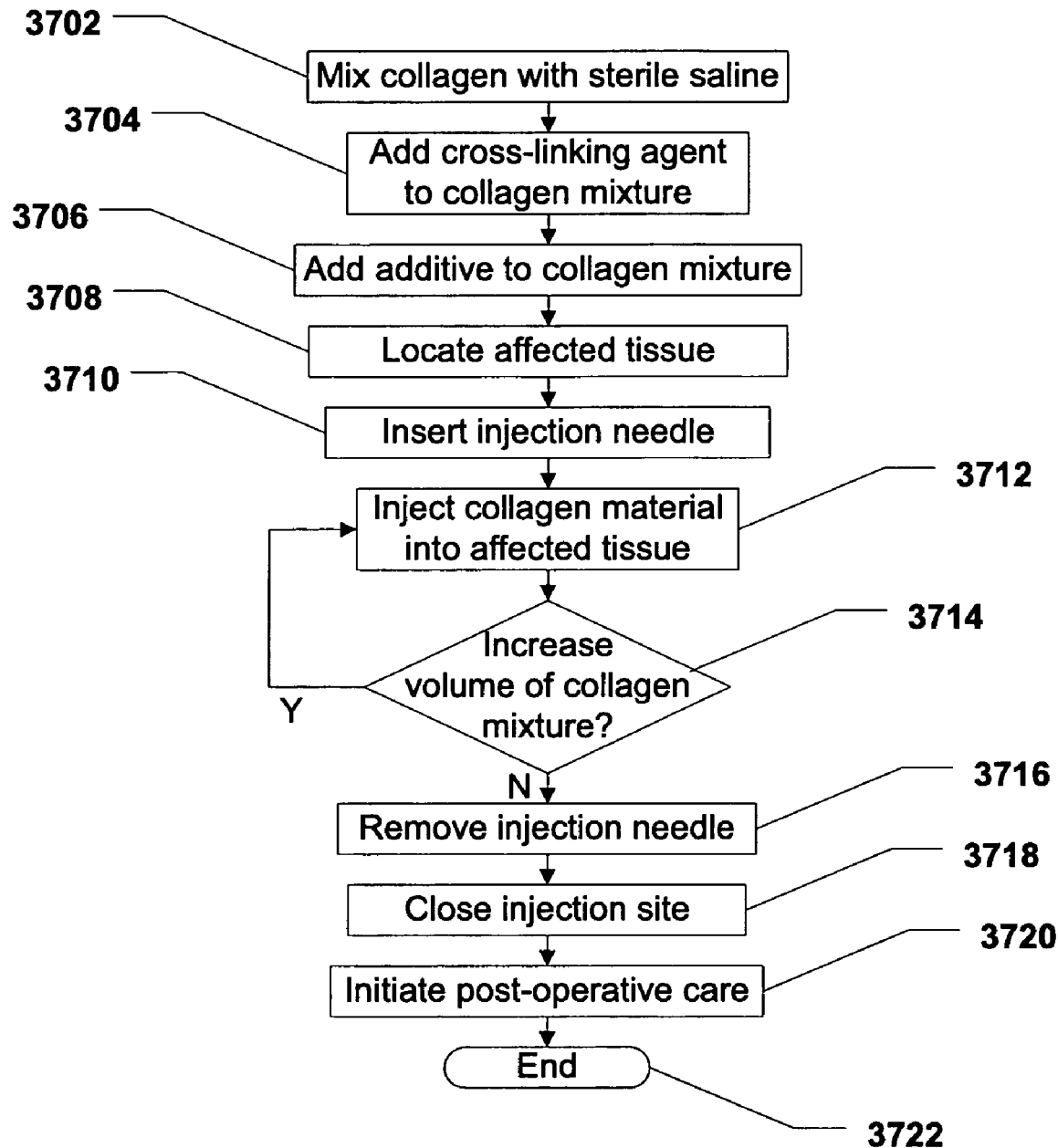
FIG. 37 is a flow chart of a third method of treating tissue.

Referring to FIG. 37, yet another method of treating tissue is shown and commences at block 3702. At block 3702, collagen material can be mixed with sterile saline. In a particular embodiment, the collagen material can be the collagen material described herein. Further, the collagen material can be manufactured as described herein. In a particular embodiment, three-tenths grams (0.3 g) of the collagen material can be mixed with cubic centimeters (3.0 cc) of saline to yield a collagen slurry.

Moving to block 3704, a cross-linking agent can be added to the collagen mixture. In a particular embodiment, the cross-linking agent can be glutaraldehyde, genipin, or a combination thereof. Further, the cross-linking agent can be another protein cross-linking agent. At block 3706, an additive can be added to the collagen mixture. For example, the additives can include radiocontrast media, drugs, cellular matters, biological factors, or a combination thereof. In a particular embodiment, the drugs can include antibiotics, analgesics, anti-inflammatory drugs, anti-TNF-alpha, steroids, or a combination thereof. Further, the cellular matters can include bone marrow derived stem cells, lipo derived stem cells, or a combination thereof. Also, the biological factor can include bone morphogenetic protein (BMP), cartilage-derived morphogenetic protein (CDMP), platelet derived growth factor (PDGF), insulin-like growth factor (IGF), LIM mineralization protein, fibroblast growth factor (FGF), osteoblast growth factor, or a combination thereof. The additives can also include additives to promote slurry or gel formation. These additives may promote protein folding, water binding, protein-to-protein interaction, water immobilization, or a combination thereof. Additionally, the additives can include polysaccharides such as, proteoglycans, hyaluronic acid, or combination thereof, which can attract or bind water.

Proceeding to block 3708, the affected tissue can be located. In a particular embodiment, the tissue can be soft tissue, bone, skin, or a combination thereof. At block 3710, an injection needle can be inserted into the affected tissue. In a particular embodiment, the injection needle is inserted so that the tip of the injection needle is located near the center of the affected tissue. The location of the tip of the injection needle can be verified using imaging technology, e.g., fluoroscopy, magnetic resonance imaging, computed tomography, or any other similar technology well known in the art.

Further, at block 3712, collagen material can be injected into the tissue. In a particular embodiment, the collagen material can be the collagen material described herein. Further, the collagen material can be manufactured as described herein. In a particular embodiment, the collagen material can be in the form of a collagen slurry, i.e., collagen material mixed with saline.

Continuing to decision step 3714, it can be determined whether to increase the volume of collagen material within the tissue. This determination can be facilitated using a radio contrast agent injected with the collagen material and imaging technology, e.g., fluoroscopy, magnetic resonance imaging, computed tomography or some other imaging technology well know in the art.

At decision step 3714, if it is determined to increase the volume of collagen material, the method can return to block 3712 and more collagen can be injected into the tissue. Thereafter, the method can continue as described herein. Conversely, if it is determined not to increase the volume of collagen material, the method can proceed to block 3716 and the injection needle can be removed from the patient. Further, at block 3718, the injection site can be closed. In a particular embodiment, the injection site can simply be allowed to close due to the elasticity of the patients skin. Alternatively, the injection site can be sutured, if necessary. Proceeding to block 3720, post-operative care can be initiated. Then, the method can end at state 3722.

Description of a Syringe

Figure 38:
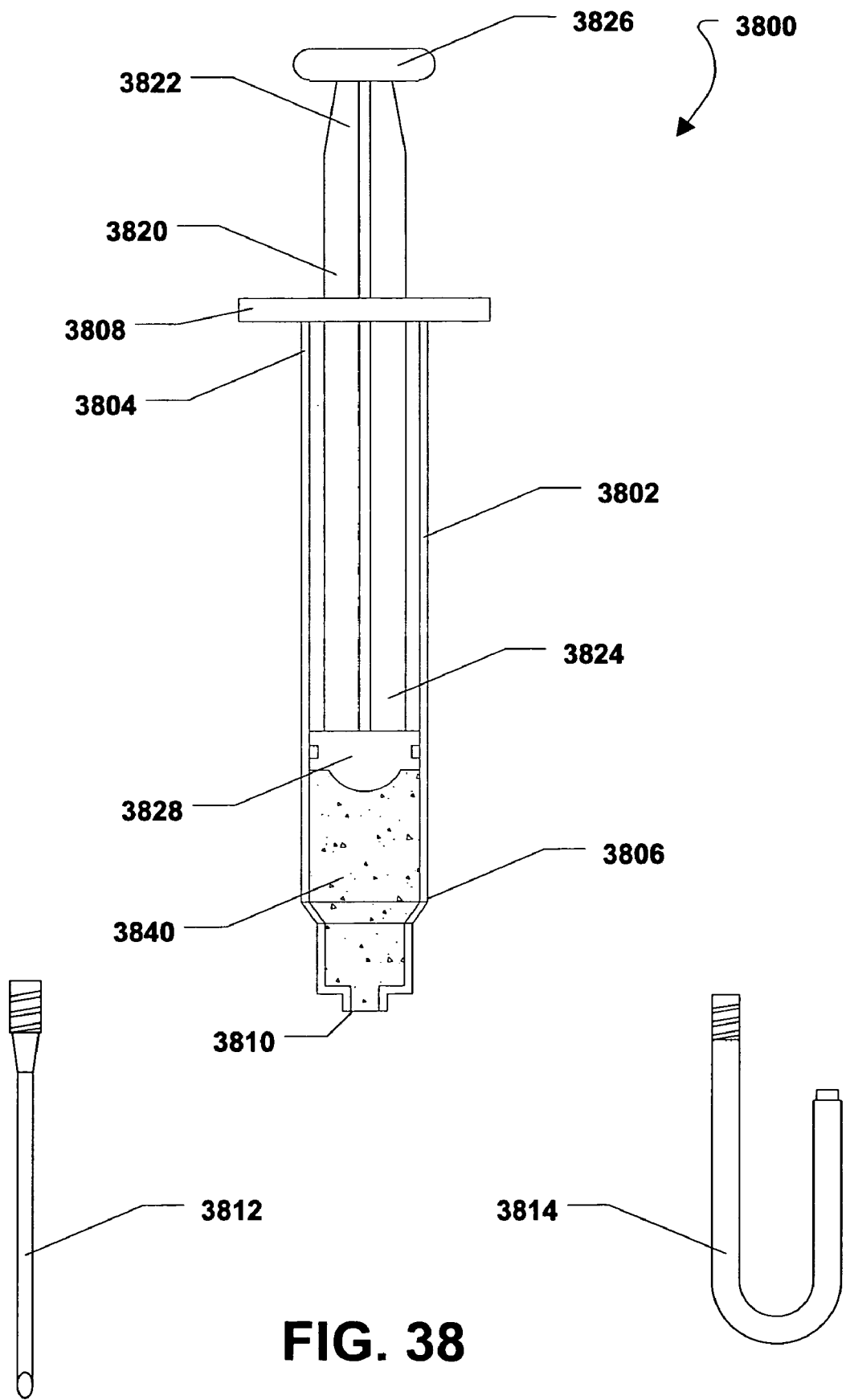
FIG. 38 is a plan view of a syringe.

FIG. 38 illustrates a syringe that can be used to delivery collagen material, e.g., a collagen material according to one or more of the embodiments described herein. As shown, the syringe 3800 can include a syringe barrel 3802 that can define a proximal end 3804 and a distal end 3806. The proximal end 3804 of the syringe 3800 can include a syringe barrel handle 3808. Further, the distal end 3806 of the syringe 3800 can include a needle hilt 3810. A needle 3812 can be connected to the needle hilt 3810. Alternatively, a flexible tube 3814 can be connected to the needle hilt 3810 and the needle 3812 can be connected to the flexible tube 3814.

As shown in FIG. 38, a syringe plunger 3820 can be disposed within the syringe barrel 3802. The syringe plunger 3820 can include a proximal end 3822 and a distal end 3824. Also, the proximal end 3822 of the syringe plunger 3820 can include a syringe plunger handle 3826 coupled thereto. Moreover, the distal end 3824 of the syringe plunger 3820 can include a plunger tip 3828. FIG. 38 also indicates that the syringe 3800 can be filled with a collagen material 3840, e.g., a collagen material according to one or more embodiments described herein.

In a particular embodiment, the syringe 3800 can be used in conjunction with a collagen delivery device, described in detail below. Accordingly, when a plunger of a collagen delivery device is depressed, or otherwise moved, a distal end of the plunger can engage the proximal end 3822 of the syringe plunger 3820 and can depress the syringe plunger 3820. Further, as the syringe plunger 3820 is depressed, the collagen material 3840 can be expelled from the syringe 3800. The collagen material 3840 can be injected into an intervertebral disc, a synovial joint, or other tissue, as described in detail herein.

Description of a First Collagen Delivery Device

Figure 39:
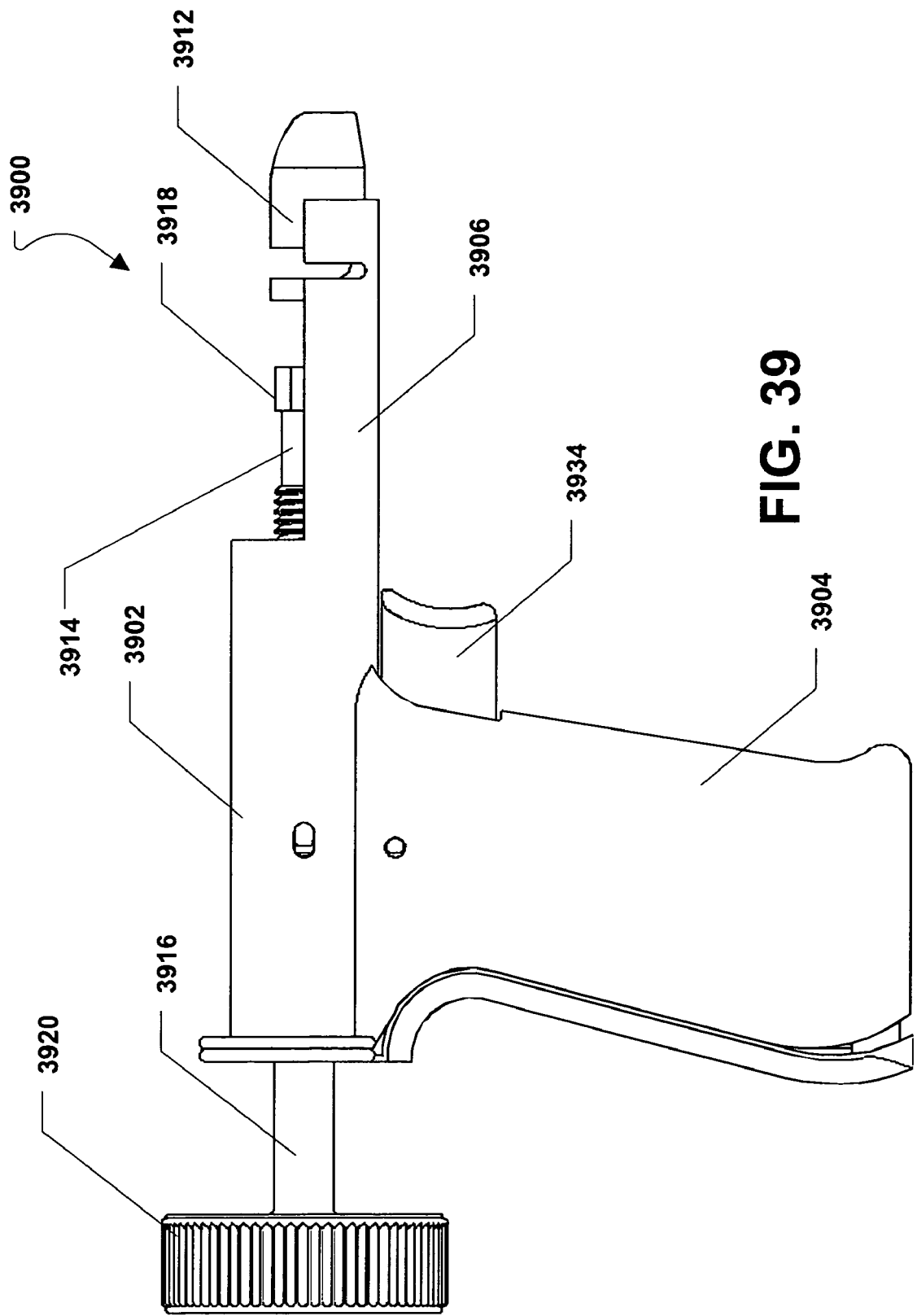
FIG. 39 is a plan view of a first collagen delivery device.
Figure 40:
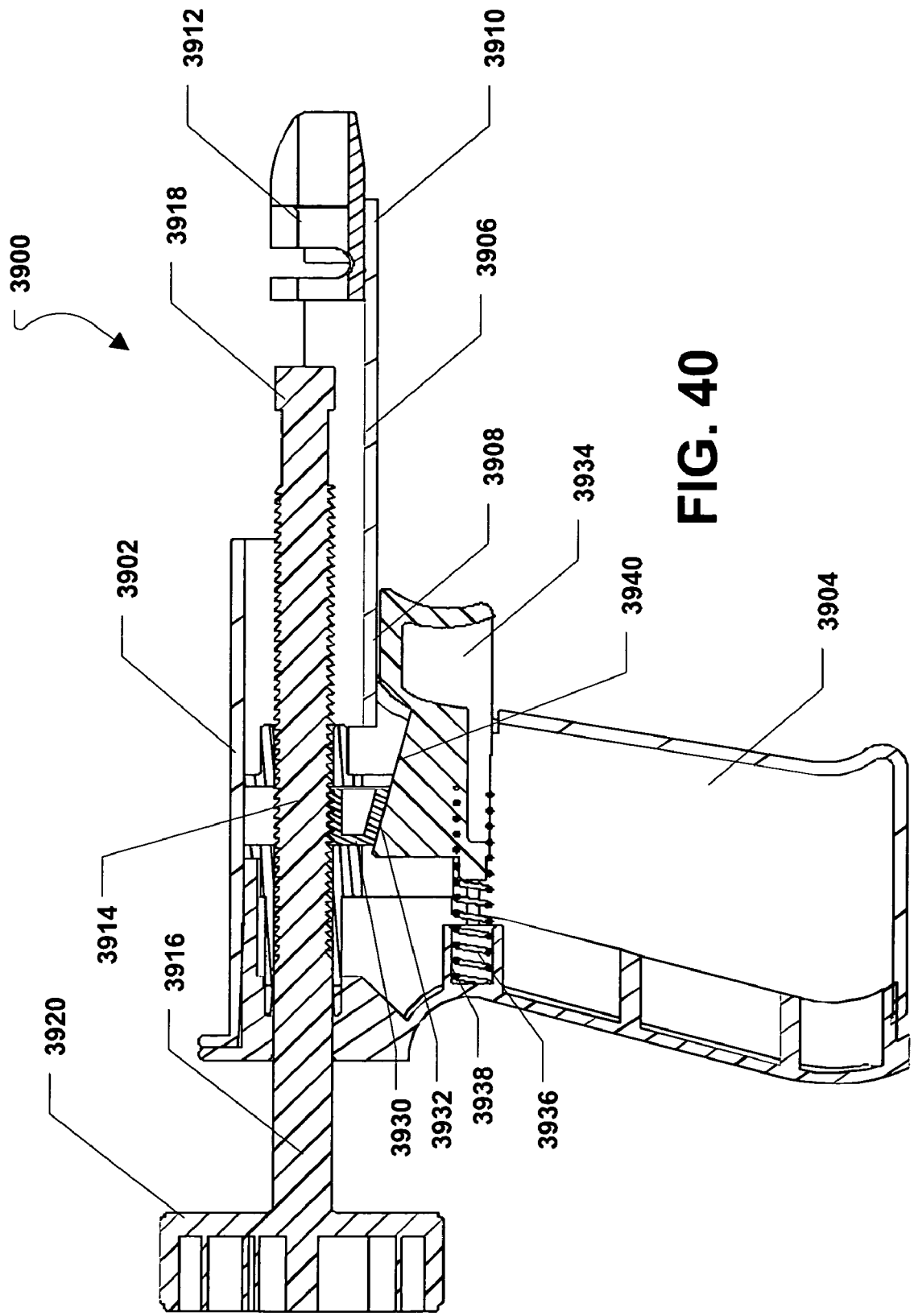
FIG. 40 is a cross-section view of the first collagen delivery device.

FIG. 39 and FIG. 40 depict a first collagen delivery device, generally designated 3900. As illustrated, the collagen delivery device 3900 can include a frame 3902. A handle 3904 can extend from the frame 3902. Further, a barrel 3906 can extend from the frame 3902 nearly perpendicular to the handle 3904. In a particular embodiment, the barrel 3906 can define a proximal end 3908 and a distal end 3910. A syringe support tip 3912 can be affixed to, or otherwise extend from, the distal end 3910 of the barrel 3906. The syringe support tip 3912 can be configured to receive and removably engage a syringe, e.g., a syringe as shown in FIG. 38.

FIG. 39 and FIG. 40 indicate that the collagen delivery device 3900 can include a threaded plunger 3914 disposed within the frame 3902. The threaded plunger 3914 can extend into the barrel 3906 of the collagen delivery device 3900. In a particular embodiment, the threaded plunger 3914 can include a proximal end 3916 and a distal end 3918. Also, a plunger handle 3920 can be attached to the proximal end 3916 of the threaded plunger 3914. In a particular embodiment, a user can rotate the plunger handle 3918 in order to rotate the threaded plunger 3914 and move the threaded plunger 3914 within the frame 3902 and barrel 3906, as described below.

As shown in FIG. 40, a half nut 3930 can be disposed within the frame 3902. In a particular embodiment, the half nut 3930 can be threaded and can engage the threaded plunger 3912. As the threaded plunger 3914 is rotated, e.g., clockwise or counter-clockwise, the threaded plunger 3914 can move linearly back and forth within the frame 3902 and the barrel 3906. As illustrated, the half nut 3930 can include a ramped surface 3932.

FIG. 40 further depicts a trigger 3934 that can be slidably disposed within the frame 3902. A spring 3936 can be installed between the trigger 3934 and a spring pocket 3938 established within the frame 3902. In a particular embodiment, the spring 3936 can be installed under compression and can keep the trigger 3934 fully extended with respect to the frame 3902. As shown, the trigger 3934 can also include a ramped surface 3940.

In a particular embodiment, as shown in FIG. 40, when the trigger 3934 is fully extended with respect to the frame 3902, the ramped surface 3940 of the trigger 3934 can engage the ramped surface 3932 of the half nut 3930 in order to keep the half nut 3930 in contact with the threaded plunger 3914. As such, when the plunger handle 3920 is rotated, the threads on the threaded plunger 3914 can cooperate with the threads on the half nut 3930 in order to move the threaded plunger 3914 linearly, backward or forward, with respect to the frame 3902 and the barrel 3906. As the threaded plunger 3914 moves forward, the distal end 3918 of the threaded plunger 3914 can engage a plunger (not shown in FIG. 40) within a syringe (not shown in FIG. 40) and can cause the syringe to expel a collagen material, e.g., a collagen material according to one or more of the embodiments described herein.

When the trigger 3934 is depressed, and the spring 3936 is further compressed, the ramped surface 3940 of the trigger 3934 can slide with respect to the ramped surface 3932 of the half nut 3930 and can allow the half nut 3930 to move away from the threaded plunger 3914 and disengage the threaded plunger 3914. When the half nut 3930 disengages the threaded plunger 3914, the threaded plunger 3914 can slide freely within the frame 3902 and the barrel 3906. Accordingly, a user can rotate the threaded plunger 3914 in order to inject a collagen material. Further, when injection is complete, the user can depress the trigger and slide the threaded plunger 3914 away from a syringe in order to remove the syringe from the collagen delivery device 3900.

The collagen delivery device 3900 can be considered an open device since it is configured to receive a separate syringe. However, in another embodiment, the barrel 3906 of the collagen delivery device 3900 can be a closed barrel 3906 and the closed barrel 3906 can be configured to receive a collagen material therein. In such an embodiment, the collagen deliver device 3900 can be considered a closed device. In such a closed device, the barrel 3906 can include one or more additional ports that can be utilized to inject an additional material into the collagen delivery device 3900 to be mixed with a collagen material therein.

Further, in an alternative embodiment, the plunger 3914 can include a pressure transducer, or pressure gauge, that can be used to monitor the delivery pressure applied by the collagen delivery device 3900. The pressure transducer can be incorporated into the distal end 3918 of the plunger 3914.

Description of a Second Collagen Delivery Device

Figure 41:
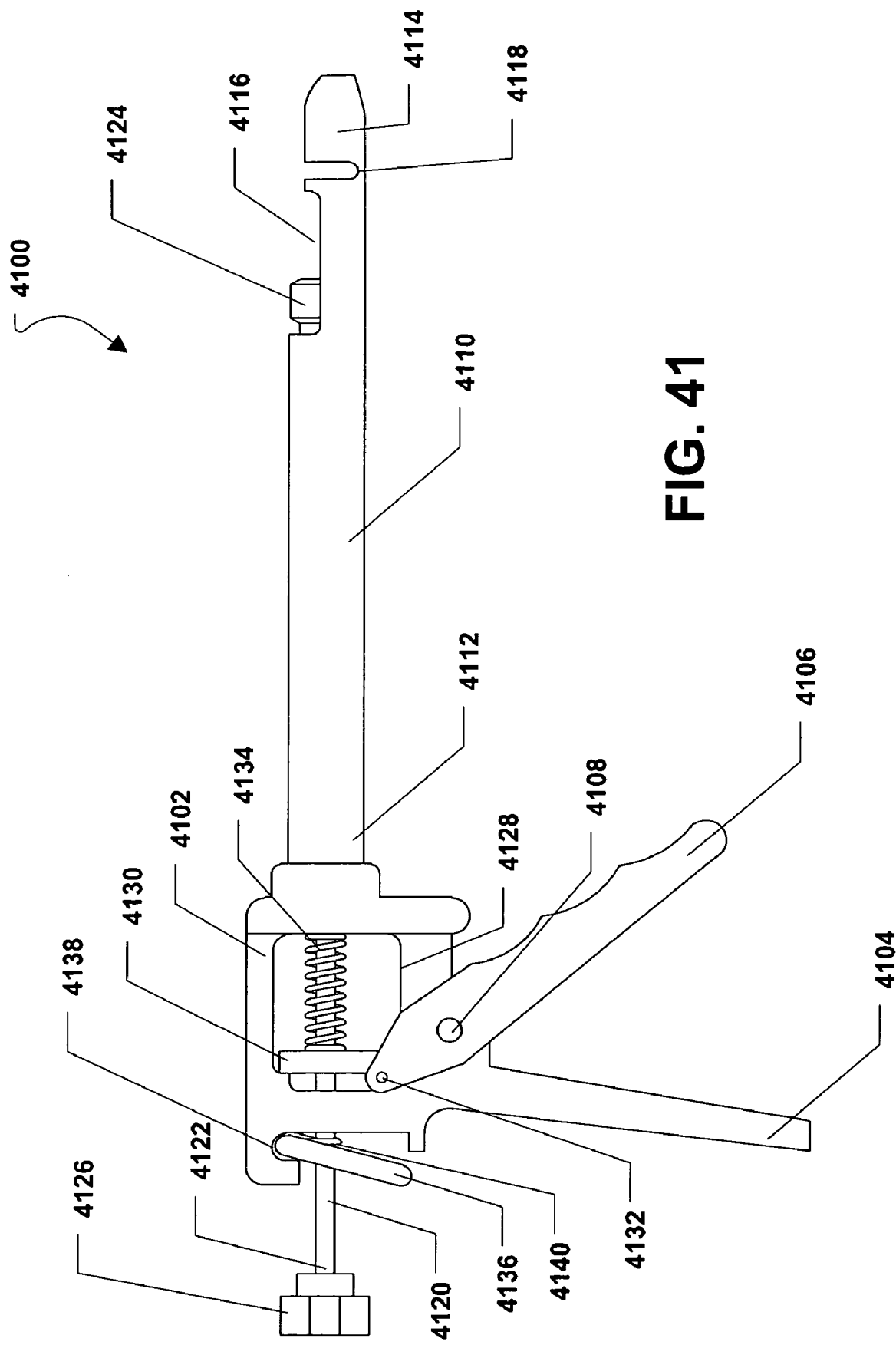
FIG. 41 is a plan view of a second collagen delivery device.

FIG. 41 depicts a second collagen delivery device, generally designated 4100. As illustrated, the collagen delivery device 4100 can include a frame 4102. A stationary handle 4104 can extend from the frame 4102. Also, a rotatable handle 4106 can be attached to the frame 4102 near the stationary handle 4104. The rotatable handle 4106 can be attached to the frame 4102 via a first pin 4108 and can rotate with respect to the frame 4102 around the first pin 4108.

As illustrated in FIG. 41, the collagen delivery device 4100 can include a barrel 4110 that can extend from the frame 4102 nearly perpendicular to the stationary handle 4104. In a particular embodiment, the barrel 4110 can define a proximal end 4112 and a distal end 4114. The proximal end 4112 of the barrel 4110 can be attached to the frame 4102. Further, the distal end 4114 of the barrel 4110 can include a syringe chamber 4116. Also, the barrel 4110 can include a syringe notch 4118 formed near the distal end 4114 of the barrel 4110 within the syringe chamber 4116. Accordingly, the syringe chamber 4116 is sized and shaped to receive a syringe, e.g., a syringe configured as shown in FIG. 39.

FIG. 41 further indicates that the collagen delivery device 4100 can include a plunger 4120 that can be slidably disposed within the frame 4102 and the barrel 4110. The plunger 4120 can include a proximal end 4122 and a distal end 4124. Also, a plunger handle 4126 can be attached to the proximal end 4122 of the plunger 4120.

In a particular embodiment, the frame 4102 includes an opening 4128. When the plunger 4120 is installed within the frame 4102 and the barrel 4110, a portion of the plunger 4120 can be exposed within the opening 4128 of the frame 4102. A plunger advancement tab 4130 can disposed around the plunger 4120 within the opening 4128 of the frame 4102. The plunger advancement tab 4130 can be coupled, or otherwise attached, to the rotatable handle 4106 by a second pin 4132.

As depicted in FIG. 41, a first spring 4134 is installed in compression around the plunger 4120 within the opening 4128 of the frame 4102. The first spring 4134 is installed between the plunger advancement tab 4130 and the front of the opening 4128 in the frame 4102. The first spring 4134 can bias the plunger advancement tab 4130 to the back of the opening 4128 in the frame 4102. FIG. 41 also shows a plunger locking tab 4136 installed around the plunger 4120 behind the opening 4128 in the frame 4102.

The top of the plunger locking tab 4136 can engage a notch 4138 formed in the frame 4102 behind the opening 4128. Moreover, a second spring 4140 can be installed in compression between the plunger locking tab 4136 and the frame 4102, e.g., between the plunger locking tab 4136 and the portion of the frame 4102 behind the opening 4128 established therein. The second spring 4140 can bias the plunger locking tab 4136 away from the frame 4102, i.e., toward the proximal end 4122 of the plunger 4120, and the top of the plunger locking tab 4136 can engage the notch 4138 in the tab. Accordingly, the plunger locking tab 4136 can be cocked at angle with respect to the plunger 4120 and can prevent the plunger 4120 from sliding backward with respect to the frame 4102.

In a particular embodiment, the rotatable handle 4106 can be rotated around the pin 4108 toward the stationary handle 4104. As the rotatable handle 4106 moves toward the stationary handle 4104, the plunger advancement tab 4130 engages the plunger 4120 and slides the plunger 4120 forward, i.e., toward the distal end 4114 of the barrel 4110. As the plunger 4120 moves forward, the distal end 4124 of the plunger 4120 can engage a syringe plunger (not shown in FIG. 41) within a syringe (not shown in FIG. 41) and can push the syringe plunger in order to cause the syringe to expel a collagen material, e.g., a collagen material according to one or more of the embodiments described herein.

The plunger locking tab 4136 can be advanced forward in order to unlock the plunger 4120 and allow the plunger to slide freely within the frame 4102 and the barrel 4110. In particular, the bottom of the plunger locking tab 4136 can be pushed toward the frame 4102 in order to uncock the plunger locking tab 4136 with respect to the plunger 4120. When the plunger locking tab 4136 is substantially perpendicular to the plunger 4120, the plunger 4120 can slide freely within the plunger locking tab 4136 and as such, the plunger 4120 can slide freely within the frame 4102 and the barrel 4110. Accordingly, a user can squeeze the rotatable handle 4106 toward the stationary handle 4104 in order to inject a collagen material, e.g., into an intervertebral disc, a synovial joint, or other tissue. Further, when injection is complete, the user can depress the plunger locking tab 4136, as described herein, and slide the plunger 4120 away from a syringe in order to remove the syringe from the collagen delivery device 4100.

Conclusion

With the configuration of structure described above, the injectable collagen material according to one or more of the embodiments provides a material that can be injected into an intervertebral disc, a synovial joint, or other tissue, in order to augment the intervertebral disc, the synovial joint, or other tissue, and to prevent further deterioration of the intervertebral disc, the synovial joint, or other tissue. The material can be injected as part of a solution, e.g., a slurry or gel. Further, the material can be injected dry and hydrated in situ. Also, the material can be cross-linked prior to injection or cross-linked in situ. In addition to the material, one or more additives can be injected with the material.

In a particular embodiment, the collagen material can be injected as prescribed in the various methods of treating described herein. Further, the collagen material can be injected using one or more of the collagen delivery devices described herein.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An injectable collagen material for treating an intervertebral disc, consisting essentially of:
   a plurality of cross-linked, cut and ground collagen particles, wherein each particle comprises:
   an elongated, thin body having one or more arcuate portions and one or more straight portions; and
   one or more fibers extending from the body, wherein the one or more fibers of one particle engage the one or more fibers of one or more other particles to establish a matrix of material;
   wherein the collagen particles have a moisture content less than or approximately equal to 10% by weight; and
   wherein the density of the collagen material when dry, is between one-tenth of a gram per cubic centimeter and one gram per cubic centimeter, and wherein the collagen material comprises a biological factor comprising LIM mineralization protein.

2. The injectable collagen material of claim 1, wherein a portion of the one or more fibers are ribbon-shaped.

3. The injectable collagen material of claim 2, wherein a portion of the one or more fibers are hook-shaped.

4. The injectable collagen material of claim 3, wherein a portion of the one or more fibers are loop-shaped.

5. The injectable collagen material of claim 4, wherein at least one hook-shaped fiber engages at least one loop-shaped fiber.

6. The injectable collagen material of claim 5, wherein at least one ribbon-shaped fiber intertwines with at least one other ribbon-shaped fiber.

7. The injectable collagen material of claim 4, wherein at least one hook-shaped fiber engages at least one loop-shaped fiber, at least one other hook-shaped fiber, or a combination thereof.

8. The injectable collagen material of claim 2, wherein at least one ribbon-shaped fiber intertwines with at least one other ribbon-shaped fiber.

9. The injectable collagen material of claim 1, wherein one-tenth grams to one gram of the collagen material is mixed with one-tenth cubic centimeters to ten cubic centimeters of saline to form a collagen slurry.

10. The injectable collagen material of claim 9, wherein the collagen slurry can be injected using a needle.

11. The injectable collagen material of claim 1, wherein one two-tenths grams to five-tenths grams of the collagen material is mixed with two-tenths cubic centimeters to five cubic centimeters of saline to form a collagen slurry.

12. The injectable collagen material of claim 1, further comprising an additive.

13. The injectable collagen material of claim 12, wherein the additive comprises a radiocontrast medium, a drug, a cellular matter, a biological factor, or a combination thereof.

14. The injectable collagen material of claim 13, wherein the drug comprises an antibiotic, an analgesic, an anti-inflammatory drug, an anti- TNF-alpha, a steroid, or a combination thereof.

15. The injectable collagen material of claim 13, wherein the cellular matter comprises bone marrow derived stem cells, lipo derived stem cells, or a combination thereof.

16. The injectable collagen material of claim 13, wherein the biological factor comprises bone morphogenetic protein (BMP), cartilage-derived morphogenetic protein (CDMP), platelet derived growth factor (PDGF), insulin-like growth factor (IGF), fibroblast growth factor (FGF), osteoblast growth factor, or a combination thereof.

17. The injectable collagen material of claim 12, wherein the additive promotes slurry formation, gel formation, or a combination thereof.

18. The injectable collagen material of claim 12, wherein the additive promotes protein folding, water binding, protein-to-protein interaction, water immobilization, or a combination thereof.

19. The injectable collagen material of claim 12, wherein the additive comprises a polysaccharide.

20. The injectable collagen material of claim 19, wherein the polysaccharide comprises proteoglycan, hyaluronic acid, or combination thereof.

21. A kit for field use, comprising: a syringe;
an injectable cross-linked collagen material of claim 1 having a density when dry between one-tenth of a gram per cubic centimeter and one gram per cubic centimeter; and
a fluid.

22. The injectable collagen material of claim 1, wherein the collagen particles are freeze dried.

23. The injectable collagen material of claim 1, wherein the collagen particles have a moisture content less than or equal to 6% by weight.

24. An injectable collagen material for treating an intervertebral disc consisting essentially of:
a plurality of cross-linked, cut and ground particles having a mean size of at least 0.25 mm, wherein each particle comprises:
an elongated, thin body having one or more arcuate portions and one or more straight portions; and
one or more fibers extending from the body, wherein the one or more fibers of one particle engage the one or more fibers of one or more other particles to establish a matrix of material, wherein the collagen particles have a moisture content less than or approximately equal to 10% by weight; and
wherein the density of the collagen material when dry, is between one-tenth of a gram per cubic centimeter and one gram per cubic centimeter, and wherein the collagen material comprises a biological factor comprising LIM mineralization protein.

25. The injectable collagen material of claim 24, wherein the mean size is not greater than 5.0 mm.

26. The injectable collagen material of claim 25, wherein the mean size is not greater than 1.5 mm.

27. The injectable collagen material of claim 24, wherein the collagen particles have a moisture content less than or equal to 6% by weight.

* * * * *